US009663440B2

(12) United States Patent
Johns et al.

(10) Patent No.: US 9,663,440 B2
(45) Date of Patent: May 30, 2017

(54) CROSS METATHESIS OF POLY-BRANCHED POLY-OLEFINS

(71) Applicant: MATERIA, INC., Pasadena, CA (US)

(72) Inventors: Adam M. Johns, Claremont, CA (US); Richard L. Pederson, San Gabriel, CA (US); Rosemary Conrad Kiser, Sierra Madre, CA (US); Andrew Nickel, San Marino, CA (US)

(73) Assignee: MATERIA, INC., Pasadena, CA (US)

( * ) Notice: Subject to any disclaimer, the term of this patent is extended or adjusted under 35 U.S.C. 154(b) by 0 days.

(21) Appl. No.: 14/782,699

(22) PCT Filed: Apr. 9, 2014

(86) PCT No.: PCT/US2014/033528
§ 371 (c)(1),
(2) Date: Oct. 6, 2015

(87) PCT Pub. No.: WO2014/169055
PCT Pub. Date: Oct. 16, 2014

(65) Prior Publication Data
US 2016/0107980 A1    Apr. 21, 2016

Related U.S. Application Data

(60) Provisional application No. 61/810,149, filed on Apr. 9, 2013, provisional application No. 61/942,175, filed on Feb. 20, 2014.

(51) Int. Cl.
*C07C 51/00*    (2006.01)
*C07C 67/283*    (2006.01)
(Continued)

(52) U.S. Cl.
CPC ............. *C07C 67/283* (2013.01); *C07C 2/02* (2013.01); *C07C 2/32* (2013.01); *C07C 5/03* (2013.01);
(Continued)

(58) Field of Classification Search
CPC .................................................. C07C 67/283
See application file for complete search history.

(56) References Cited

U.S. PATENT DOCUMENTS 3,732,323 A * 5/1973 Osaki ....................... C07C 2/04
585/438
3,848,010 A    11/1974 Intille
(Continued)

FOREIGN PATENT DOCUMENTS

EP    1757613 B1    1/2011
EP    1577282 B1    6/2011
(Continued)

OTHER PUBLICATIONS

Martinez, et al.,Metathesis Transformations of Natural Products; Cross-Metathesis of Natural Rubber and Mandarin Oil by Ru-Aikylidene Catalysts', Molecules, vol. 17, 2012, pp. 6001-6010.*
(Continued)

*Primary Examiner* — Deborah D Carr
(74) *Attorney, Agent, or Firm* — J.A. Lindeman & Co., PLLC

(57) ABSTRACT

This invention describes processes to make products by cross metathesis of functionalized or non-functionalized olefins with poly-branched poly-olefins such as terpenes (e.g., farnesene(s), α-farnesene, β-farnesene, β-myrcene, etc.) and compositions made by such methods. More particularly, the present invention relates to methods of making (i) cross metathesis products by a cross metathesis reaction between at least one hydrovinylated olefinic substrate and at
(Continued)

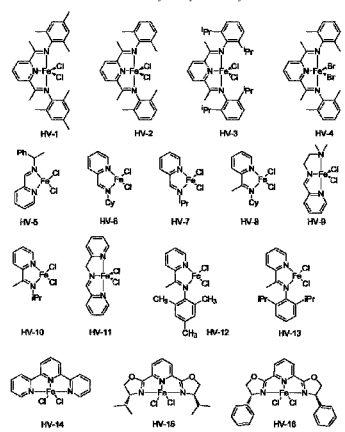

Chemical structures of hydrovinylation catalysts HV-1 to HV-16 least one hydrovinylated cross metathesis substrate in the presence of at least one olefin metathesis catalyst; (ii) cross metathesis products by a cross metathesis reaction between at least one hydrovinylated olefinic substrate and at least one cross metathesis substrate in the presence of at least one olefin metathesis catalyst; and (iii) cross metathesis products by a cross metathesis reaction between at least one olefinic substrate and at least one hydrovinylated cross metathesis substrate in the presence of at least one olefin metathesis catalyst; as well as compositions made by such methods.

11 Claims, 4 Drawing Sheets

(51) Int. Cl.

| | | |
|---|---|---|
| C07F 11/00 | (2006.01) | |
| C07F 15/00 | (2006.01) | |
| C07C 67/343 | (2006.01) | |
| C07C 67/475 | (2006.01) | |
| C07C 303/06 | (2006.01) | |
| C07C 303/24 | (2006.01) | |
| C07C 2/02 | (2006.01) | |
| C07C 5/03 | (2006.01) | |
| C07C 6/04 | (2006.01) | |
| C07C 2/32 | (2006.01) | |
| C07C 29/147 | (2006.01) | |
| C07C 41/26 | (2006.01) | |
| C07C 67/347 | (2006.01) | |

(52) U.S. Cl.
CPC ............ *C07C 6/04* (2013.01); *C07C 29/147* (2013.01); *C07C 41/26* (2013.01); *C07C 67/343* (2013.01); *C07C 67/347* (2013.01); *C07C 67/475* (2013.01); *C07C 303/06* (2013.01); *C07C 303/24* (2013.01); *C07F 11/00* (2013.01); *C07F 15/0046* (2013.01); *C07C 2521/18* (2013.01); *C07C 2523/44* (2013.01); *C07C 2531/22* (2013.01); *C07C 2531/24* (2013.01)

(56) References Cited

U.S. PATENT DOCUMENTS

| | | | |
|---|---|---|---|
| 5,227,561 A | 7/1993 | Drent | |
| 5,342,909 A | 8/1994 | Grubbs et al. | |
| 5,977,393 A | 11/1999 | Grubbs et al. | |
| 6,284,852 B1 | 9/2001 | Lynn et al. | |
| 6,486,279 B2 | 11/2002 | Lynn et al. | |
| 6,531,562 B2 | 3/2003 | Jung et al. | |
| 6,552,139 B1 | 4/2003 | Herrmann et al. | |
| 6,613,910 B2 | 9/2003 | Grubbs et al. | |
| 6,635,768 B1 | 10/2003 | Herrmann et al. | |
| 6,787,620 B2 | 9/2004 | Herrmann et al. | |
| 6,838,489 B2 | 1/2005 | Bell et al. | |
| 7,060,852 B2 | 6/2006 | Maas et al. | |
| 7,294,717 B2 | 11/2007 | Herrmann et al. | |
| 7,378,528 B2 | 5/2008 | Herrmann et al. | |
| 7,399,323 B2 | 7/2008 | Renninger et al. | |
| 7,652,145 B2 | 1/2010 | Herrmann et al. | |
| 7,671,224 B2 | 3/2010 | Winde et al. | |
| 7,687,635 B2 | 3/2010 | Verpoort et al. | |
| 7,868,115 B1 | 1/2011 | McPhee | |
| 8,257,957 B2 | 9/2012 | Keasling et al. | |
| 2003/0055262 A1 | 3/2003 | Grubbs et al. | |
| 2004/0186325 A1 | 9/2004 | Maas et al. | |
| 2005/0107628 A1 | 5/2005 | Roper et al. | |
| 2007/0043188 A1 | 2/2007 | Schaubroeck et al. | |
| 2007/0155975 A1* | 7/2007 | Grubbs .................... C07C 6/04 556/81 |
| 2008/0274523 A1 | 11/2008 | Renninger et al. | |
| 2008/0293905 A9 | 11/2008 | Schaubroeck et al. | |
| 2010/0137649 A1 | 6/2010 | Scheibel et al. | |
| 2010/0145086 A1 | 6/2010 | Schrodi et al. | |
| 2013/0225462 A1 | 8/2013 | Di Biase et al. | |

FOREIGN PATENT DOCUMENTS

| | | | | |
|---|---|---|---|---|
| NL | WO 2004101476 A1 * | 11/2004 | ........... C07C 269/06 |
| WO | 02/079208 A2 | 10/2002 | |
| WO | 03/011455 A1 | 2/2003 | |
| WO | 2004/101476 A1 | 11/2004 | |
| WO | 2007/139924 A2 | 12/2007 | |
| WO | 2007/140339 A2 | 12/2007 | |
| WO | 2010/037550 A1 | 4/2010 | |
| WO | 2012/097379 A2 | 7/2012 | |
| WO | 2012/129482 A2 | 9/2012 | |
| WO | 2013/130372 A1 | 9/2013 | |

OTHER PUBLICATIONS

International Preliminary Report on Patentability in International Application No. PCT/US2014/033528, dated Oct. 22, 2015.
International Search Report and Written Opinion of the International Searching Authority in International Application No. PCT/US2014/033528, dated Aug. 29, 2014.
Chatterjee, AK et al., "A General Model for Selectivity in Olefin Cross Metathesis," J. of Am. Chem. Soc., vol. 125, 2003, pp. 11360-11370.
Martinez, A. et al., "Metathesis Transformations of Natural Products: Cross-Metathesis of Natural Rubber and Mandarin Oil by Ru-Alkylidene Catalysts," Molecules, vol. 17, May 18, 2012, pp. 6001-6010.
Arai et al., "1,2-Asymmetric Induction in the SN2'-Allylation of Organocopper and Organozinc Reagents," J. Org. Chem. 1993, 58, pp. 5121-5129.
Ceder et al., "Hydrovinylation of styrene derivatives to 3-aryl-1-butenes catalysed by nickel complexes," J. Mol. Catalysis 92, (1994), pp. 127-139.
Doe et al., "Surfactants for Producing Low Interfacial Tensions I: Linear Alkyl Benzene Sulfonates," J. Am. Oil Chem. Soc. vol. 54, pp. 570-577.
Fassina et al., "Nickel Catalyzed Hydrovinylation of Arylethylenes: General Method of Synthesis of -Arylpropionic Acids Intermediates," Tetrahedron 56 (2000), pp. 7403-7409.
Foster C. Norman, "Sulfonation and Sulfation Processes," The Chemithon Corporation, 1997, pp. 1-36.
Glasspoole et al., "Suzuki-Miyaura cross-couplings of secondary allylic boronic esters," Chem. Commun., 2012, 48, pp. 1230-1232.
Grutters et al., "Highly Selective Cobalt-Catalyzed Hydrovinylation of Styrene," Adv. Synth. Catal. 2009, 351, pp. 2199-2208.
Grutters et al., "Highly Selective Cobalt-Catalyzed Hydrovinylation of Styrene," J. Am. Chem. Soc., 2006, 128, pp. 7414-7415 and supportive information.
Hoveyda et al., "H-Bonding as a Control Element in Stereoselective Ru-Catalyzed Olefin Metathesis," J. Am. Chem. Soc., 2009, 131, pp. 8378-8379 and supporting information.
T.V. Rajanbabu "Asymmetric Hydrovinylation Reaction," Chem. Rev., 2003, 103, pp. 2845-2860.
T.V. Rajanbabu "In Pursuit of an Ideal C-C Bond-Forming Reaction: Development and Applications of the Hydrovinylation of Olefins," NIH Author Manuscript, Synlett, PMC Jul. 14, 2009 pp. 1-96.
Sanchez et al., "A Ruthenium-Based Catalyst System for Hydrovinylation at Room Temperature," Organomettalics, 2008, 27, pp. 2902-2904.
Dewey L. Smith, "Impact of Composition on the Performance of Sodium Linear Alkylbenzenesulfonate (NaLAS)1," JAOCS, vol. 74, No. 7 (1007), pp. 837-845.
Van Zijl et al., "Catalytic Enantioselective Synthesis of Vicinal Dialkyl Arrays," J. Org. Chem., 2008, 73, pp. 6994-7002.
Yi et al., "Hydrovinylation and [2+2] Cycloaddition Reactions of Alkynes and Alkenes Catalyzed by a Well-Defined Cationic Ruthe-

(56) References Cited

OTHER PUBLICATIONS nium-Alkylidene Complex," Organometallics, vol. 18, No. 11, 1999, pp. 2043-2045 and supportive information.

Yi et al., "Hydrovinylation of Alkenes Catalyzed by the Ruthenium-Hydride Complex Formed in Situ from (PCy3)2(CO) RuHCI and HBF4 OEt2," Organometallics, 2001, 20, pp. 802-804.

Anderson et al., "Kinetic Selectivity of Olefin Metathesis Catalysts Bearing Cyclic (Alkyl)(Amino) Carbenes," Organometallics, 2008, 27, pp. 563-566.

Burdett et al., "Renewable Monomer Feedstocks via Olefin Metathesis: Fundamental Mechanistic Studies of Methyl Oleate Ethenolysis with the First-Generation Grubbs Catalyst," Organometallics, 2004, 23, pp. 2027-2047.

"Chemical & Engineering News," vol. 89, No. 4, Jan. 24, 2011, pp. 1-56.

Noramn C. Foster, "Sulfonation and Sulfation Processes," Chemithon Corporation, 1997, pp. 1-36.

Robert H. Grubbs and Sukbok Chang, "Recent Advances in Olefin Metathesis and Its Application in Organic Synthesis," Tetrahedron, 54, 1998, pp. 4413-4450.

Nickel et al., "A Highly Efficient Olefin Metathesis Process for the Synthesis of Terminal Alkenes from Fatty Acid Esters," Springer, Jun. 21, 2012.

T.V. Rajanbabu, "In Pursuit of an Ideal C-C Bond-Forming Reaction: Development and Applications of the Hydrovinylation of Olefins," NIH Public Access, Author Manuscript, 2009, pp. 1-96.

Sanford et al., "New Insights into the Mechanism of Ruthenium-Catalyzed Olefin Metathesis Reactions," J. Am. Chem. Soc., 2001, 123, pp. 749-750.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," Org. Lett., 1999, vol. 1, No. 6, pp. 953-956.

Richard R. Schrock, "Recent Advances in High Oxidation State Mo and W Imido Alkylidene Chemistry," Chem. Rev., 2009, 109, pp. 3211-3226.

Schwab et al., "Synthesis and Applications of RuC12(=CHR')(PR3)2: The Influence of the Alkylidene Moiety on Metathesis Activity," J. Am. Chem. Soc., 1996, 118, pp. 100-110.

Warwel et al., "Polymers and surfactants on the basis of renewable resources," Chemosphere 43, 2001, pp. 39-48.

Yu et al., "Synthesis of macrocyclic natural products by catalyst-controlled stereoselective ring-closing metathesis," Nature, vol. 479, Nov. 3, 2011, pp. 88-93 and supportive information pp. 1-75.

\* cited by examiner

FIG. 1  Chemical structures of hydrovinylation catalysts HV-1 to HV-16
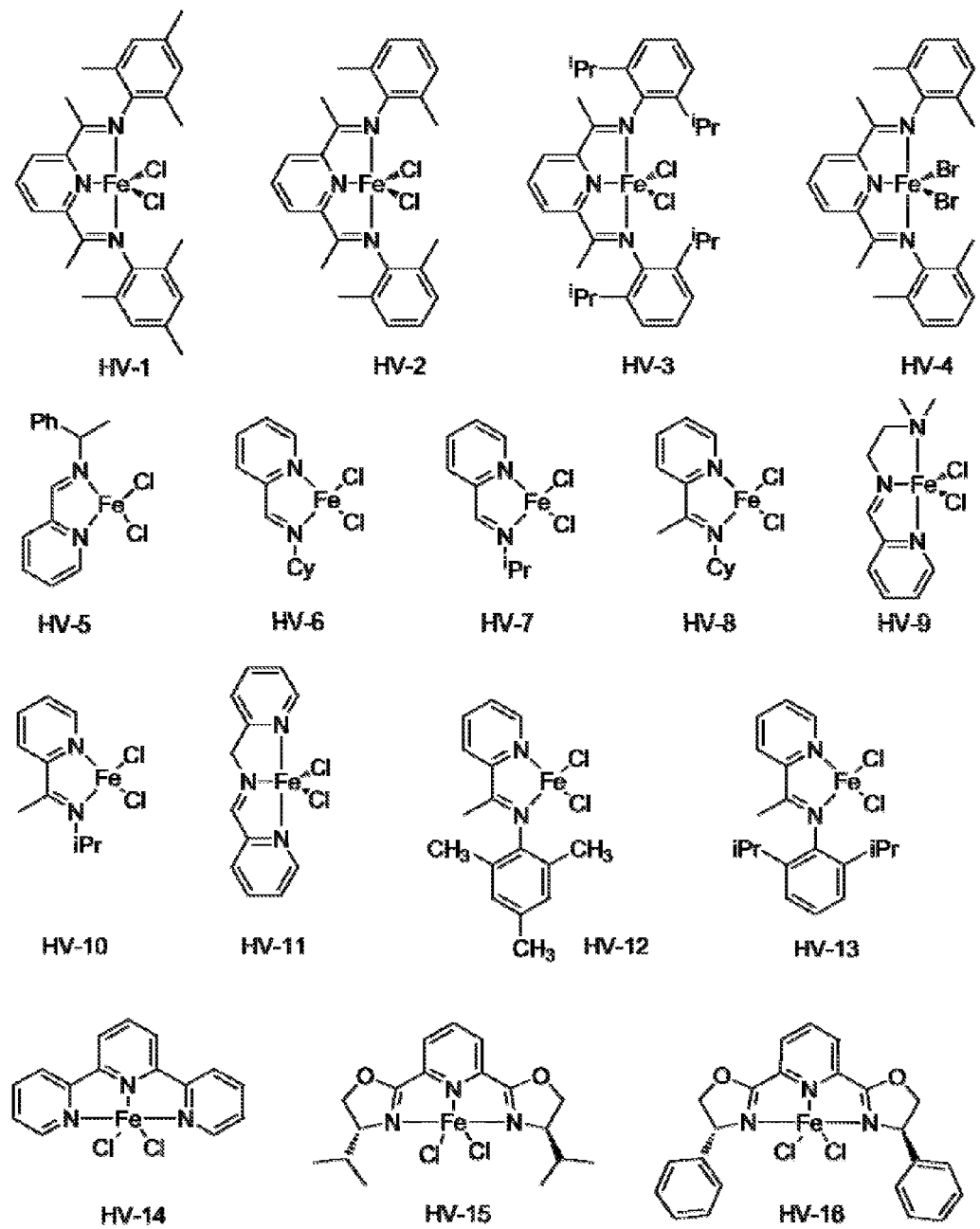

FIG. 2 ¹H NMR of (4E,8E)-5,9,13-trimethyltetradeca-1,4,8,12-tetraene (hydrovinylated farnesene) in CDCl₃
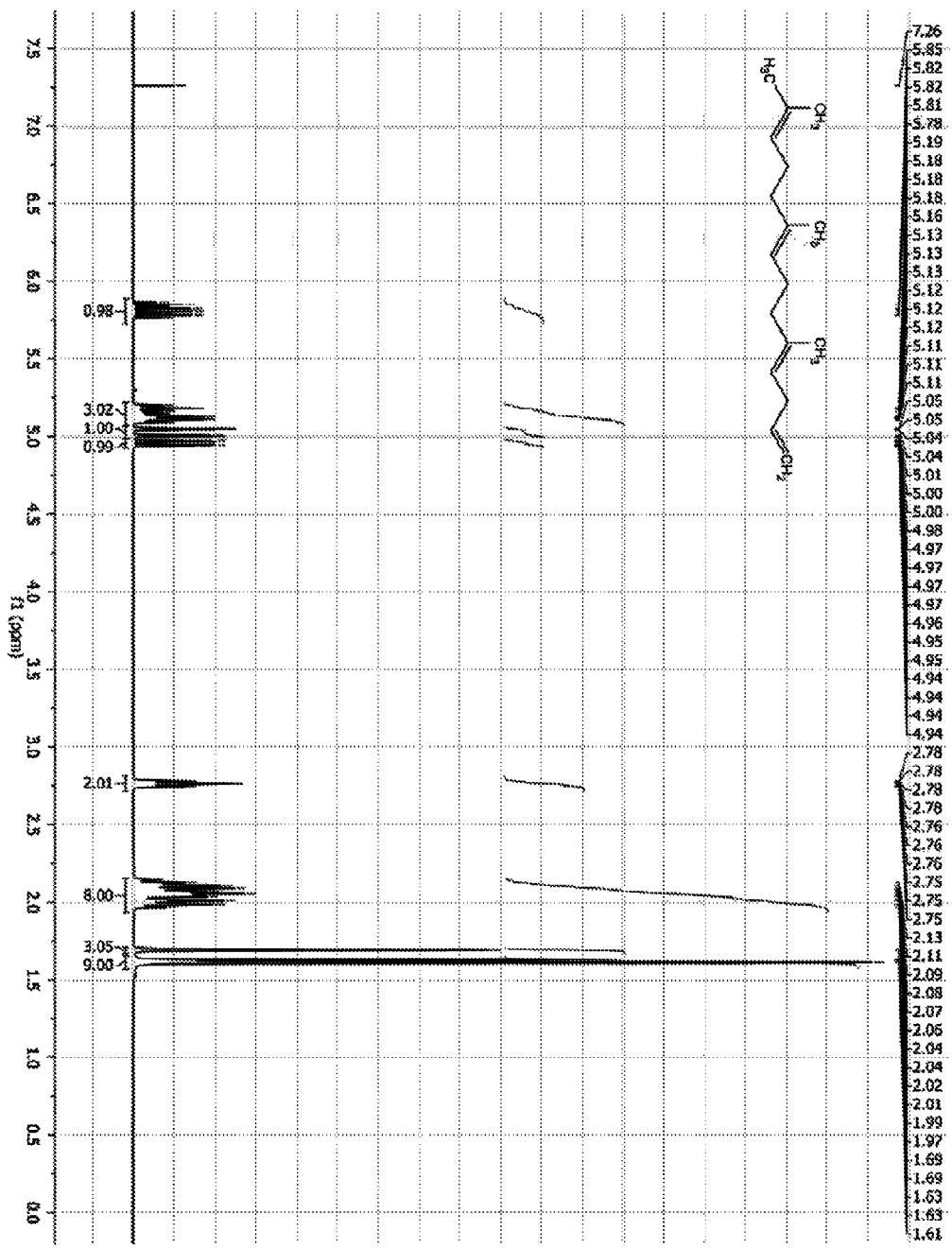

FIG. 3 $^{13}$C NMR of (4*E*,8*E*)-5,9,13-trimethyltetradeca-1,4,8,12-tetraene (hydrovinylated farnesene) in CDCl$_3$
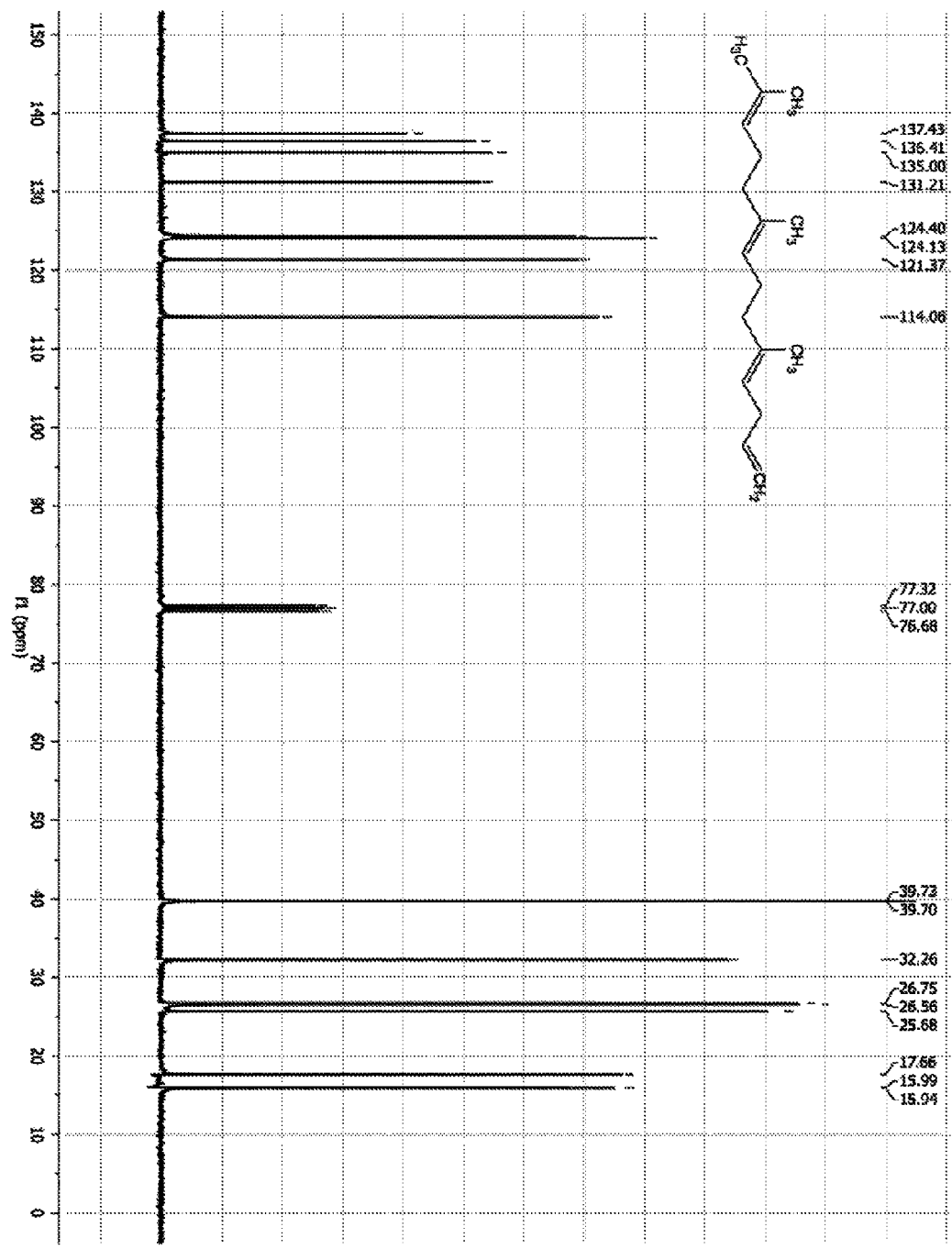

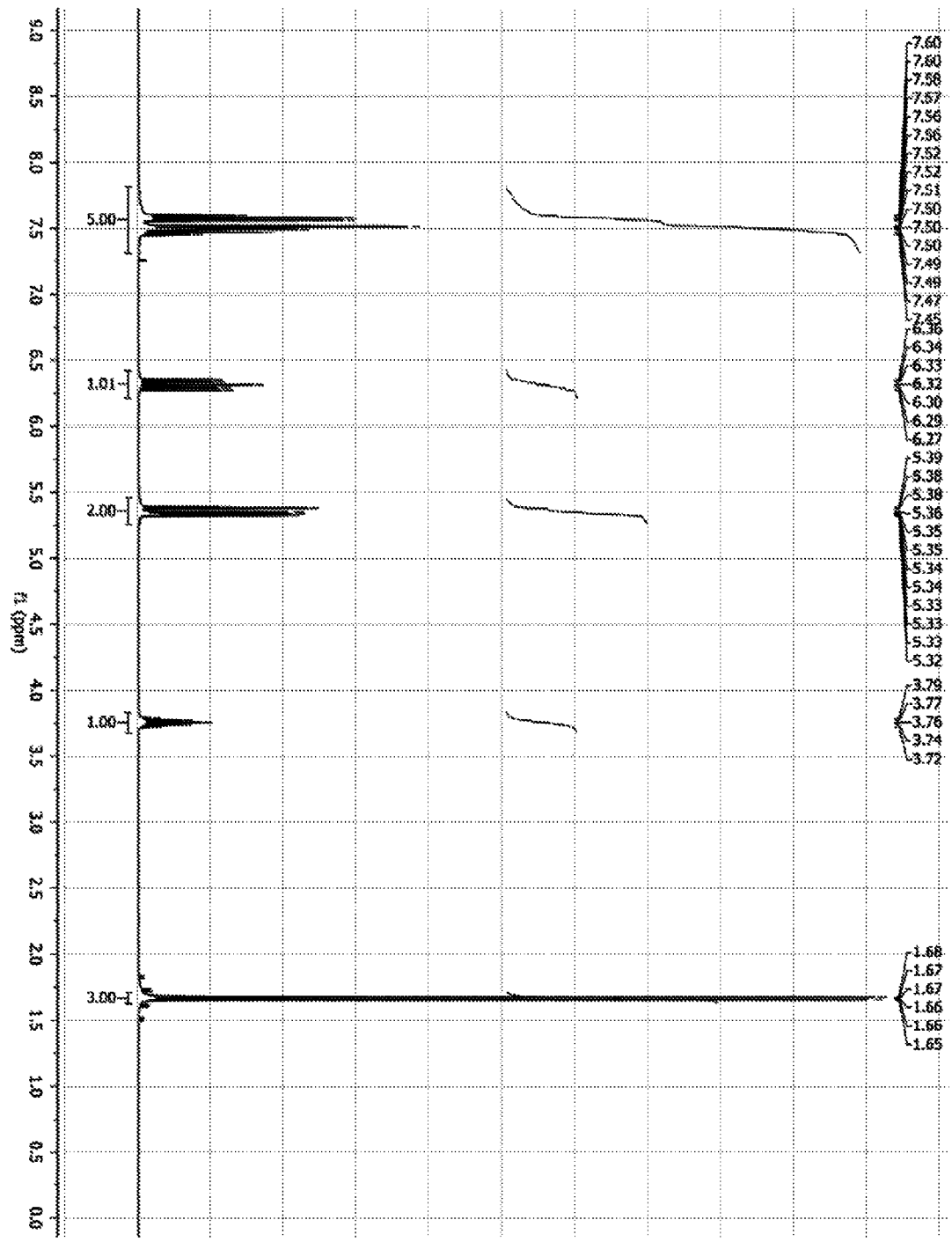
FIG. 4  $^1$H NMR of 3-phenyl-1-butene in CDCl$_3$

US 9,663,440 B2

CROSS METATHESIS OF POLY-BRANCHED POLY-OLEFINS

RELATED APPLICATIONS

This application claims the benefit of U.S. Provisional Patent Application No. 61/810,149, filed Apr. 9, 2013, and U.S. Provisional Patent Application No. 61/942,175, filed Feb. 20, 2014, and the contents of each are incorporated herein by reference.

TECHNICAL FIELD

This invention describes processes to make products by cross metathesis of functionalized or non-functionalized olefins with poly-branched poly-olefins such as terpenes (e.g., farnesene(s), α-farnesene, β-farnesene, β-myrcene, etc.) and compositions made by such methods More particularly, the present invention relates to methods of making (i) cross metathesis products by a cross metathesis reaction between at least one hydrovinylated olefinic substrate and at least one hydrovinylated cross metathesis substrate in the presence of at least one olefin metathesis catalyst; (ii) cross metathesis products by a cross metathesis reaction between at least one hydrovinylated olefinic substrate and at least one cross metathesis substrate in the presence of at least one olefin metathesis catalyst; and (iii) cross metathesis products by a cross metathesis reaction between at least one olefinic substrate and at least one hydrovinylated cross metathesis substrate in the presence of at least one olefin metathesis catalyst; as well as compositions made by such methods. Such products are useful as commercially important materials such as fuels (e.g., diesel fuel and/or jet fuel), lubricants, surfactants, cosmetics, flavors, fragrances, polymers, plastic additives, home and personal care products, or as precursors for preparing such materials.

BACKGROUND

Olefin metathesis has emerged as a unique and powerful transformation for the interconversion of olefinic hydrocarbons, namely due to the development of well-defined catalysts. See Grubbs, R. H. *Handbook of Metathesis*, Wiley-VCH: Weinheim, Germany (2003). The exceptionally wide scope of substrates and functional group tolerances makes olefin metathesis a valuable technique that quickly and efficiently produces otherwise hard to make molecules, compared to traditional synthetic organic techniques. In particular, certain ruthenium and osmium carbene compounds known as "Grubbs catalysts," have been identified as effective catalysts for olefin metathesis reactions such as, cross metathesis (CM), ring-closing metathesis (RCM), ring-opening metathesis (ROM), ring-opening cross metathesis (ROCM), ring-opening metathesis polymerization (ROMP) and acyclic diene metathesis (ADMET) polymerization. The use of ruthenium alkylidene complexes has greatly expanded the scope of this process due to increased tolerance of organic functionality, moisture, and oxygen.

SUMMARY OF THE INVENTION

The present invention relates to compositions comprising cross metathesis products of functionalized or non-functionalized olefins with poly-branched poly-olefins such as terpenes (e.g., farnesene(s), α-farnesene, β-farnesene, β-myrcene, etc.). In addition, the present invention relates to methods of making cross metathesis products by a cross metathesis reaction between at least one hydrovinylated olefinic substrate and at least one hydrovinylated cross metathesis substrate in the presence of at least one olefin metathesis catalyst. In addition, the present invention relates to methods of making cross metathesis products by a cross metathesis reaction between at least one hydrovinylated olefinic substrate and at least one cross metathesis substrate in the presence of at least one olefin metathesis catalyst. In addition, the present invention relates to methods of making cross metathesis products by a cross metathesis reaction between at least one olefinic substrate and at least one hydrovinylated cross metathesis substrate in the presence of at least one olefin metathesis catalyst are exemplified below. In addition, the present invention relates to methods of making cross metathesis products by a cross metathesis reaction between at least one olefinic substrate and at least one cross metathesis substrate in the presence of at least one olefin metathesis catalyst.

In one embodiment the present invention provides a method of making cross metathesis products the method comprising forming a composition comprising at least one cross metathesis substrate, at least one olefinic substrate, and at least one olefin metathesis catalyst, and subjecting the composition to conditions effective to promote a cross metathesis reaction.

In another embodiment the present invention provides a method of making alkylbenzenes the method comprising forming a composition comprising at least one cross metathesis substrate, at least one olefinic substrate, and at least one olefin metathesis catalyst, wherein the at least one olefinic substrate is an alkene benzene, subjecting the composition to conditions effective to promote a cross metathesis reaction to form cross metathesis products, and subjecting the cross metathesis products to conditions effective to promote olefin hydrogenation.

In another embodiment the present invention provides a method of making alkylbenzene sulfonates the method comprising forming a composition comprising at least one cross metathesis substrate, at least one olefinic substrate, and at least one olefin metathesis catalyst, wherein the at least one olefinic substrate is an alkene benzene, subjecting the composition to conditions effective to promote a cross metathesis reaction to form cross metathesis products, and subjecting the cross metathesis products to conditions effective to promote olefin hydrogenation to form hydrogenation products, where the hydrogenation products comprise at least one alkylbenzene, and subjecting the hydrogenation products comprising at least one alkylbenzene to conditions effective to promote aromatic sulfonation of the at least one alkylbenzene.

In another embodiment the present invention provides a method of making 2-phenyl alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one terpene, and at least one olefin metathesis catalyst, and subjecting the second composition to conditions effective to promote a cross metathesis reaction to form cross metathesis products.

In another embodiment the present invention provides a method of making 2-phenyl alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one hydrovinylated terpene, and at least one olefin metathesis catalyst, and subjecting the second composition to conditions effective to promote a cross metathesis reaction.

In another embodiment the present invention provides a method of making 2-phenyl alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, α-farnesene, and at least one olefin metathesis catalyst, and subjecting the second composition to conditions effective to promote a cross metathesis reaction.

In another embodiment the present invention provides a method of making 2-phenyl alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one hydrovinylated β-farnesene, and at least one olefin metathesis catalyst, subjecting the second composition to conditions effective to promote a cross metathesis reaction.

In another embodiment the present invention provides a method of making 2-phenyl alkylbenzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one hydrovinylated terpene, and at least one olefin metathesis catalyst, subjecting the second composition to conditions effective to promote a cross metathesis reaction to form cross metathesis products, where the cross metathesis products comprise at least one 2-phenyl alkene benzene, and subjecting the cross metathesis products comprising at least one 2-phenyl alkene benzene to conditions effective to promote olefin hydrogenation.

In another embodiment the present invention provides a method of making 2-phenyl alkylbenzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one terpene, and at least one olefin metathesis catalyst, subjecting the second composition to conditions effective to promote a cross metathesis reaction to form cross metathesis products, where the cross metathesis products comprise at least one 2-phenyl alkene benzene, and subjecting the cross metathesis products comprising at least one 2-phenyl alkene benzene to conditions effective to promote olefin hydrogenation.

In another embodiment the present invention provides a method of making 2-phenyl alkylbenzene sulfonates, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one hydrovinylated terpene, and at least one olefin metathesis catalyst, subjecting the second composition to conditions effective to promote a cross metathesis reaction to form cross metathesis products, where the cross metathesis products comprise at least one 2-phenyl alkene benzene, subjecting the cross metathesis products comprising at least one 2-phenyl alkene benzene to conditions effective to promote olefin hydrogenation to form hydrogenation products, where the hydrogenation products comprise at least one 2-phenyl alkylbenzene, and subjecting the hydrogenation products comprising at least one 2-phenyl linear alkylbenzene to conditions effective to promote aromatic sulfonation of the at least one 2-phenyl linear alkylbenzene.

In another embodiment the present invention provides a method of making 2-phenyl alkylbenzene sulfonates, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one terpene, and at least one olefin metathesis catalyst, subjecting the second composition to conditions effective to promote a cross metathesis reaction to form cross metathesis products, where the cross metathesis products comprise at least one 2-phenyl alkene benzene, subjecting the cross metathesis products comprising at least one 2-phenyl alkene benzene to conditions effective to promote olefin hydrogenation to form hydrogenation products, where the hydrogenation products comprise at least one 2-phenyl alkylbenzene, and subjecting the hydrogenation products comprising at least one 2-phenyl linear alkylbenzene to conditions effective to promote aromatic sulfonation of the at least one 2-phenyl linear alkylbenzene.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; and subjecting the second composition to conditions effective to promote a cross metathesis reaction to form at least one cross metathesis product.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; and wherein that at least one olefinic substrate is selected from internal olefins, alpha olefins, or a combination thereof.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product, wherein that at least one olefinic substrate is selected from internal olefins, alpha olefins, or a combination thereof; and wherein the internal olefin or alpha olefin comprises at least one aryl group such that the at least one cross metathesis product comprises the at least one aryl group.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one aryl group such that the at least one cross metathesis product comprises the at least one aryl group; and subjecting the at least one cross metathesis product comprising the at least one aryl group to conditions effective to promote olefin hydrogenation to form at least one hydrogenated cross metathesis product.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one aryl group such that the at least one cross metathesis product comprises the at least one aryl group; subjecting the at least one cross metathesis product comprising the at least one aryl group to conditions effective to promote olefin hydrogenation to form at least one hydrogenated cross metathesis product; and subjecting the at least one hydrogenated cross metathesis product to conditions effective to promote an aromatic sulfonation reaction to form at least one sulfonated cross metathesis product.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; and wherein the internal olefin or alpha olefin comprises at least one functional group selected from hydroxyl or acyloxy such that the at least one cross metathesis product comprises the at least one functional group selected form hydroxyl or acyloxy.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one functional group selected from hydroxyl or acyloxy such that the at least one cross metathesis product comprises the at least one functional group selected from hydroxyl or acyloxy; and subjecting the at least one cross metathesis product comprising the at least one functional group selected from hydroxyl or acyloxy to conditions effective to promote olefin hydrogenation to form at least one hydrogenated cross metathesis product.

In another embodiment the present invention provides a method of making at least one cross metathesis product, the method comprising: forming a first composition comprising at least one cross metathesis substrate, at least one hydrovinylation catalyst, and ethylene; subjecting the first composition to conditions effective to promote a hydrovinylation reaction to form at least one hydrovinylated cross metathesis substrate; forming a second composition comprising the at least one hydrovinylated cross metathesis substrate, at least one olefinic substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one functional group selected from hydroxyl or acyloxy such that the at least one cross metathesis product comprises the at least one functional group selected form hydroxyl or acyloxy; subjecting the at least one cross metathesis product comprising the at least one functional group selected from hydroxyl or acyloxy to conditions effective to promote olefin hydrogenation to form at least one hydrogenated cross metathesis product; and subjecting the at least one hydrogenated cross metathesis product to conditions effective to promote a sulfation reaction to form at least one sulfated cross metathesis product.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; and subjecting the second composition to conditions effective to promote a cross metathesis reaction to form at least one cross metathesis product.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; and wherein that at least one olefinic substrate is selected from internal olefins, alpha olefins, or a combination thereof.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; and wherein that at least one olefinic substrate is selected from internal olefins, alpha olefins, or a combination thereof; and wherein the internal olefin or alpha olefin comprises at least one aryl group such that the at least one cross metathesis product comprises the at least one aryl group.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one aryl group such that the at least one cross metathesis product comprises the at least one aryl group.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one aryl group such that the at least one cross metathesis product comprises the at least one aryl group; and subjecting the at least one cross metathesis product comprising that at least one aryl group to conditions effective to promote olefin hydrogenation to form at least one hydrogenated cross metathesis product.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or alpha olefin comprises at least one aryl group such that the at least one cross metathesis product comprises the at least one aryl group; subjecting the at least one cross metathesis product comprising that at least one aryl group to conditions effective to promote olefin hydrogenation to form at least one hydrogenated cross metathesis product; and subjecting the at least one hydrogenated cross metathesis product to conditions effective to promote an aromatic sulfonation reaction to form at least one sulfonated cross metathesis product.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; and wherein that at least one olefinic substrate is selected from internal olefins, alpha olefins, or a combination thereof.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; and wherein the internal olefin or the alpha olefin comprises at least one functional group selected from hydroxyl or acyloxy such that the at least one cross metathesis product comprises the at least one functional group selected from hydroxyl or acyloxy.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or the alpha olefin comprises at least one functional group selected from hydroxyl or acyloxy such that the at least one cross metathesis product comprises the at least one functional group selected from hydroxyl or acyloxy; and subjecting the at least one cross metathesis product comprising the at least one functional group selected from hydroxyl or acyloxy to conditions effective to promote hydrogenation to form at least one hydrogenated cross metathesis product.

In another embodiment the present invention provides a method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising at least one hydrovinylated olefinic substrate, at least one cross metathesis substrate, and at least one olefin metathesis catalyst; subjecting the second composition to conditions effective to promote a cross metathesis reaction to form at least one cross metathesis product; wherein that at least one olefinic substrate is selected from internal olefins, alpha olefins, or a combination thereof; wherein the internal olefin or the alpha olefin comprises at least one functional group selected from hydroxyl or acyloxy such that the at least one cross metathesis product comprises the at least one functional group selected from hydroxyl or acyloxy; and subjecting the at least one cross metathesis product comprising the at least one functional group selected from hydroxyl or acyloxy to conditions effective to promote hydrogenation to form at least one hydrogenated cross metathesis product; and subjecting the at least one hydrogenated cross metathesis product to conditions effective to promote a sulfation reaction to form at least one sulfated cross metathesis product.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; and wherein the at least one olefinic substrate is selected from internal olefins, alpha olefins, or a combination thereof.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; and wherein the internal olefin or alpha olefin comprises at least one aryl group such that the at least one cross metathesis product comprises the at least one aryl group.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; wherein the internal olefin or alpha olefin comprises at least one aryl group such that the at least one cross metathesis product comprises the at least one aryl group; and subjecting the at least one cross metathesis product comprising the at least one aryl group to conditions effective to promote olefin hydrogenation to form at least one hydrogenated cross metathesis product.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; wherein the internal olefin or alpha olefin comprises at least one aryl group such that the at least one cross metathesis product comprises the at least one aryl group; subjecting the at least one cross metathesis product comprising the at least one aryl group to conditions effective to promote olefin hydrogenation to form at least one hydrogenated cross metathesis product; and subjecting the at least one hydrogenated cross metathesis product to conditions effective to promote an aromatic sulfonation reaction to form at least one sulfonated cross metathesis product.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; and wherein the at least one olefinic substrate is selected from internal olefins, alpha olefins, or a combination thereof.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; and wherein the internal olefin or the alpha olefin comprises at least one functional group selected from hydroxyl or acyloxy such that the at least one cross metathesis product comprises the at least one functional group selected from hydroxyl or acyloxy.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; wherein the internal olefin or the alpha olefin comprises at least one functional group selected from hydroxyl or acyloxy such that the at least one cross metathesis product comprises the at least one functional group selected from hydroxyl or acyloxy; and subjecting the at least one cross metathesis product comprising the at least one functional group selected from hydroxyl or acyloxy to conditions effective to promote olefin hydrogenation to form at least one hydrogenated cross metathesis product.

In another embodiment the present invention provides a method of making at least one cross metathesis product, the method comprising: forming a first composition comprising at least one olefinic substrate, at least one first hydrovinylation catalyst, and ethylene; subjecting the first composition to conditions effective to promote a first hydrovinylation reaction to form at least one hydrovinylated olefinic substrate; forming a second composition comprising at least one cross metathesis substrate, at least one second hydrovinylation catalyst, and ethylene; subjecting the second composition to conditions effective to promote a second hydrovinylation reaction to form at least one hydrovinylated cross metathesis substrate; forming a third composition comprising at least one hydrovinylated olefinic substrate, at least one hydrovinylated cross metathesis substrate, and at least one olefin metathesis catalyst; and subjecting the third composition to conditions effective to promote a cross metathesis reaction to form at least one cross metathesis product; wherein the at least one olefinic substrate is selected from internal olefins, alpha olefins, or a combination thereof; wherein the internal olefin or the alpha olefin comprises at least one functional group selected from hydroxyl or acyloxy such that the at least one cross metathesis product comprises the at least one functional group selected from hydroxyl or acyloxy; subjecting the at least one cross metathesis product comprising the at least one functional group selected from hydroxyl or acyloxy to conditions effective to promote olefin hydrogenation to form at least one hydrogenated cross metathesis product; and subjecting the at least one hydrogenated cross metathesis product to conditions effective to promote a sulfation reaction to form at least one sulfated cross metathesis product.

In another embodiment, the present invention provides compositions prepared by the methods of the present invention, where the methods are described herein.

In another embodiment, the present invention provides use of the compositions of the present invention.

In another embodiment, the present invention provides use of the compositions of the present invention, including but not limited to, use as fuels (e.g., diesel fuel and/or jet fuel), lubricants, surfactants, cosmetics, flavors, fragrances, polymers, plastic additives, home and personal care products, or as precursors for preparing such materials.

In another embodiment, the present invention provides for a method of performing a cross metathesis reaction, the method comprising contacting at least one first hydrovinylated cross metathesis substrate with at least one second hydrovinylated cross metathesis substrate in the presence of at least one olefin metathesis catalyst under metathesis conditions to form at least one cross metathesis product, wherein the at least one cross metathesis product may be optionally hydrogenated and/or optionally sulfonated and/or optionally sulfated, wherein the at least one first hydrovinylated cross metathesis substrate and the at least one second hydrovinylated cross metathesis substrate may be the same or different.

In another embodiment, the present invention provides for a method of performing a cross metathesis reaction, the method comprising contacting at least one first hydrovinylated olefinic substrate with at least one second hydrovinylated olefinic substrate in the presence of at least one olefin metathesis catalyst under metathesis conditions to form at least one cross metathesis product, wherein the at least one cross metathesis product may be optionally hydrogenated and/or optionally sulfonated and/or optionally sulfated, wherein the at least one first hydrovinylated olefinic substrate and the at least one second hydrovinylated olefinic substrate may be the same or different.

In another embodiment, the present invention provides a composition comprising:

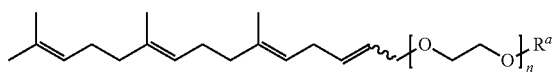

where $R^a$ is selected from the group consisting of H, acyl, or $SO_3Na$ and n ranges from 0-10 or preferably from 0-2, or is 0.

In another embodiment, the present invention provides a composition comprising:

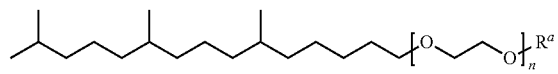

where $R^a$ is selected from the group consisting of H, acyl, or $SO_3Na$ and n ranges from 0-10 or preferably from 0-2 or is 0.

In another embodiment, the present invention provides a composition comprising:

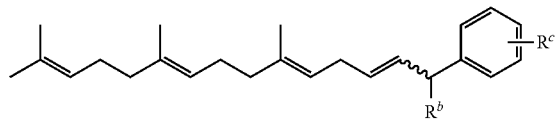

where $R^b$ is selected from H or Me, preferably Me, and $R^c$ is selected from the group consisting of H, Me, halogen or OH, preferably H or Me.

In another embodiment, the present invention provides a composition comprising:

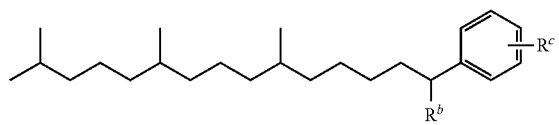

where $R^b$ is selected from H or Me, preferably Me, and $R^c$ is selected from the group consisting of H, Me, halogen or OH, preferably H or Me. In a further embodiment, the aryl ring is optionally sulfonated.

In another embodiment, the present invention provides a composition comprising:

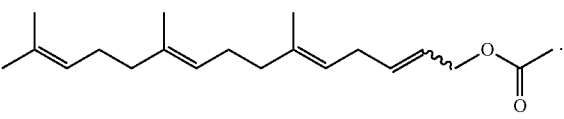 [SMILES: CC(=O)OCC=CC/C=C(\C)CC/C=C(\C)CCC=C(C)C]

In another embodiment, the present invention provides a composition comprising:

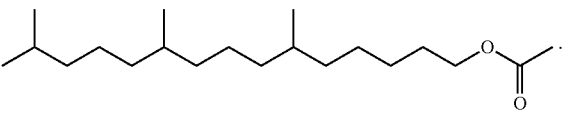 [SMILES: CC(=O)OCCCCCC(C)CCCC(C)CCCC(C)C]

In another embodiment, the present invention provides a composition comprising:

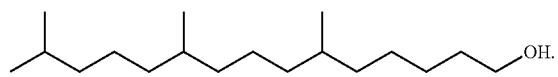 [SMILES: CC(C)CCCC(C)CCCC(C)CCCCCO]

In another embodiment, the present invention provides a composition comprising:

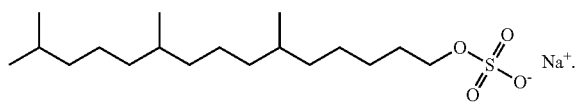 [SMILES: CC(C)CCCC(C)CCCC(C)CCCCCOS(=O)(=O)[O-]]

In another embodiment, the present invention provides a composition comprising:

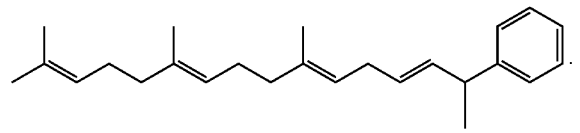 [SMILES: CC(C)=CCC/C(C)=C/CC/C(C)=C/C/C=C/C(C)c1ccccc1]

In another embodiment, the present invention provides a composition comprising:

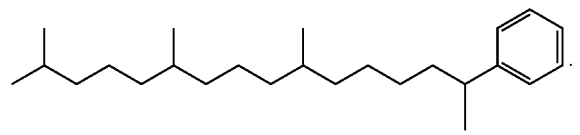 [SMILES: CC(C)CCCC(C)CCCC(C)CCCCC(C)c1ccccc1]

In another embodiment, the present invention provides a composition comprising:

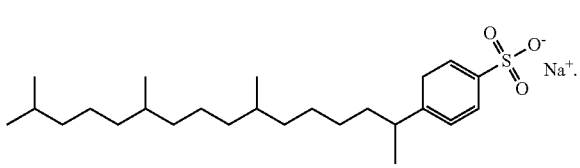 [SMILES: CC(C)CCCC(C)CCCC(C)CCCCC(C)C1=C=CC(S(=O)(=O)[O-])=CC1]

In another embodiment, the present invention provides a composition comprising:

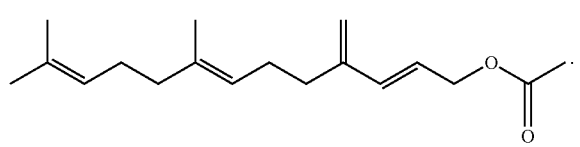 [SMILES: C=C(/C=C/COC(C)=O)CC/C=C(\C)CCC=C(C)C]

In another embodiment, the present invention provides a composition comprising:

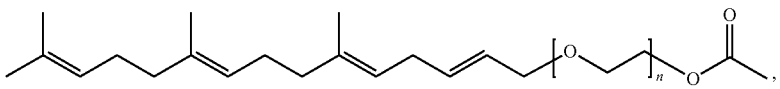

wherein n is 1 or 2.

In another embodiment, the present invention provides a composition comprising:

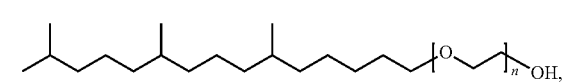

wherein n is 1 or 2.

In another embodiment, the present invention provides a composition comprising:

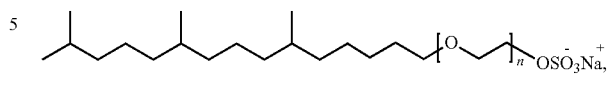

wherein n is 1 or 2.

In another embodiment, the present invention provides a method of making a composition comprising:

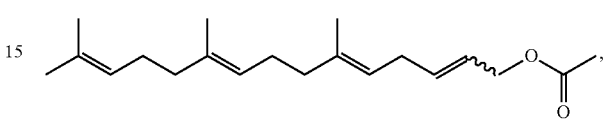

where the method is described herein. In another embodiment, the present invention provides a method of making a composition comprising:

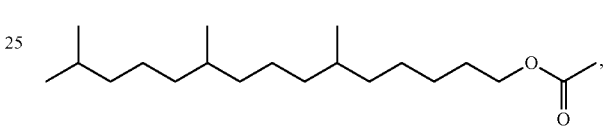

where the method is described herein.

In another embodiment, the present invention provides a method of making a composition comprising:

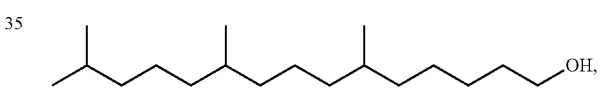

where the method is described herein.

In another embodiment, the present invention provides a method of making a composition comprising:

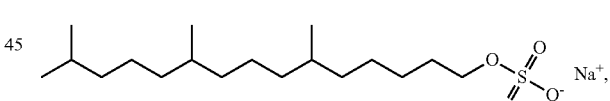

where the method is described herein.

In another embodiment, the present invention provides a method of making a composition comprising:

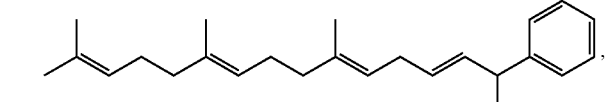

where the method is described herein.

In another embodiment, the present invention provides a method of making a composition comprising:

[structure: branched alkyl chain with phenyl terminus]

where the method is described herein.

In another embodiment, the present invention provides a method of making a composition comprising:

[structure: branched alkyl chain with para-sulfonate phenyl group, Na+]

where the method is described herein.

In another embodiment, the present invention provides a method of making a composition comprising:

[structure: farnesyl acetate]

where the method is described herein.

In another embodiment, the present invention provides a method of making a composition comprising:

[structure: branched farnesene-derived chain with -(O-CH$_2$CH$_2$)$_n$-O-C(=O)- group]

wherein n is 1 or 2, where the method is described herein.

In another embodiment, the present invention provides a method of making a composition comprising:

[structure: branched alkyl chain with -(O-CH$_2$CH$_2$)$_n$-OH]

wherein n is 1 or 2, where the method is described herein.

In another embodiment, the present invention provides a method of making a composition comprising:

[structure: branched alkyl chain with -(O-CH$_2$CH$_2$)$_n$-OSO$_3^-$Na$^+$]

wherein n is 1 or 2, where the method is described herein.

These and other aspects and embodiments of the present invention will be apparent to the skilled artisan in light of the following detailed description and examples.

BRIEF DESCRIPTION OF THE DRAWINGS

FIG. 1 Chemical structures of hydrovinylation catalysts HV-1 to HV-16.

FIG. 2 $^1$H NMR of (4E,8E)-5,9,13-trimethyltetradeca-1,4,8,12-tetraene (hydrovinylated farnesene) in CDCl$_3$.

FIG. 3 $^{13}$C NMR of (4E,8E)-5,9,13-trimethyltetradeca-1,4,8,12-tetraene (hydrovinylated farnesene) in CDCl$_3$.

FIG. 4: $^1$H NMR of 3-phenyl-1-butene in CDCl$_3$.

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl (Ph), naphthyl, biphenyl, diphenylether, diphenylamine, benzophenone, and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkynyl wherein "alkyl," "aryl", "aralkyl", "alkaryl", "alkenyl", and "alkynyl" are as defined above. The acetoxy group (—O(CO)CH$_3$; often abbreviated as OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a fluoro, chloro, bromo, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

The term "heterocyclic carbene" refers to a neutral electron donor ligand comprising a carbene molecule, where the carbenic carbon atom is contained within a cyclic structure and where the cyclic structure also contains at least one heteroatom. Examples of heterocyclic carbenes include "N-heterocyclic carbenes" wherein the heteroatom is nitrogen and "P-heterocyclic carbenes" wherein the heteroatom is phosphorus.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—NH$_2$), cyano(—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H) alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^-$)$_2$), phosphinato (—P(O)(O$^-$)), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

The term "ethenolysis" refers to the cross metathesis of a substrate with ethylene. For example, ethenolysis of methyl oleate produces methyl 9-decenoate and 1-decene. For ethenolysis references see Burdett, K. A.; Harris, L. D.; Margl, P.; Maughon, B. R.; Mokhtar-Zadeh, T.; Saucier, P. C.; Wasserman, E. P. *Organometallics* 2004, 23, 2027; Nickel, A.; Ung, T., Mkrtumyan, G., Uy, J., Lee, C. H., Stoianova, D., Papazian, J., Wei, W.-H., Mallari, A., Schrodi, Y., Pederson, R. L. *Topic in Catalysis*, 2012, 55, 518-523; Warwel, S.; Briise, F.; Demes, C.; Kunz, M.; Rüsch gen. Klaas M., *Chemosphere* 2001, 43, 39; Anderson, D. R.; Ung, T.; Mkrtumyan, G.; Bertrand, G.; Grubbs, R. H.; Schrodi, Y. *Organometallics* 2008, 27, 563; Schrodi, Y.; Ung, T.; Vargas, A.; Mkrtumyan, G.; Lee, C. W.; Champagne, T. M.; Pederson, R. L.; Hong, S. H. *Clean—Soil, Air, Water* 2008, 36, 669.

The term "alkenolysis" refers to a cross metathesis reaction where a terminal olefin is used in a cross metathesis reaction with an internal double bond to produce different terminal olefins, where the initial terminal olefin cannot be ethylene. For example alkenolysis of methyl oleate with 1-butene produces methyl 9-decenoate, 1-decene, methyl-9-dodecenoate and 3-dodecene. For alkenolysis references see Schrodi, Y.; Pederson, R. L.; Kaido, H.; Tupy, M. J. US Pat. App. 2010/0145086, assigned to Elevance Renewable Sciences, Inc; and Nickel, A.; Ung, T., Mkrtumyan, G., Uy, J., Lee, C. H., Stoianova, D., Papazian, J., Wei, W.-H., Mallari, A., Schrodi, Y., Pederson, R. L. *Topic in Catalysis*, 2012, 55, 518-523, are incorporated by reference.

Optional" or "optionally" means that the subsequently described circumstance may or may not occur, so that the description includes instances where the circumstance occurs and instances where it does not. For example, the phrase "optionally substituted" means that a nonhydrogen substituent may or may not be present on a given atom, and, thus, the description includes structures wherein a nonhydrogen substituent is present and structures wherein a nonhydrogen substituent is not present.

The term "terpene" refers to cyclic or acyclic unsaturated hydrocarbons built up from units of isoprene linked together in various ways. The terms "terpenoid", "isoprenoid" and "isoprenoid compound" are used interchangeably herein and refer to functionalized compounds derivable from terpenes. Biosynthesis of terpenes generally involves the terpenoid isopentenyl diphosphate as an intermediate.

The terms "2-$C_4$ to 20-$C_{40}$" refers to a short hand method of naming olefins. The first number represents the position of the double bond and the number after carbon represents the number of carbons on the chain. For example, 2-$C_4$ stand for 2-butene, 3-$C_6$ stands for 3-hexene, up to 20-$C_{40}$ stands for 20-tetracontene.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn. If an olefinic structure is depicted which could potentially exist in either cis (Z) or trans (E) configuration, the use of a wavy line in the depiction indicates that the configuration may be either cis or trans or a combination of the two:

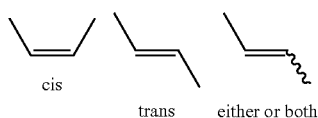

Cross Metathesis Substrates

Cross metathesis substrates for use with the present invention are generally known a poly-branched poly-olefins.

One class of poly branched poly-olefins for use with the present invention include terpenes such as monoterpenes, sesquiterpenes, diterpenes, sesterterpenes, triterpenes, tetraterpenes, and polyterpenes. One class of sesquiterpenes for use with the present invention are commonly known as farnesene(s). Farnesene(s) for use with the present invention are disclosed herein as follows. The farnesene can be derived from any known source or prepared by any method known to a skilled artisan. In some embodiments, the farnesene is derived from a chemical source (e.g., petroleum or coal) or obtained by a chemical synthetic method. In other embodiments, the farnesene is prepared by fractional distillation or petroleum or coal tar. In further embodiments, the farnesene is prepared by any known chemical or synthetic method. One non-limiting example of suitable chemical includes dehydrating nerolidol with phosphoryl chloride in pyridine as described in the article by Anet E. F. L. J., "Synthesis of (E,Z)-α-,(Z,Z)-α-, and (Z)-β-farnesene," Aust. J. Chem. 23(10), 2101-2108 (1970), which is incorporated herein by reference.

In some embodiments, the farnesene can be obtained or derived from naturally occurring terpenes that can be produced by a wide variety of plants, such as Copaifera langsdorfii, conifers, and spurges; insects, such as swallowtail butterflies, leaf beetles, termites, and pine sawflies; and marine organisms, such as algae, sponges, corals, mollusks, and fish.

Copaifera langsdorfii or Copaifera tree is also known as the diesel tree and kerosene tree. It has many names in local languages, including kupa'y, cabismo, and copauva. Copaifera tree may produce a large amount of terpene hydrocarbons in its wood and leaves. Generally, one Copaifera tree can produce from about 30 to about 40 liters of terpene oil per year.

Terpene oils can also be obtained from conifers and spurges. Conifers belong to the plant division Pinophyta or Coniferae and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces, and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

The farnesene is a sesquiterpene which are part of a larger class of compound called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, the farnesene can be isolated or derived from terpene oils for use in the present invention.

In certain embodiments, the farnesene is derived from a biological source. In other embodiments, the farnesene can be obtained from a readily available, renewable carbon source. In further embodiments, the farnesene is prepared by contacting a cell capable of making farnesene with a carbon source under conditions suitable for making the farnesene.

Any carbon source that can be converted into one or more isoprenoid compounds can be used herein. In some embodiments, the carbon source is a sugar or a non-fermentable carbon source. The sugar can be any sugar known to those of skill in the art. In certain embodiments, the sugar is a monosaccharide, disaccharide, polysaccharide or a combination thereof. In other embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose and combinations thereof. In still other embodiments, the simple sugar is sucrose. In certain embodiments, the bioengineered fuel component can be obtained from a polysaccharide. Some non-limiting examples of suitable polysaccharides include starch, glycogen, cellulose, chitin and combinations thereof.

The sugar suitable for making the farnesene can be found in a wide variety of crops or sources. Some non-limiting examples of suitable crops or sources include sugar cane, bagasse, *miscanthus*, sugar beet, sorghum, grain sorghum, switchgrass, barley, hemp, kenaf, potatoes, sweet potatoes, cassaya, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn. In other embodiments, the sugar source is cane juice or molasses.

A non-fermentable carbon source is a carbon source that cannot be converted by the organism into ethanol. Some non-limiting examples of suitable non-fermentable carbon sources include acetate and glycerol.

In certain embodiments, the farnesene can be prepared in a facility capable of biological manufacture of $C_{15}$ isoprenoids. The facility can comprise any structure useful for preparing the $C_{15}$ isoprenoids, such as α-farnesene, β-farnesene, nerolidol or farnesol, using a microorganism. In some embodiments, the biological facility comprises one or more of the cells disclosed herein. In other embodiments, the biological facility comprises a cell culture comprising at least a $C_{15}$ isoprenoid in an amount of at last about 1 wt. %, at least about 5 wt. %, at least about 10 wt. %, at least about 20 wt. %, or at least about 30 wt. %, based on the total weigh of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises cell culture capable of biologically manufacturing farnesyl pyrophosphate (FPP). In further embodiments, the fermentor comprises a cell culture capable of biologically manufacturing isopentenyl diphosphate (IPP). In certain embodiments, the fermentor comprises a cell culture comprising at least a $C_{15}$ isoprenoid in an amount of at least about 1 wt. %, at least about 5 wt. %, at least about 10 wt. %, at least about 20 wt. %, or at least about 30 wt. %, based on the total weight of the cell culture.

The facility can further comprise any structure capable of manufacturing the fuel component or fuel additive from the $C_{15}$ isoprenoid, such as α-farnesene, β-farnesene, nerolidol or farnesol. The structure may comprise a reactor for dehydrating the nerolidol or farnesol to α-farnesene or β-farnesene. Any reactor that can be used to convert an alcohol into an alkene under conditions known to skilled artisans may be used herein. The reactor may comprise a dehydrating catalyst disclosed herein. In some embodiments, the structure further comprises a mixer, a container, and a mixture of the dehydrating products from the dehydrating step.

The biosynthetic process of making $C_{15}$ isoprenoid compounds are disclosed in U.S. Pat. No. 7,399,323; U.S. Application No. US 2008/0274523; and PCT Publication Nos. WO 2007/140339 and WO 2007/139924, which are incorporated herein by reference.

α-Farnesene, whose structure is

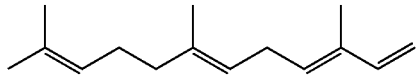

is found in various biological sources including, but not limited to, Dufour's gland in ants, and in the coating of apple and pear peels. Biochemically, α-farnesene is made from FPP by α-farnesene synthase. Some non-limiting examples of suitable nucleotide sequences that encode such an enzyme include (DQ309034; *Pyrus communis* cultivar d'Anjou) and (AY 182241; *Malus domestica*). See Pechoous et al., Planta 219(1):84-94 (2004).

β-farnesene, whose structure is

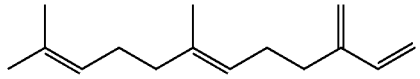

is found in various biological sources including, but not limited to, aphids and essential oils such as peppermint oil. In some plants such as wild potatoe, β-farnesene is synthesized as a natural insect repellant. Biochemically, β-farnesene is made from FPP by β-farnesene synthase. Some non-limiting examples of suitable nucleotide sequences that encode such an enzyme include (AF024615: Menthaxpiperita) and (AY8355398; *Artemisia annua*). See Picaud et al., Phytochemistry 66(9): 961-967 (2005). β-farnesene is commercially available from Amyris Inc. and is sold under the trade name Biofene™. Biofene™ is manufactured from sugarcane feedstock.

Farnesol, whose structure is

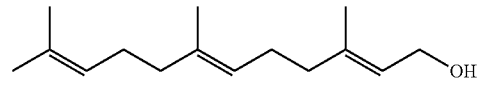 [SMILES: CC(C)=CCC/C(C)=C/CC/C(C)=C/CO]

is found in various biological sources including insects and essential oils from cintronella, neroli, cyclamen, lemon grass, tuberose, and rose. Biochemically, farnesol is made from FPP by a hydroxylase such as farnesol synthase. Some non-limiting examples of suitable nucleotide sequences that encode such an enzyme include: (AF529266; *Zea mays*) and (YDR481C; *Saccharomyces cerevisiae*). See Song, L., Applied Biochemistry and Biotechnology 128:149-158 (2006).

Nerolidol, whose structure is

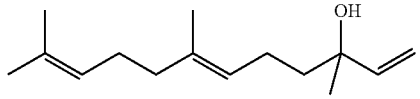 [SMILES: C=CC(C)(O)CC/C=C(\C)CCC=C(C)C]

is also known as peruviol which is found in various biological sources including essential oils from neroli, ginger, jasmine, lavender, tea tree, and lemon grass. Biochemically, nerolidol is made from FPP by a hydroxylase such as nerolidol synthase. A non-limiting example of a suitable nucleotide sequence that encodes such an enzyme includes AF529266 from *Zea mays* (maize; gene tps 1).

The farnesol and nerolidol disclosed herein may be converted into α-farnesene, β-farnesene or a combination thereof by dehydration with a dehydrating agent or an acid catalyst. Any dehydrating agent or an acid catalyst that can convert an alcohol into an alkene can be used herein. Some non-limiting examples of suitable dehydrating agents or acid catalysts include phosphoryl chloride, anhydrous zinc chloride, phosphoric acid and sulfuric acid.

Additional non-limiting examples of poly-branched polyolefins for use with the present invention include the following:

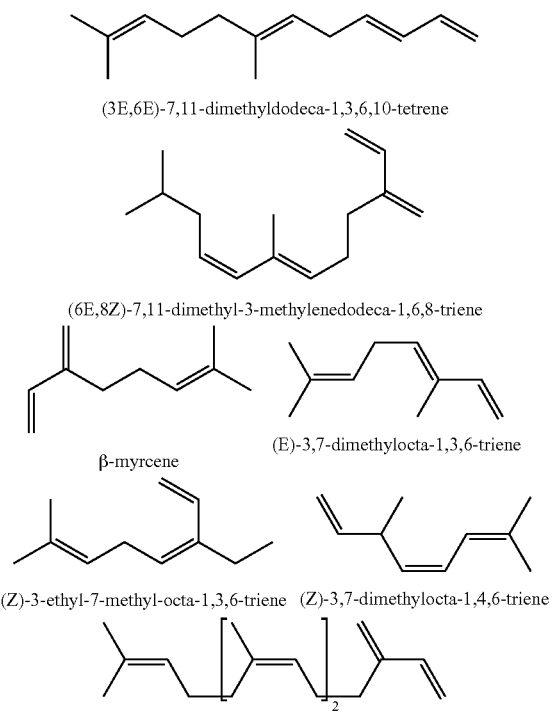

Preferred cross metathesis substrates include farnesenes, α-farnesene, β-farnesene, (3E,6E)-7,11-dimethyldodeca-1,3,6,10-tetrene, (6E,8Z)-7,11-dimethyl-3-methylenedodeca-1,6,8-triene, β-myrcene, (E)-3,7-dimethylocta-1,3,6-triene, (Z)-3-ethyl-7-methyl-octa-1,3,6-triene, (Z)-3,7-dimethyl-octa-1,4,6-triene. More preferred cross metathesis substrates include farnesenes, α-farnesene, β-farnesene, β-myrcene, and (Z)-3,7-dimethylocta-1,4,6-triene. Most preferred cross metathesis substrates include β-farnesene, and β-myrcene.

Olefinic Substrates

Olefinic substrates for use with the present invention include any olefin metathesis active compound containing at least one carbon-carbon double bond. Olefinic substrates for use with the present invention may be derived from petroleum sources, fermentation processes, or from natural sources such as oils extracted from plants or animals. Non-limiting examples of such petroleum-derived olefinic feedstocks include alpha-olefins, substituted alpha olefins, internal olefins, substituted internal olefins and cyclic or polycyclic olefins such as, for example, DCPD (dicyclopentadiene), norbornenes, and substituted norbornenes. Non-limiting examples of fermentation-derived olefinic feedstocks include fumarates, isobutylene, and various fatty acids and/or esters. Non-limiting examples of olefinic substrates derived from natural sources include but are not limited to natural rubbers, terpenes and other isoprenoids including citronellene, linalool, myrcene, β-pinenes, pyrethrins, steroids, estolides, alkylresorcinols, cardanol, and fatty alcohols. Other non-limiting examples of olefinic substrates derived from natural sources include various unsaturated and polyunsaturated triglyceride-based oils extracted from plants or animals. Such oils include without limitation natural seed oils, such as soybean oil (SBO), camelina oil, sunflower oil, canola oil, safflower oil, cottonseed oil, castor oil, rapeseed oil, peanut oil, corn oil, olive oil, palm oil, sesame oil, grape seed oil, and the fatty acid methyl esters derived therefrom. Such oils also include animal oils such as fish oils and tallow.

Other non-limiting olefinic substrates for use with the present invention include substituted and non-substituted styrenic compounds, substituted and non-substituted styrene, substituted and non-substituted divinylbenzene, substituted and non-substituted allylbenzene, substituted and non-substituted 4-phenyl-1-butene, alpha-methyl styrene, sulfonated alpha-methyl styrene, 3-phenyl-1-butene, and sulfonated 3-phenyl-1-butene.

The term "internal olefin" as used herein means an olefin wherein each of the olefinic carbons is substituted by at least one non-hydrogen substituent. The non-hydrogen substituents are selected from hydrocarbyl, and substituted hydrocarbyl, heteroatom-containing hydrocarbyl, substituted heteroatom-containing hydrocarbyl, alkyl, substituted alkyl, aryl, substituted aryl, heteroalkyl, heteroaryl, alkoxy, alkylene, alkenyl, alkenylene, alkynyl, alkynylene, aryloxy, alkaryl, acyl and functional groups. The internal olefin is therefore at least disubstituted, and may further include additional non-hydrogen substituents such that the internal olefin is tri- or tetra-substituted. Each of the substituents on the internal olefinic carbons may be further substituted as described herein. The internal olefin may be in the Z- or E-configuration.

The internal olefin may be a single compound or a mixture of compounds. The internal olefin may comprise a single internal olefin or a plurality of internal olefins. A mixture of internal olefins may be used. The internal olefin may be hydrophobic or hydrophilic, although in a preferred embodiment, the internal olefin is hydrophobic.

For example, the internal olefin may be represented by the formula $(R^I)(R^{II})C=C(R^{III})(R^{IV})$, wherein $R^I$, $R^{II}$, $R^{III}$, and $R^{IV}$ are independently selected from H, hydrocarbyl, and substituted hydrocarbyl, provided that at least one of $R^I$ and $R^{II}$ and at least one of $R^{III}$ and $R^{IV}$ is other than H. In a preferred embodiment, either $R^I$ or $R^{II}$ and either $R^{III}$ or $R^{IV}$ is H, such that the internal olefin is di-substituted.

Examples of internal di-substituted olefins may be represented by the formula $(R^I)(R^{II})C=C(R)(R^{IV})$, wherein $R^I$, $R^{II}$, $R^{III}$, and $R^{IV}$ are independently selected from H, $C_1$ to $C_{20}$ alkyl, and substituted $C_1$ to $C_{20}$ alkyl, provided that at least one of $R^I$ and $R^{II}$ and at least one of $R^{III}$ and $R^{IV}$ is other than H. In a preferred embodiment, either $R^I$ or $R^{II}$ and either $R^{III}$ or $R^{IV}$ is H, such that the internal olefin is di-substituted.

Examples of internal di-substituted olefins where $R^I$ and $R^{III}$ are the same and $R^{II}$ and $R^{IV}$ are the same and where $R^I$ and $R^{III}$ are H and $R^{II}$ and $R^{IV}$ are other than H and the same may be represented by the formula $(R^I)(R^{II})C=C(R^{III})(R^{IV})$, include, without limitation, 2-butene (represented as $2\text{-}C_4$) to 20-tetracontene (represented as $20\text{-}C_{40}$), and substituted $2\text{-}C_4$ (2-butene) to $20\text{-}C_{40}$ (20-tetracontene). Preferred di-substituted internal olefins include 2-$C_4$ to 5-$C_{10}$ and substituted 2-$C_4$ to 5-$C_{10}$.

Additionally, the internal olefin may be represented by the formula $(R^I)(R^{II})C=C(R^{III})(R^{IV})$, wherein $R^I$, $R^{II}$, $R^{III}$, and $R^{IV}$ are independently selected from hydrogen, hydrocarbyl, substituted hydrocarbyl, heteroatom-containing hydrocarbyl, substituted heteroatom-containing hydrocarbyl, alkyl, substituted alkyl, aryl, substituted aryl, heteroalkyl, heteroaryl, alkoxy, alkylene, alkenyl, alkenylene, alkynyl, alkynylene, aryloxy, alkaryl, acyl, and functional groups, provided that at least one of $R^I$ and $R^{II}$ and at least one of $R^{III}$ and $R^{IV}$ is other than hydrogen. In a preferred embodiment, either $R^I$ or $R^{II}$ and either $R^{III}$ or $R^{IV}$ is H, such that the internal olefin is di-substituted.

The term "alpha olefin" as used herein refers to organic compounds which are terminal olefins or alkenes with a chemical formula RR'C=$CH_2$, where R and R' are each independently H, hydrocarbyl, substituted hydrocarbyl, alkyl, substituted alkyl, aryl, substituted aryl, heteroalkyl, heteroaryl, alkoxy, alkylene, alkenyl, alkenylene, alkynyl, alkynylene, aryloxy, alkaryl, acyl, heteroatom-containing hydrocarbyl, substituted heteroatom-containing hydrocarbyl, functional groups and R and R' are not both H.

Olefinic substrates for use with the present invention may comprise a single olefinic substrate or a plurality of olefinic substrates.

It will be appreciated by those of skill in the art that the use of olefinic substrates containing, for example, long alkyl substituents enables liquid-phase, room temperature (or greater) reactions and/or the use of reactors working at near atmospheric or slightly higher pressures.

In some preferred embodiments, the cross metathesis substrate is soluble in the olefinic substrate. The cross metathesis substrate may have a solubility of at least 0.25 M, at least 1 M, at least 3 M, or at least 5 M in the olefinic substrate. The cross metathesis substrate and the olefinic substrate may also be miscible at all concentrations.

As another example, the cross metathesis substrate has a low solubility in the olefinic substrate, and the cross metathesis reaction occurs as an interfacial reaction. It should be noted that, when one or more of the reactants is solid or gaseous, the reactions may still be carried out in the liquid phase by dissolving any solid or gaseous reactants in the liquid reactants, or by employing a solvent, as described herein.

The olefinic substrate and/or cross metathesis substrate may be provided in the form of a gas. Typically, the pressure of a gaseous cross-metathesis partner over the reaction solution is maintained in a range that has a minimum of about 10 psig, 15 psig, 50 psig, or 80 psig, and a maximum of about 250 psig, 200 psig, 150 psig, or 130 psig. Embodiments wherein the reaction pressures are lowered till near atmospheric pressure and in particular till pressures slightly above atmospheric allow for a reduction in equipment costs compared to embodiments performed at high pressure (e.g. pressures greater than 250 psi).

The olefin metathesis reactions (e.g. cross metathesis) of the disclosure are catalyzed by any of the metathesis catalysts that are described herein. The catalyst is typically added to the reaction medium as a solid, but may also be added as a solution wherein the catalyst is dissolved in an appropriate solvent. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of the olefinic substrate. Catalyst loading, when measured in ppm relative to the amount of the olefinic substrate, is calculated using the equation $$\text{ppm catalyst} = \frac{\text{moles catalyst}}{\text{moles olefinic substrate double bonds}} * 1{,}000{,}000$$

$$\text{mol \% catalyst} = \frac{\text{moles catalyst}}{\text{moles olefinic substrate double bonds}} * 100$$

Alternatively, the amount of catalyst can be measured in terms of mol % relative to the amount of olefinic substrate, using the equation Thus, the catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

In a preferred embodiment, the reactions of the disclosure are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions of the disclosure may also be carried out in an oxygen-containing and/or a water-containing atmosphere, and in one embodiment, the reactions are carried out under ambient conditions. The presence of oxygen, water, or other impurities in the reaction may, however, necessitate the use of higher catalyst loadings as compared with reactions performed under an inert atmosphere.

Preferred olefinic substrates include 3-phenyl-1-butene, sulfonated 3-phenyl-1-butene, 3-tolyl-1-butene, sulfonated 3-tolyl-1-butene, alpha-methyl styrene, styrene, 1,4-diacetoxy-2-butene, allylacetate, 2-butene-1,4-diol, allyl alcohol, farnesene, hydrovinylated farnesene (self-metathesis), myrcene, ethyl acrylate, methyl acrylate, methyl crotonate, 2-(allyloxy)ethyl acetate, 2-(allyloxy)ethanol, methyl 9-decenoate, and methyl 9-dodecenoate. More preferred olefinic substrates include 3-phenyl-1-butene, 3-tolyl-1-butene, alpha-methyl styrene, styrene, 1,4-diacetoxy-2-butene, allyl acetate, farnesene, hydrovinylated farnesene (self-metathesis), myrcene, ethyl acrylate, methyl acrylate, methyl crotonate, 2-(allyloxy)ethyl acetate, methyl 9-decenoate, and methyl 9-dodecenoate. Most preferred olefinic substrates include 3-phenyl-1-butene, 3-tolyl-1-butene, styrene, 1,4-diacetoxy-2-butene, allyl acetate, hydrovinylated farnesene (self-metathesis), ethyl acrylate, methyl acrylate, methyl crotonate, 2-(allyloxy)ethyl acetate, methyl 9-decenoate, and methyl 9-dodecenoate.

Olefin Metathesis Catalysts

Olefin metathesis catalysts suitable for use with the present invention are disclosed herein. These olefin metathesis catalysts may be used to perform olefin metathesis reactions including without limitation cross metathesis (CM), self-metathesis, ethenolysis, alkenolysis, and combinations thereof.

An olefin metathesis catalyst according to the invention, is preferably a Group 8 transition metal complex having the structure of formula (I)

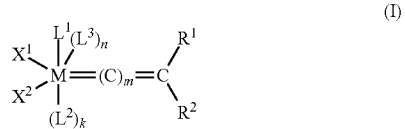

in which:

M is a Group 8 transition metal;

$L^1$, $L^2$, and $L^3$ are neutral electron donor ligands;

n is 0 or 1, such that $L^3$ may or may not be present;

m is 0, 1, or 2;

k is 0 or 1;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Additionally, in formula (I), one or both of $R^1$ and $R^2$ may have the structure —$(W)_n$—$U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety.

Preferred catalysts contain Ru or Os as the Group 8 transition metal, with Ru particularly preferred.

Numerous embodiments of the catalysts useful in the reactions disclosed herein are described in more detail infra. For the sake of convenience, the catalysts are described in groups, but it should be emphasized that these groups are not meant to be limiting in any way. That is, any of the catalysts useful in the invention may fit the description of more than one of the groups described herein.

A first group of catalysts, then, are commonly referred to as First Generation Grubbs-type catalysts, and have the structure of formula (I). For the first group of catalysts, M is a Group 8 transition metal, m is 0, 1, or 2, and n, k, $X^1$, $X^2$, $L^1$, $L^2$, $L^3$, $R^1$, and $R^2$ are described as follows.

For the first group of catalysts, n is 0 or 1, k is 0 or 1, and $L^1$ and $L^2$ are independently selected from phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$ where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred, $L^1$ and $L^2$ are independently selected from the group consisting of trimethylphosphine (PMe$_3$), triethylphosphine (PEt$_3$), tri-n-butylphosphine (PBu$_3$), tri(ortho-tolyl)phosphine (P-o-tolyl$_3$), tri-tert-butylphosphine (P-tert-Bu$_3$), tricyclopentylphosphine (PCp$_3$), tricyclohexylphosphine (PCy$_3$), triisopropylphosphine (P-i-Pr$_3$), tri-sec-butylphosphine, trioctylphosphine (POct$_3$), triisobutylphosphine, (P-i-Bu$_3$), triphenylphosphine (PPh$_3$), tri(pentafluorophenyl)phosphine (P(C$_6$F$_5$)$_3$), methyldiphenylphosphine (PMePh$_2$), dimethylphenylphosphine (PMe$_2$Ph), and diethylphenylphosphine (PEt$_2$Ph).

Alternatively, $L^1$ and $L^2$ may be independently selected from phosphabicycloalkane (e.g. monosubstituted 9-phosphabicyclo-[3.3.1]nonane, or monosubstituted 9-phosphabicyclo[4.2.1]nonane] such as cyclohexylphoban, isopropylphoban, ethylphoban, methylphoban, butylphoban, pentylphoban and the like).

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, NO$_3$, —N═C═O, —N═C═S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, CF$_3$CO$_2$, CH$_3$CO$_2$, CFH$_2$CO$_2$, (CH$_3$)$_3$CO, (CF$_3$)$_2$(CH$_3$)CO, (CF$_3$)(CH$_3$)$_2$CO, PhO, MeO, EtO, tosylate, mesylate, or trifluoromethanesulfonate (CF$_3$SO$_3$ or commonly abbreviated as OTf). In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —CH═C(CH$_3$)$_2$.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as Second Generation Grubbs-type catalysts, have the structure of formula (I), wherein $L^1$ is a carbene ligand having the structure of formula (II)

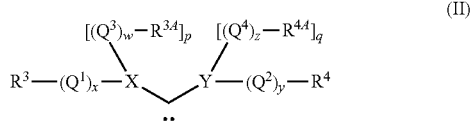

such that the complex may have the structure of formula (III)

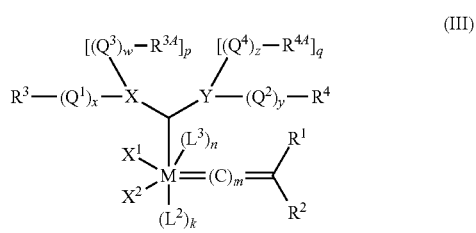

wherein M, m, n, k, $X^1$, $X^2$, $L^2$, $L^3$, $R^1$, and $R^2$ are as defined for the first group of catalysts, and the remaining substituents are as follows;

X and Y are heteroatoms typically selected from N, O, S, and P. Since O and S are divalent, p is necessarily zero when X is O or S, q is necessarily zero when Y is O or S. However, when X is N or P, then p is 1, and when Y is N or P, then q is 1. In a preferred embodiment, both X and Y are N;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero.

Further, two or more substituents on adjacent atoms within $Q^1$, $Q^2$, $Q^3$, and $Q^4$ may be linked to form a cyclic group; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl. In addition, X and Y may be independently selected from carbon and one of the heteroatoms mentioned above, preferably no more than one of X or Y is carbon. Also, $L^2$ and $L^3$ may be taken together to form a single bidentate electron-donating ligand. Furthermore, $R^1$ and $R^2$ may be taken together to form an indenylidene moiety. Moreover, $X^1$, $X^2$, $L^2$, $L^3$, X and Y may be further coordinated to boron or to a carboxylate.

In addition, any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $Q^3$, and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support. Any two or more of $X^1$, $X^2$, $L^1$, $L^2$, $L^3$, $R^1$, $R^2$, $R^3$, $R^{3A}$, $R^4$, and $R^{4A}$ can also be taken to be -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

A particular class of carbene ligands having the structure of formula (II), where $R^{3A}$ and $R^{4A}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC) ligands.

Preferably, $R^{3A}$ and $R^{4A}$ are linked to form a cyclic group so that the carbene ligand has the structure of formula (IV)

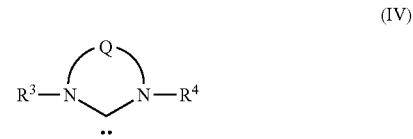

wherein $R^3$ and $R^4$ are as defined for the second group of catalysts above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands suitable as $L^1$ thus include, but are not limited to, the following where DIPP or DiPP is diisopropylphenyl and Mes is 2,4,6-trimethylphenyl:

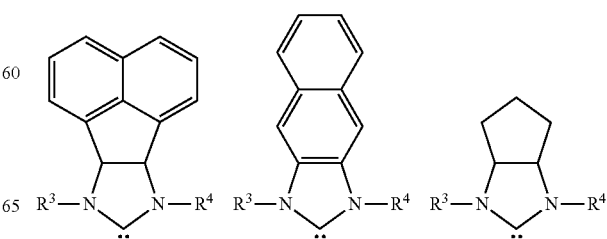

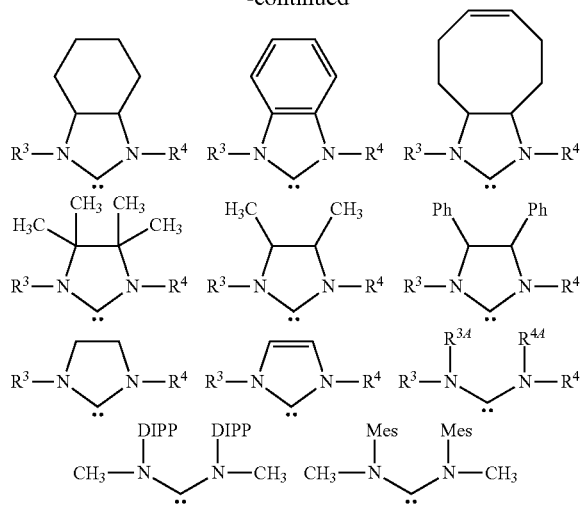

Additional examples of N-heterocyclic carbene (NHC) ligands and acyclic diaminocarbene ligands suitable as L¹ thus include, but are not limited to the following:

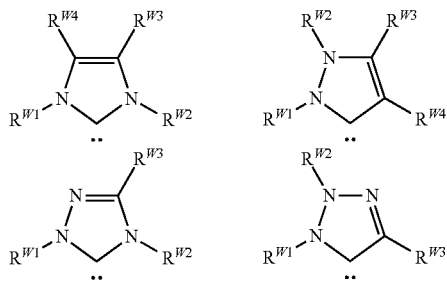

wherein $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halogen, nitro, amido, carboxyl, alkoxy, aryloxy, sulfonyl, carbonyl, thio, or nitroso groups.

Additional examples of N-heterocyclic carbene (NHC) ligands suitable as L¹ are further described in U.S. Pat. Nos. 7,378,528; 7,652,145; 7,294,717; 6,787,620; 6,635,768; and 6,552,139 the contents of each are incorporated herein by reference.

Additionally, thermally activated N-Heterocyclic Carbene Precursors as disclosed in U.S. Pat. No. 6,838,489, the contents of which are incorporated herein by reference, may also be used with the present invention.

When M is ruthenium, then, the preferred complexes have the structure of formula (V)

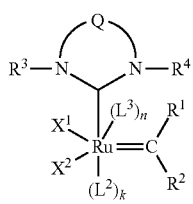

(V)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include, without limitation, carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen.

When $R^3$ and $R^4$ are aromatic, they are typically, although not necessarily, composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e. Mes as defined herein).

In a third group of catalysts having the structure of formula (I), M, m, n, k, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substituent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, $L^2$ and $L^3$ may also be taken together to form a bidentate or multidentate ligand containing two or more, generally two, coordinating heteroatoms such as N, O, S, or P, with preferred such ligands being diimine ligands. One representative bidentate ligand has the structure of formula (VI)

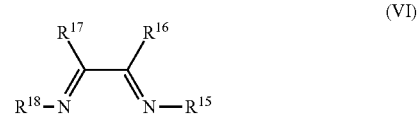

(VI)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As (Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N (CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph) (CH$_2$)$_2$CO$_2$, phthalocyanines, and porphyrins.

Complexes wherein Y is coordinated to the metal are examples of a fifth group of catalysts, and are commonly called "Grubbs-Hoveyda" catalysts. Grubbs-Hoveyda metathesis-active metal carbene complexes may be described by the formula (VII)

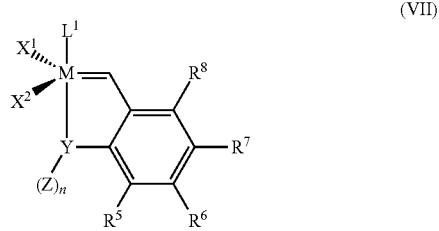

(VII)

wherein,

M is a Group 8 transition metal, particularly Ru or Os, or, more particularly, Ru;

$X^1$, $X^2$, and $L^1$ are as previously defined herein for the first and second groups of catalysts;

Y is a heteroatom selected from nil, N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $X^2$, $L^1$, Y, Z, $R^5$, $R^6$, $R^7$, and $R^8$ may be linked to a support. Additionally, $R^5$, $R^6$, $R^7$, $R^8$, and Z may independently be thioisocyanate, cyanato, or thiocyanato.

Examples of complexes comprising Grubbs-Hoveyda ligands suitable in the invention include:

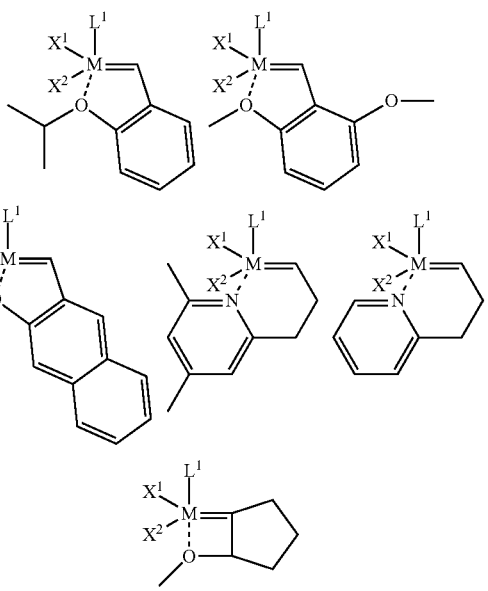

wherein, $L^1$, $X^1$, $X^2$, and M are as described for any of the other groups of catalysts. Suitable chelating carbenes and carbene precursors are further described by Pederson et al. (U.S. Pat. Nos. 7,026,495 and 6,620,955, the disclosures of both of which are incorporated herein by reference) and Hoveyda et al. (U.S. Pat. No. 6,921,735 and WO0214376, the disclosures of both of which are incorporated herein by reference).

Other useful complexes include structures wherein $L^2$ and $R^2$ according to formulae (I), (III), or (V) are linked, such as styrenic compounds that also include a functional group for attachment to a support. Examples in which the functional group is a trialkoxysilyl functionalized moiety include, but are not limited to, the following:

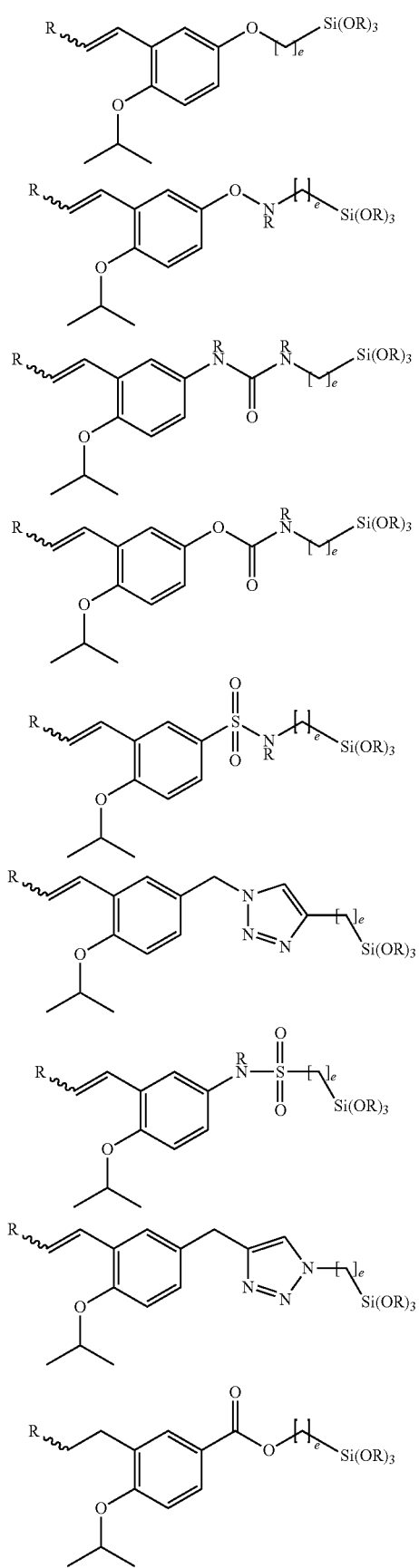
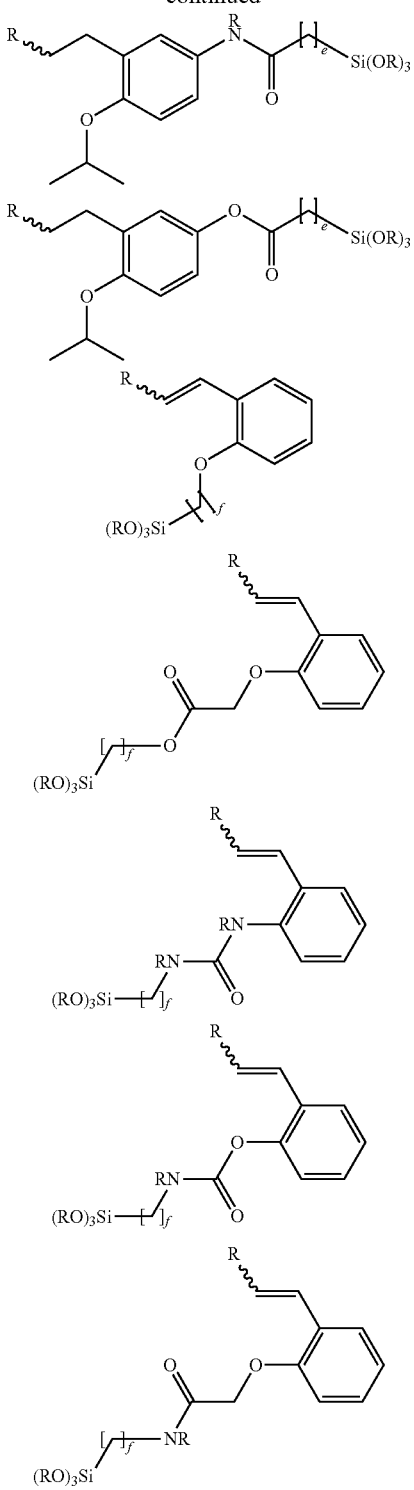

Further examples of complexes having linked ligands include those having linkages between a neutral NHC ligand and an anionic ligand, a neutral NHC ligand and an alkylidine ligand, a neutral NHC ligand and an L² ligand, a neutral NHC ligand and an L³ ligand, an anionic ligand and an alkylidine ligand, and any combination thereof. While the possible structures are too numerous to list herein, some suitable structures based on formula (III) include:

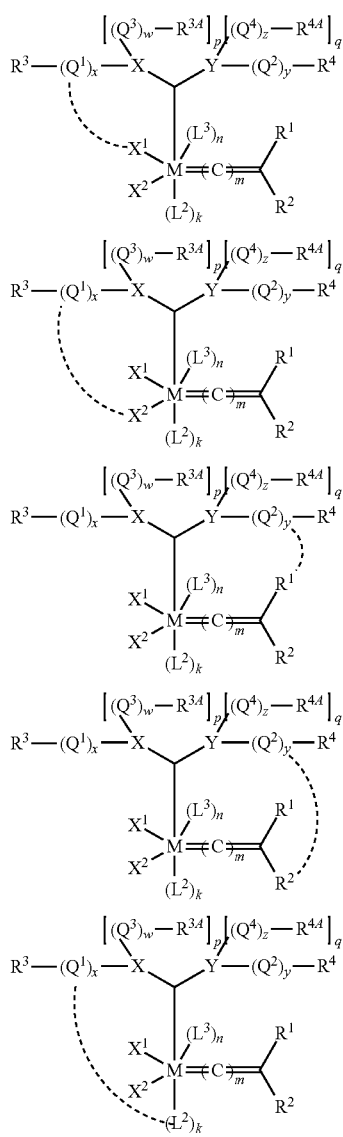
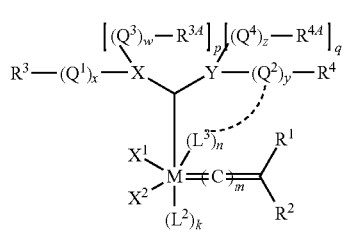
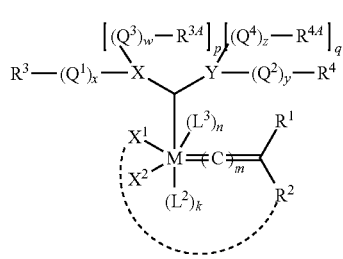
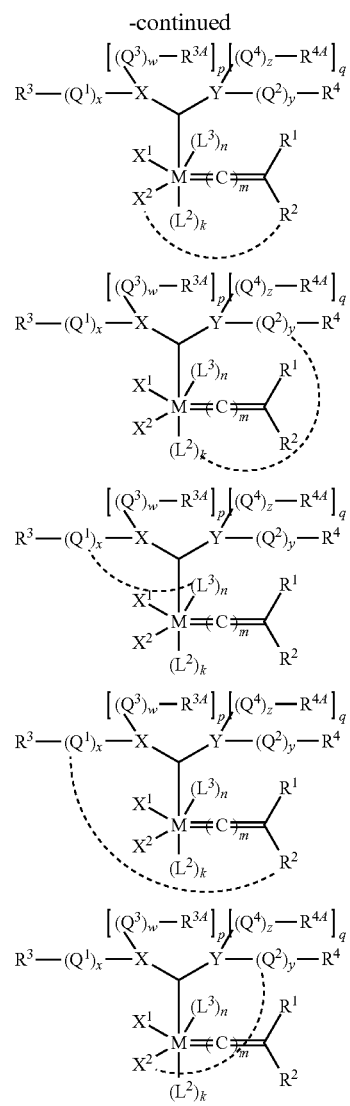

In addition to the catalysts that have the structure of formula (I), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14 or 16, are tetra-coordinated or penta-coordinated, respectively, and are of the general formula (XII)

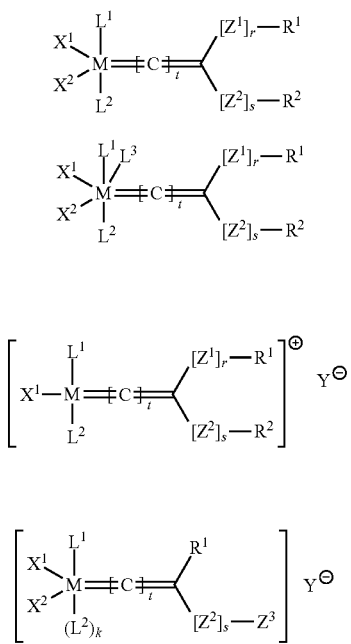

(IX)

(X)

(XI)

(XII)

wherein:
M, $X^1$, $X^2$, $L^1$, $L^2$, $L^3$, $R^1$, and $R^2$ are as defined for any of the previously defined four groups of catalysts;
r and s are independently zero or 1;
t is an integer in the range of zero to 5;
k is an integer in the range of zero to 1;
Y is any non-coordinating anion (e.g., a halide ion, $BF_4^-$, etc.);
$Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, —S(=O)$_2$—, -, and an optionally substituted and/or optionally heteroatom-containing $C_1$-$C_{20}$ hydrocarbylene linkage;
$Z^3$ is any cationic moiety such as —P($R^2$)$_3^+$ or —N($R^2$)$_3^+$; and
any two or more of $X^1$, $X^2$, $L^1$, $L^2$, $L^3$, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, $L^3$, $Z^1$, $Z^2$, $Z^3$, $R^1$, and $R^2$ may be attached to a support.

Additionally, another group of olefin metathesis catalysts that may be used in the invention disclosed herein, is a Group 8 transition metal complex having the structure of formula (XIII):

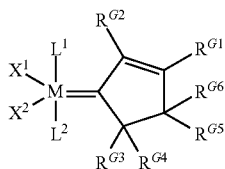

(XIII)

wherein M is a Group 8 transition metal, particularly ruthenium or osmium, or more particularly, ruthenium; $X^1$, $X^2$, $L^1$ and $L^2$ are as defined for the first and second groups of catalysts defined above; and $R^{G1}$, $R^{G2}$, $R^{G3}$, $R^{G4}$, $R^{G5}$, and $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group, or any one or more of the $R^{G1}$, $R^{G2}$, $R^{G3}$, $R^{G4}$, $R^{G5}$, and $R^{G6}$ may be attached to a support.

Additionally, one preferred embodiment of the Group 8 transition metal complex of formula XIII is a Group 8 transition metal complex of formula (XIV):

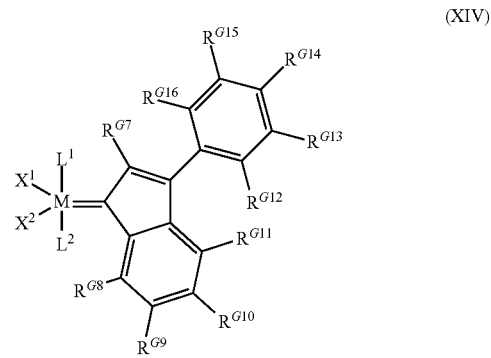

(XIV)

wherein M, $X^1$, $X^2$, $L^1$, $L^2$, are as defined above for Group 8 transition metal complex of formula XIII; and
$R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ are as defined above for $R^{G1}$, $R^{G2}$, $R^{G3}$, $R^{G4}$, $R^{G5}$ and $R^{G6}$ for Group 8 transition metal complex of formula XIII or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be linked together to form a cyclic group, or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be attached to a support.

Additionally, another preferred embodiment of the Group 8 transition metal complex of formula XIII is a Group 8 transition metal complex of formula (XV):

(XV)

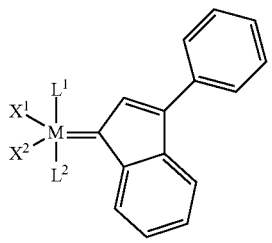

wherein M, $X^1$, $X^2$, $L^1$, $L^2$, are as defined above for Group 8 transition metal complex of formula XIII.

Additionally, another group of olefin metathesis catalysts that may be used in the invention disclosed herein, is a Group 8 transition metal complex comprising a Schiff base ligand having the structure of formula (XVI):

(XVI)

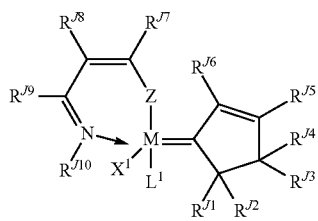

wherein M is a Group 8 transition metal, particularly ruthenium or osmium, or more particularly, ruthenium;

$X^1$, and $L^1$ are as defined for the first and second groups of catalysts defined above;

Z is selected from the group consisting of oxygen, sulfur, selenium, $NR^{J11}$, $PR^{J11}$, $AsR^{J11}$, and $SbR^{J11}$; and $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be linked together to form a cyclic group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be attached to a support.

Additionally, one preferred embodiment of the Group 8 transition metal complex of formula (XVI) is a Group 8 transition metal complex comprising a Schiff base ligand having the structure of formula (XVII):

(XVII)

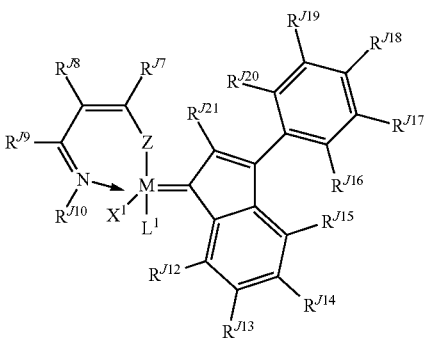

wherein M, $X^1$, $L^1$, Z, $R^{J7}$, $R^{J8}$, $R^{J9}$, $R^{J10}$, and $R^{J11}$ are as defined above for Group 8 transition metal complex of formula XVI; and $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ are as defined above for $R^{J1}$, $R^{J2}$, $R^{J3}$, $R^{J4}$, $R^{J5}$, and $R^{J6}$ for Group 8 transition metal complex of formula XVI, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be linked together to form a cyclic group, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be attached to a support.

Additionally, another preferred embodiment of the Group 8 transition metal complex of formula (XVI) is a Group 8 transition metal complex comprising a Schiff base ligand having the structure of formula (XVIII):

(XVIII)

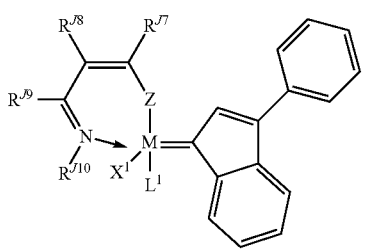

wherein M, $X^1$, $L^1$, Z, $R^{J7}$, $R^{J8}$, $R^{J9}$, $R^{J10}$, and $R^{J11}$, are as defined above for Group 8 transition metal complex of formula (XVI).

Additionally, another group of olefin metathesis catalysts that may be used in the invention disclosed herein, is a Group 8 transition metal complex comprising a Schiff base ligand having the structure of formula (XIX):

(XIX)

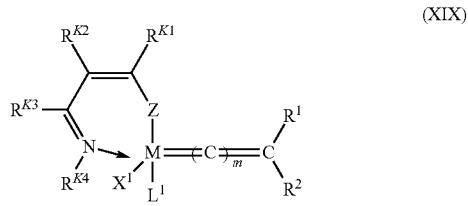

wherein M is a Group 8 transition metal, particularly ruthenium or osmium, or more particularly, ruthenium;

$X^1$, $L^1$, $R^1$, and $R^2$ are as defined for the first and second groups of catalysts defined above;

Z is selected from the group consisting of oxygen, sulfur, selenium, $NR^{K5}$, $PR^{K5}$, $AsR^{K5}$, and $SbR^{K5}$;

m is 0, 1, or 2; and $R^{K1}$, $R^{K2}$, $R^{K3}$, $R^{K4}$, and $R^{K5}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{K1}$, $R^{K2}$, $R^{K3}$, $R^{K4}$, and $R^{K5}$ may be linked together to form a cyclic group, or any one or more of the $R^{K1}$, $R^{K2}$, $R^{K3}$, $R^{K4}$, and $R^{K5}$ may be attached to a support.

In addition, catalysts of formulas (XVI) to (XIX) may be optionally contacted with an activating compound, where at least partial cleavage of a bond between the Group 8 transition metal and at least one Schiff base ligand occurs, wherein the activating compound is either a metal or silicon compound selected from the group consisting of copper (I) halides; zinc compounds of the formula $Zn(R^{Y1})_2$, wherein $R^{Y1}$ is halogen, $C_1$-$C_7$ alkyl or aryl; tin compounds represented by the formula $SnR^{Y2}R^{Y3}R^{Y4}R^{Y5}$ wherein each of $R^{Y2}$, $R^{Y3}$, $R^{Y4}$ and $R^{Y5}$ is independently selected from the group consisting of halogen, $C_1$-$C_{20}$ alkyl, $C_3$-$C_{10}$ cycloalkyl, aryl, benzyl and $C_2$-$C_7$ alkenyl; and silicon compounds represented by the formula $SiR^{Y6}R^{Y7}R^{Y8}R^{Y9}$ wherein each of $R^{Y6}$, $R^{Y7}$, $R^{Y8}$, $R^{Y9}$ is independently selected from the group consisting of hydrogen, halogen, $C_1$-$C_{20}$ alkyl, halo, $C_1$-$C_7$ alkyl, aryl, heteroaryl, and vinyl. In addition, catalysts of formulas (XVI) to (XIX) may be optionally contacted with an activating compound where at least partial cleavage of a bond between the Group 8 transition metal and at least one Schiff base ligand occurs, wherein the activating compound is an inorganic acid such as hydrogen iodide, hydrogen bromide, hydrogen chloride, hydrogen fluoride, sulfuric acid, nitric acid, iodic acid, periodic acid, perchloric acid, HOClO, $HOClO_2$ and $HOIO_3$. In addition, catalysts of formulas (XVI) to (XIX) may be optionally contacted with an activating compound where at least partial cleavage of a bond between the Group 8 transition metal and at least one Schiff base ligand occurs, wherein the activating compound is an organic acid such as sulfonic acids including but not limited to methanesulfonic acid, aminobenzenesulfonic acid, benzenesulfonic acid, p-toluenesulfonic acid (also commonly referred to as tosic acid, tosylic acid or PTSA), napthalenesulfonic acid, sulfanilic acid and trifluoromethanesulfonic acid; monocarboxylic acids including but not limited to acetoacetic acid, barbituric acid, bromoacetic acid, bromobenzoic acid, chloroacetic acid, chlorobenzoic acid, chlorophenoxyacetic acid, chloropropionic acid, cis-cinnamic acid, cyanoacetic acid, cyanobutyric acid, cyanophenoxyacetic acid, cyanopropionic acid, dichloroacetic acid, dichloroacetylacetic acid, dihydroxybenzoic acid, dihydroxymalic acid, dihydroxytartaric acid, dinicotinic acid, diphenylacetic acid, fluorobenzoic acid, formic acid, furancarboxylic acid, furoic acid, glycolic acid, hippuric acid, iodoacetic acid, iodobenzoic acid, lactic acid, lutidinic acid, mandelic acid, α-naphtoic acid, nitrobenzoic acid, nitrophenylacetic acid, o-phenylbenzoic acid, thioacetic acid, thiophene-carboxylic acid, trichloroacetic acid, and trihydroxybenzoic acid; and other acidic substances such as but not limited to picric acid and uric acid.

In addition, other examples of catalysts that may be used with the present invention are located in the following disclosures, each of which is incorporated herein by reference, U.S. Pat. Nos. 7,687,635; 7,671,224; 6,284,852; 6,486,279; and 5,977,393; International Publication Number WO2010/037550; and U.S. patent application Ser. No. 12/303,615; Ser. No. 10/590,380; Ser. No. 11/465,651 (U.S. Pat. App. Pub. No.: US 2007/0043188); and Ser. No. 11/465,651 (U.S. Pat. App. Pub. No.: US 2008/0293905 Corrected Publication); and European Pat. Nos. EP 1757613B1 and EP 1577282B1.

Non-limiting examples of catalysts that may be used to prepare supported complexes and in the reactions disclosed herein include the following, some of which for convenience are identified throughout this disclosure by reference to their molecular weight:

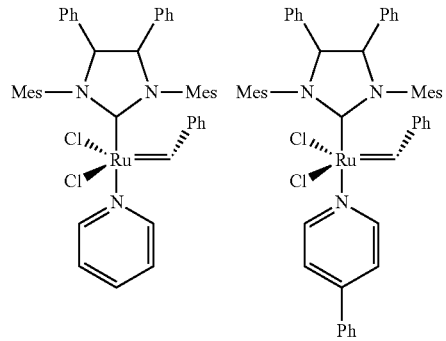

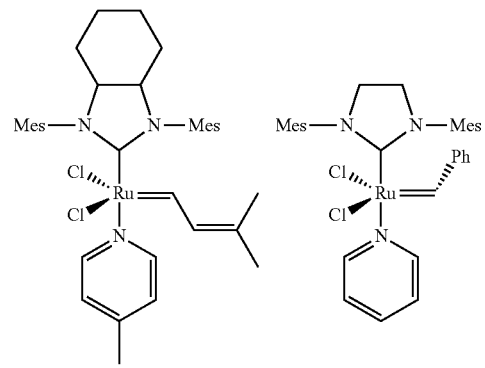

-continued
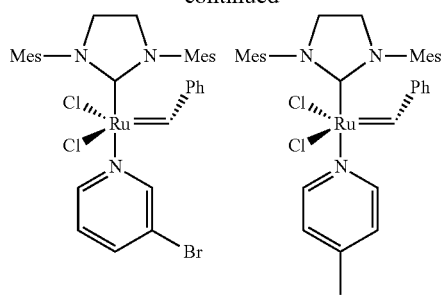
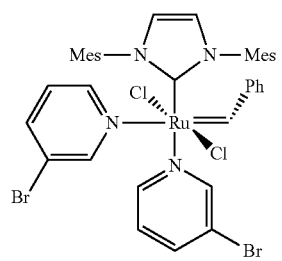
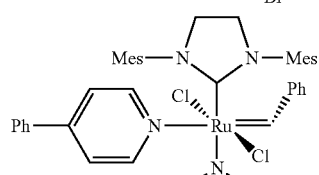
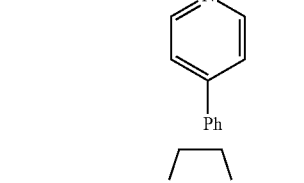
C884
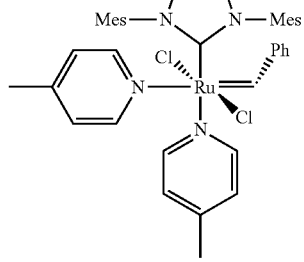
C727
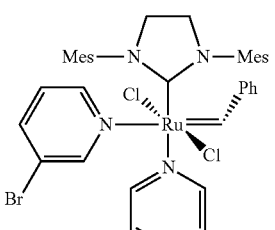
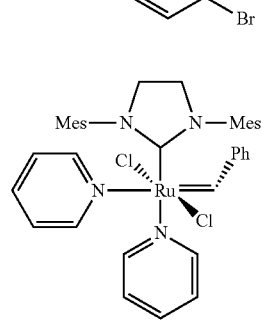
-continued
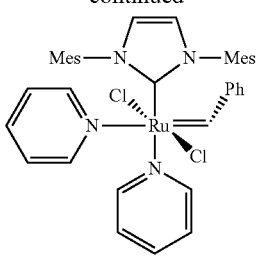
C827
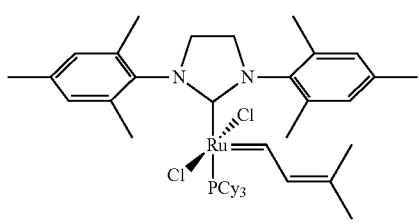
C859
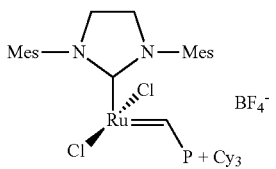
C841-n
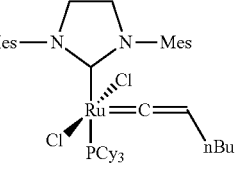
C916
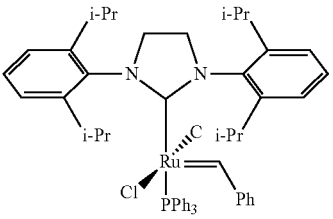
C965-p
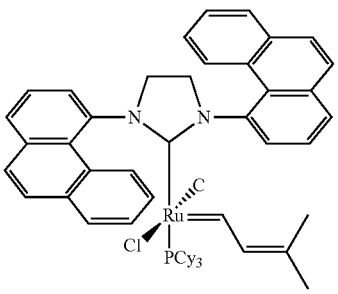
C727
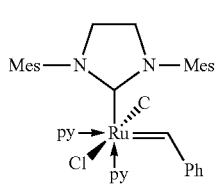

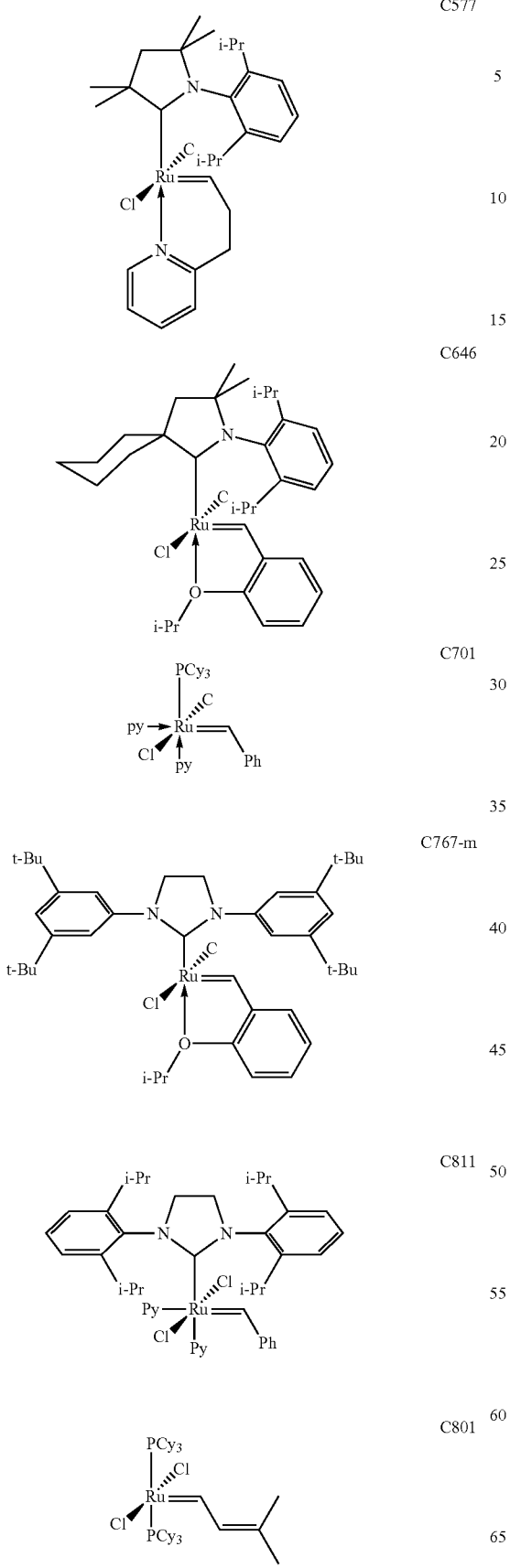
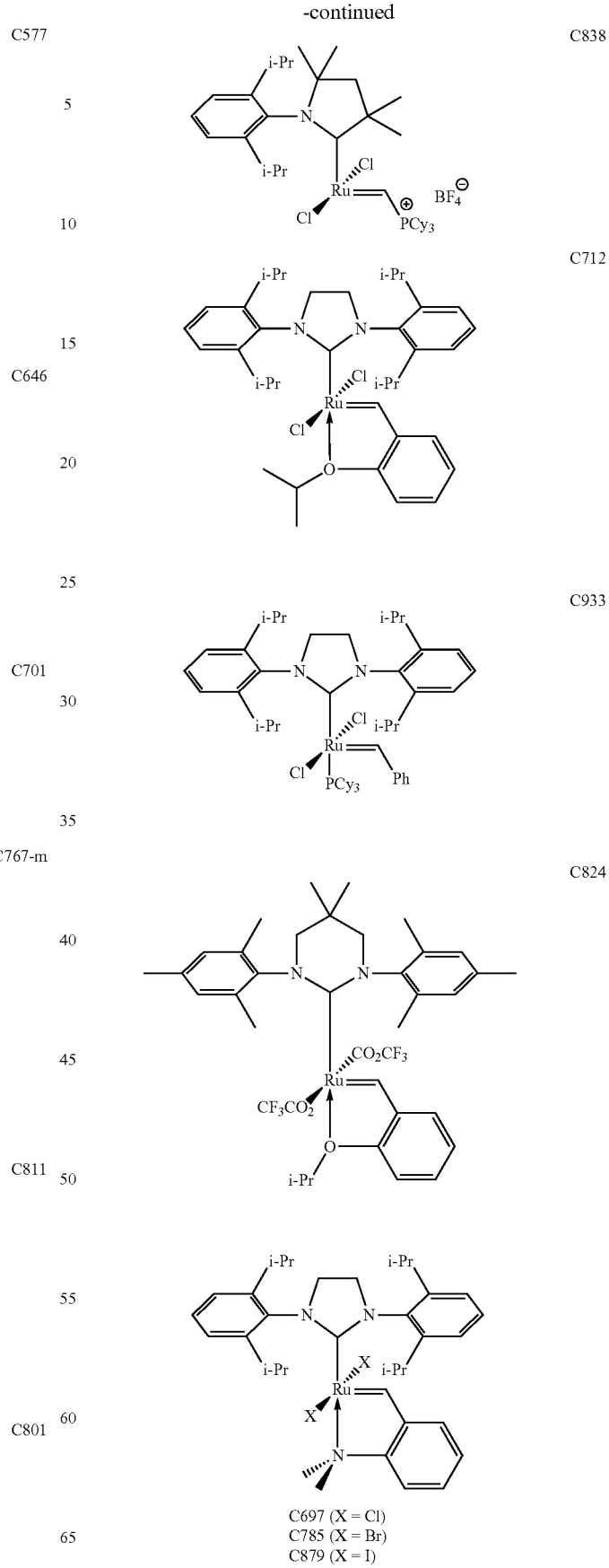

-continued
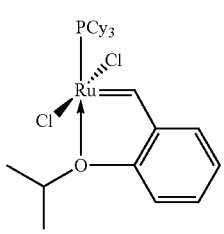
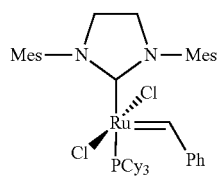
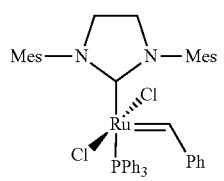
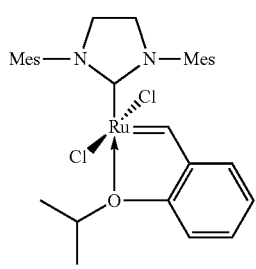
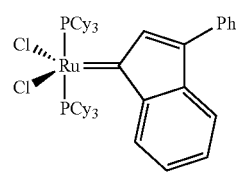
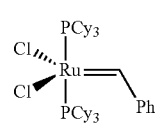
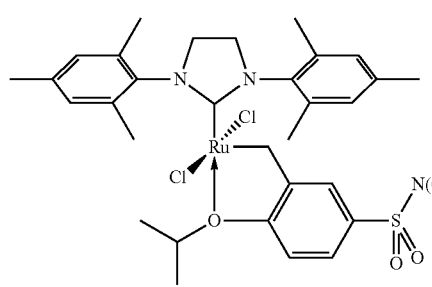
-continued
C601
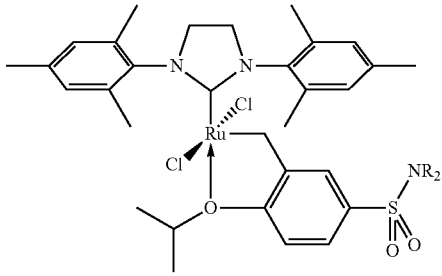
C848
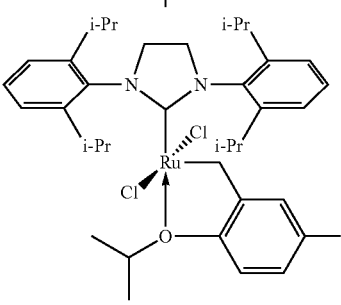
C831
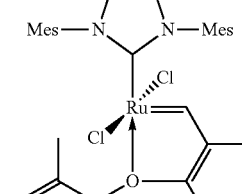
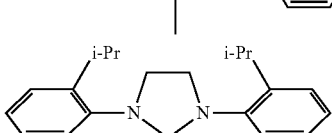
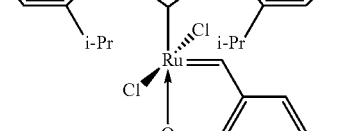
C627
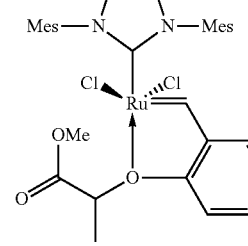
C823
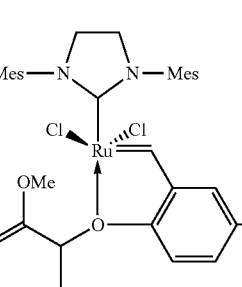
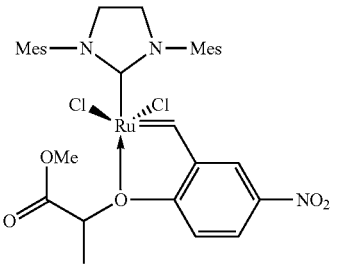

-continued
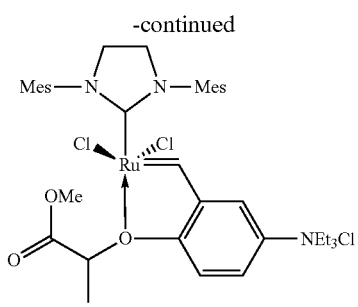
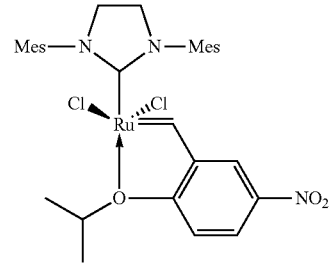
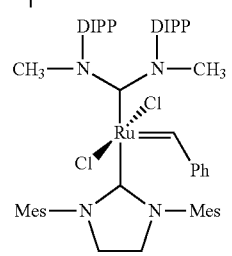
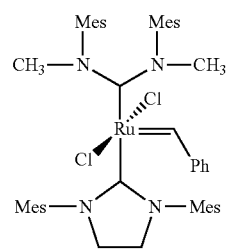
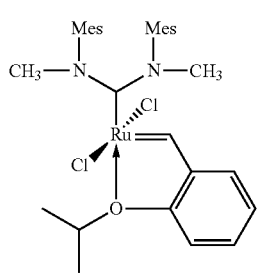
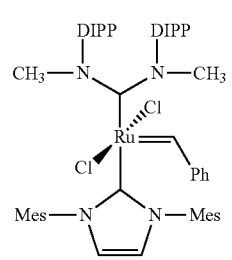
-continued
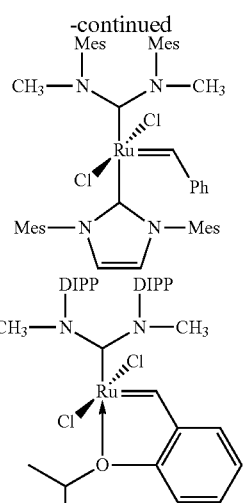
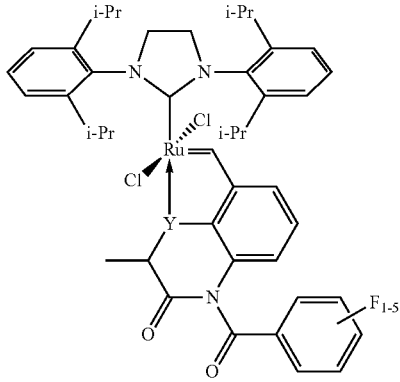
Y = O, S, NH
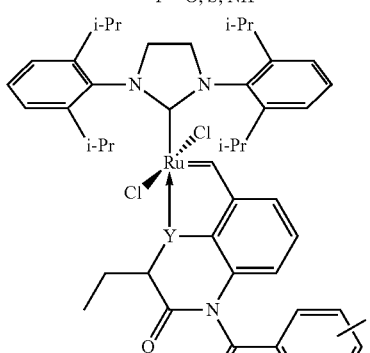
Y = O, S, NH -continued

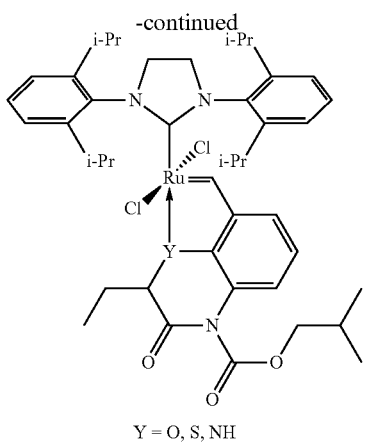

Y = O, S, NH

In the foregoing molecular structures and formulae, Ph represents phenyl, Cy represents cyclohexyl, Cp represents cyclopentyl, Me represents methyl, Bu represents n-butyl, t-Bu represents tert-butyl, i-Pr represents isopropyl, py represents pyridine (coordinated through the N atom), Mes represents mesityl (i.e., 2,4,6-trimethylphenyl), DiPP and DIPP represents 2,6-diisopropylphenyl, and MiPP represents 2-isopropylphenyl.

Further examples of catalysts useful to prepare supported complexes and in the reactions disclosed herein include the following: ruthenium (II) dichloro(3-methyl-2-butenylidene) bis(tricyclopentylphosphine) (C716); ruthenium (II) dichloro(3-methyl-2-butenylidene) bis(tricyclohexylphosphine) (C801); ruthenium (II) dichloro(phenylmethylene) bis(tricyclohexylphosphine) (C823); ruthenium (II) (1,3-bis-(2,4,6-trimethylphenyl)-2-imidazolidinylidene)dichloro(phenylmethylene)(triphenylphosphine) (C830); ruthenium (II) dichloro phenylvinylidene)bis(tricyclohexylphosphine) (C835); ruthenium (II) dichloro(tricyclohexylphosphine) (o-isopropoxyphenylmethylene) (C601); ruthenium (II) (1,3-bis-(2,4,6-trimethylphenyl)-2-imidazolidinylidene)dichloro(phenylmethylene)bis(3-bromopyridine) (C884); [1,3-bis-(2,4,6-trimethylphenyl)-2-imidazolidinylidene]dichloro(o-isopropoxyphenylmethylene)ruthenium(II) (C627); [1,3-bis-(2,4,6-trimethylphenyl)-2-imidazolidinylidene]dichloro (benzylidene)(triphenylphosphine) ruthenium(II) (C831); [1,3-bis-(2,4,6-trimethylphenyl)-2-imidazolidinylidene]dichloro (benzylidene)(methyldiphenylphosphine)ruthenium (II) (C769); [1,3-bis-(2,4,6-trimethylphenyl)-2-imidazolidinylidene]dichloro(benzylidene)(tricyclohexylphosphine) ruthenium(II) (C848); [1,3-bis-(2,4,6-trimethylphenyl)-2-imidazolidinylidene]dichloro(benzylidene) (diethylphenylphosphine) ruthenium(II) (C735); [1,3-bis-(2,4,6-trimethylphenyl)-2-imidazolidinylidene]dichloro (benzylidene)(tri-n-butylphosphine)ruthenium(II) (C771); [1,3-bis-(2,4,6-trimethylphenyl)-2-imidazolidinylidene]dichloro(3-methyl-2-butenylidene)(triphenylphosphine) ruthenium(II) (C809); [1,3-bis-(2,4,6-trimethylphenyl)-2-imidazolidinylidene]dichloro(3-methyl-2-butenylidene) (methyldiphenylphosphine)ruthenium(II) (C747); [1,3-bis-(2,4,6-trimethylphenyl)-2-imidazolidinylidene]dichloro(3-methyl-2-butenylidene) (tricyclohexylphosphine)ruthenium (II) (C827); [1,3-bis-(2,4,6-trimethylphenyl)-2-imidazolidinylidene]dichloro(3-methyl-2-butenylidene) (diethylphenylphosphine)ruthenium(II) (C713); [1,3-bis-(2,4,6-trimethylphenyl)-2-imidazolidinylidene]dichloro(3-methyl-2-butenylidene)(tri-n-butylphosphine)ruthenium(II) (C749); [1,3-bis-(2,4,6-trimethylphenyl)-2-imidazolidinylidene]dichloro(phenylindenylidene)(triphenylphosphine)ruthenium(II) (C931); [1,3-bis-(2,4,6-trimethylphenyl)-2-imidazolidinylidene]dichloro(phenylindenylidene) (methyldiphenylphosphine) ruthenium(II) (C869); [1,3-bis-(2,4,6-trimethylphenyl)-2-imidazolidinylidene]dichloro (phenylindenylidene)(tricyclohexylphosphine)ruthenium (II) (C949); [1,3-bis-(2,4,6-trimethylphenyl)-2-imidazolidinylidene]dichloro(phenylindenylidene)(diethylphenylphosphine)ruthenium(II) (C835); and [1,3-bis-(2,4,6-trimethylphenyl)-2-imidazolidinylidene]dichloro (phenylindenylidene)(tri-n-butylphosphine)ruthenium(II) (C871).

Still further catalysts useful in ROMP reactions, and/or in other metathesis reactions, such as ring-closing metathesis, cross metathesis, ring-opening cross metathesis, self-metathesis, ethenolysis, alkenolysis, acyclic diene metathesis polymerization, and combinations thereof, include the following structures:

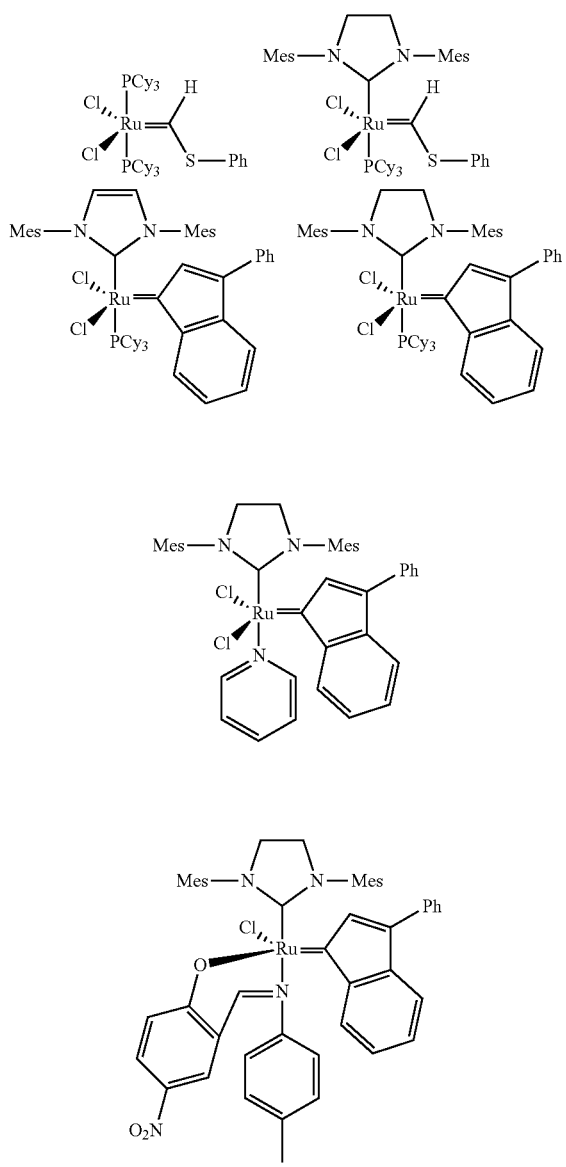

-continued

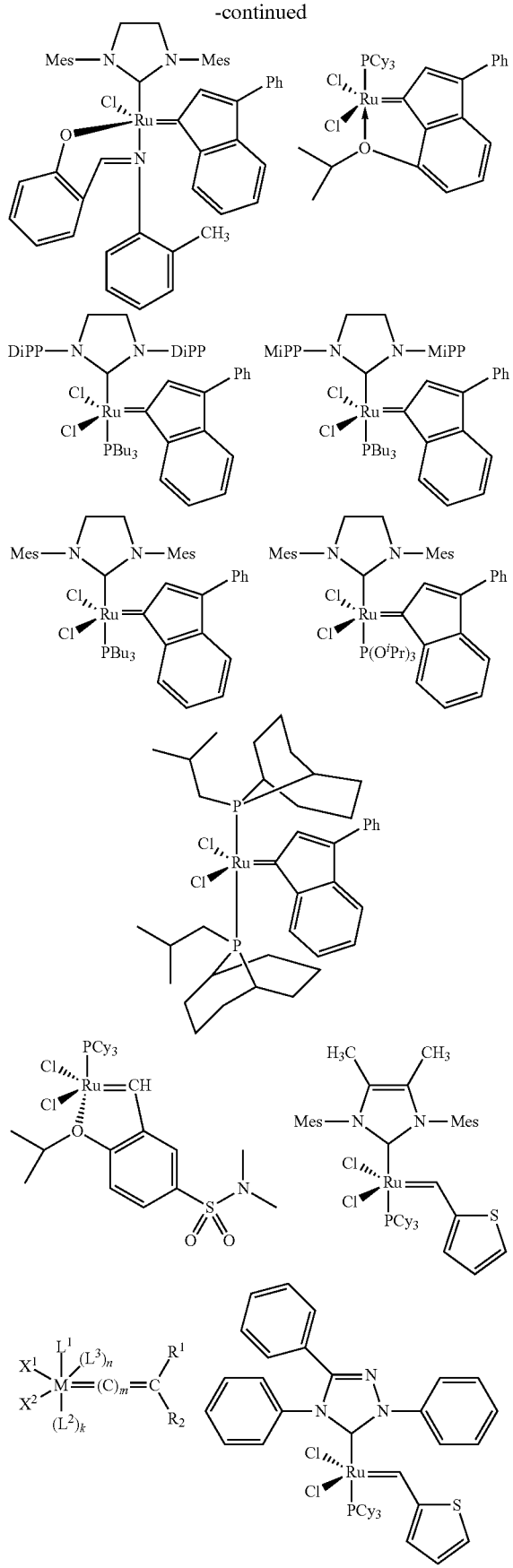

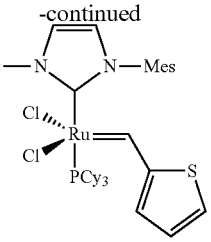

In general, the transition metal complexes used as catalysts herein can be prepared by several different methods, such as those described by Schwab et al. (1996) *J. Am. Chem. Soc.* 118:100-110, Scholl et al. (1999) *Org. Lett.* 6:953-956, Sanford et al. (2001) *J. Am. Chem. Soc.* 123: 749-750, U.S. Pat. Nos. 5,312,940, and 5,342,909, the disclosures of each of which are incorporated herein by reference. Also see U.S. Pat. Pub. No. 2003/0055262 to Grubbs et al., WO 02/079208, and U.S. Pat. No. 6,613,910 to Grubbs et al., the disclosures of each of which are incorporated herein by reference. Preferred synthetic methods are described in WO 03/11455A1 to Grubbs et al., the disclosure of which is incorporated herein by reference.

Preferred metal carbene olefin metathesis catalysts are Group 8 transition metal complexes having the structure of formula (I) commonly called "First Generation Grubbs" catalysts, formula (III) commonly called "Second Generation Grubbs" catalysts, or formula (VII) commonly called "Grubbs-Hoveyda" catalysts.

More preferred olefin metathesis catalysts have the structure of formula (I)

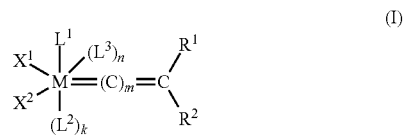

in which:
M is a Group 8 transition metal;
$L^1$, $L^2$, and $L^3$ are neutral electron donor ligands;
n is 0 or 1;
m is 0, 1, or 2;
k is 0 or 1;
$X^1$ and $X^2$ are anionic ligands;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support;
and formula (VII)

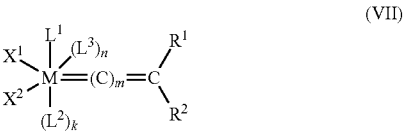

wherein,
M is a Group 8 transition metal;
$L^1$ is a neutral electron donor ligand;
$X^1$ and $X^2$ are anionic ligands;
Y is a heteroatom selected from O or N;
$R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups;
n is 0, 1, or 2; and
Z is selected from hydrogen, hydrocarbyl, substituted hydrocarbyl, heteroatom-containing hydrocarbyl, substituted heteroatom-containing hydrocarbyl, and functional groups, wherein any combination of Y, Z, $R^5$, $R^6$, $R^7$, and $R^8$ can be linked to form one or more cyclic groups, and further wherein any combination of $X^1$, $X^2$, $L^1$, Y, Z, $R^5$, $R^6$, $R^7$, and $R^8$ may be attached to a support.

Most preferred olefin metathesis catalysts have the structure of formula (I)

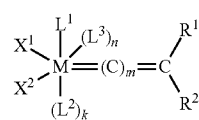

(I)

in which:
M is ruthenium;
n is 0;
m is 0;
k is 1;
$L^1$ and $L^2$ are trisubstituted phosphines independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);
$X^1$ and $X^2$ are chloride;
$R^1$ is hydrogen and $R^2$ is phenyl or —CH=C(CH$_3$)$_2$ or thienyl; or $R^1$ and $R^2$ are taken together to form 3-phenyl-1H-indene;
and formula (VII)

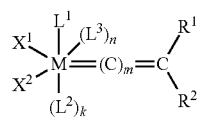

(VII)

wherein,
M is ruthenium;
$L^1$ is a trisubstituted phosphine selected from the group consisting of tri-n-butylphosphine (n-Bu$_3$P), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;
$X^1$ and $X^2$ are chloride;
Y is oxygen;
$R^5$, $R^6$, $R^7$, and $R^8$ are each hydrogen;
n is 1; and
Z is isopropyl.

Suitable supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups.

When utilized, suitable supports may be selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of a complex linked to the support.

The metathesis catalysts that are described herein may be utilized in olefin metathesis reactions according to techniques known in the art. The catalyst is typically added as a solid, a solution, or as a suspension. When the catalyst is added as a suspension, the catalyst is suspended in a dispersing carrier such as mineral oil, paraffin oil, soybean oil, tri-isopropylbenzene, or any hydrophobic liquid which has a sufficiently high viscosity so as to permit effective dispersion of the catalyst, and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

Other olefin metathesis catalysts suitable for use with the present invention include well-defined molybdenum and tungsten catalysts such as those developed by Schrock (Schrock, R. R. *Chem. Rev.* 2009, 109, 3211; Hartford, B. *Chemical & Engineering News*, "Z-Selective Metathesis of Macrocycles", Volume 89, Issue 45, Nov. 7, 2011, page 11; Yu, M.; Wang, C.; Kyle, A. F.; Jakubec, P.; Dixon, D. J.; Schrock, R. R.; Hoveyda, A. H. *Nature*, Nov. 3, 2011, 479, 88; each of which is incorporated by reference); examples are shown in Scheme 1.

Scheme 1. Examples of well-defined Molybdenum and Tungsten catalysts.

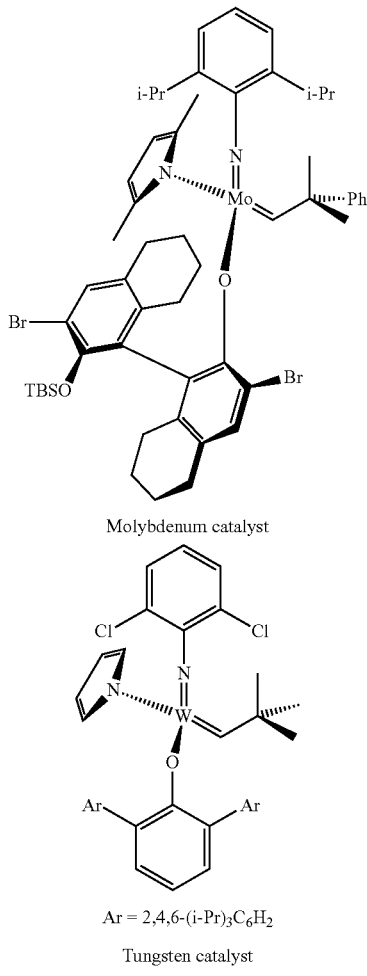

Molybdenum catalyst

Ar = 2,4,6-(i-Pr)$_3$C$_6$H$_2$

Tungsten catalyst

Ill-Defined and Heterogeneous Olefin Metathesis Catalysts

Ill-defined olefin metathesis catalysts can be dated back to the 1960's with the seminal report from Banks and Bailey of Phillips Petroleum describing an "olefin disproportionation" process catalyzed by Mo(CO)$_6$, W(CO)$_6$ and MoO$_3$ supported on alumina [Banks, R. L.; Bailey, G. C. *Ind. Eng. Chem. Prod. Res. Dev.* 1964, 170-173]. Ill-defined olefin metathesis catalysts are defined as metathesis catalysts where the metathesis active species in not well understood [Warwel, S.; Siekermann, V. *Makromol. Chem., Rapid Commun.* 1983, 4, 423; Leymet, I.; Siove, A.; Parlier, A.; Rudler, H.; Fontanille, M. *Makromol. Chem.* 1989, 190, 2397; Liaw, D.-J.; Lin, C.-L. *J. Polymer Sci., A, Polymer Chem.* 1993, 31, 3151; and a review by Grubbs R. H., Chang S. *Tetrahedron*, 1998, 54, 4413-4450], which are incorporated by reference. A few years later, chemists at Goodyear reported a catalyst system composed of a cocktail of WCl$_6$, ethanol and EtAlCl$_2$ that interconverted olefin feedstocks [Calderon, N.; Chen, H. Y.; Scott, K. W. *Tetrahedron Lett.*, 1967, 3327-3329], which is incorporated by reference. These early transition metal systems had limitations with respect to polar functional groups or impurities within the substrate feed; however, the initial discovery by Phillips Petroleum ultimately led to the development of the Phillips Triolefin Process which converted propylene into a mixture of ethylene and 2-butene using a silica-supported WO$_3$ catalyst. This heterogeneous catalyzed process was first performed on an industrial scale in 1985 by Lyondell [Mol, J. C. *Catalysis Today* 1999, 51, 289-299; Mol, J. C. *J. Mol. Catal. A: Chem.* 2004, 213, 39-45] and today Lummus Technology provides the support for the process, known as OCT® (Olefins Conversion Technology) which currently produces over 1.5 billion pounds of propylene per year [Wittcoff, H.; Reuben, B. G.; Plotkin, J. S. *Industrial organic chemicals*, $2^{nd}$ ed.; Wiley-Interscience, 2004; Mol, J. C. *J. Mol. Catal. A: Chem.* 2004, 213, 39-45], all of which are incorporated by reference.

An excellent source of information relating to non-ruthenium metal metathesis catalysts can be found in *Olefin Metathesis and Metathesis Polymerization*, K. J. Ivin and J. C. Mol Eds., Academic Press, San Diego 1997, pp 12-49, which is incorporated by reference. Examples of metathesis catalysts from the literature are listed below.

Examples of titanium metathesis catalysts include but not limited to Tebbe's reagent (Cp)$_2$TiCH$_2$(ClAlCl$_3$), TiCl$_4$ activation of W[=C(OEt)R](CO)$_5$ where R=alkyl and aryl, (Cp)$_2$TiMe$_2$, CpTiMe$_3$, CpTiMe$_2$Cl, and Cp$_2$Ti(CH$_2$SiMe$_3$)$_2$.

Examples of zirconium metathesis catalysts include but not limited to ZrCl$_4$/Et$_3$Al and Zr(acac)$_4$/Me$_3$Al$_2$Cl$_3$.

Examples of vanadium metathesis catalysts include but not limited to V(acac)$_3$/Et$_3$AlCl, and VCl$_4$/Et$_3$Al.

Examples of niobium and tantalum metathesis catalysts include but not limited to NbCl$_5$ or TACl$_5$ activated by Et$_2$AlCl or EtAlCl$_2$, and Ta(=CHCMe$_3$)(Cl)(OCMe$_3$)$_2$PMe$_3$.

Examples of chromium metathesis catalysts include but not limited to Cr(=CPh$_2$)(CO)$_5$, Bu$_4$N[CrCl(CO)$_5$]/MeAlCl$_2$ and Cr(CO)$_3$(mesitylene)/EtAlCl$_2$/O$_2$.

Examples of molybdenum metathesis catalysts include but not limited to MoCl$_5$(NO)$_2$(py)$_2$/EtAlCl$_2$, MoCl$_5$/Et$_3$Al, MoO$_3$/Al$_2$O$_3$, MoO$_3$/CoO/Al$_2$O$_3$, MoO$_3$/Al$_2$O$_3$/Et$_3$Al, MoO$_3$/SiO$_2$, Mo(CO)$_3$/Al$_2$O$_3$, Mo(CO)$_6$/Al$_2$O$_3$, Mo$_2$(OAc)$_4$/Al$_2$O$_3$, Mo$_2$(OAc)$_4$/SiO$_2$, and (n-C$_3$H$_5$)$_4$Mo/SiO$_2$.

Examples of tungsten metathesis catalysts include but not limited to WCl$_{6-x}$(OAr)$_x$ where x=0 to 6, WOCl$_{4-y}$(OAr)$_y$, and W(=NAr)$_{4-y}$(OAr)$_y$, where y=0 to 4, with co-catalysts MezAlCl$_{3-z}$ where Z=0 to 3, W(=CCMe$_3$)neopentyl/SiO$_2$, W(=CCMe$_3$)(Cl)$_3$(dme), and W(=CCMe$_3$)(OCMe$_3$)$_3$; and (2,6-Ph$_2$-PhO)$_2$(Cl)(Et$_2$O)W=CH—CMe$_3$ in Couturier, J.-L., Paillet, C., Leconte, M., Basset, J.-M., Weiss, K.; *Angew. Chem. Int. Ed. Engl.* 1992, 31, 628-631, which is incorporated by reference.

Examples of rhenium metathesis catalysts include but not limited to $Re_2O_7/Al_2O_3$, $Re_2(CO)_{10}/Al_2O_3$, $B_2O_3/Re_2O_7/Al_2O_3$—$SiO_2$, $CH_3ReO_3/SiO_2$—$Al_2O_3$, $ReCl_5/EtAlCl_2$, $ReOCl_3(PPh_3)_2/EtAlCl_2$, and $Re(CO)_5Cl/EtAlCl_2$.

Examples of osmium metathesis catalysts include but not limited to $OsCl_3 3H_2O/EtOH$ and $OsO_4$ in chlorobenzene 60° C.

Examples of iridium metathesis catalysts include but not limited to $[(C_8H_{14})_2IrCl]_2$ and excess of $CF_3CO_2Ag$, $[(C_8H_{14})_2IrO_2CCF_3]_2$, $[(NH_4)_2IrCl_6/EtOH]$.

Hydrovinylation

Hydrovinylation is an atom-efficient process to add ethylene to a double bond (see Scheme 2). Several recent hydrovinylation reviews include Jolly, P. W.; Wilke, G. In Applied Homogeneous Catalysis with Organometallic Compounds; Cornils, B., Herrmann, W. A., Eds.; VCH: New York, 2002; Vol. 3, p 1164, RajanBabu, T. V.; Chem. Rev. 2003, 103, 2845-2860, RajanBabu, T. V.; Synlett 2009, 6, 853-885 and Ceder, R. M.; Grabulosa, A.; Muller, G.; Rocamora, M. Catalysis Science and Technology 2013, (manuscript accepted, DOI: 10.1039/C3CY00084B) describe numerous hydrovinylation catalysts and reactions, which are incorporated herein by reference. These reviews disclose asymmetric hydrovinylation reactions. Any racemic or asymmetric hydrovinylation catalyst can be used in the present invention.

Scheme 2. General hydrovinylation reaction.

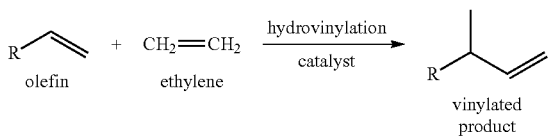

R = hydrocarbyl, substituted hydrocarbyl, heteroatom-containing hydrocarbyl, substituted heteroatom-containing hydrocarbyl, and functional groups.

Numerous embodiments of catalysts that affect the hydrovinylation of styrene [i.e., codimerization of styrene and ethylene] and other olefins have been reported in academic and patent literature. These include but are not limited to:

Hydrates of $RuCl_3$ and $RhCl_3$ [Alderson, T.; Jenner, E. L.; Lindsey, R. V., Jr. J. Am. Chem. Soc. 1965, 87, 5638.] is incorporated by reference.

Ni(II) hydrovinylation complexes include: $NiCl_2(PBu_3)_2/AlEt_2Cl$ [Dzhemilev, U. M.; Gubaidullin, L. Y.; Tolstikov, G. A. Bull. Acad. Sci. USSR 1976, 2009.] $Ni(acac)_2/Et_3Al/BF_3.OEt_2/P(OPh)_3$ [Azizov, A. G.; Mamedaliev, G. A.; Aliev, S. M.; Aliev, V. S. Azerb. Khim. Zh. 1979, 3.] $Ni(Ar)(Br)_2(PPh_3)_2/BF_3.OEt_2$; where Ar=o-tolyl, 1-naphthyl or mesityl [Kawata, N.; Maruya, K.; Mizoroki, T.; Ozaki, A. Bull. Chem. Soc. Jpn. 1971, 44, 3217. Kawata, N.; Maruya, K.; Mizoroki, T.; Ozaki, A. Bull. Chem. Soc., Jpn. 1974, 47, 413. Kawakami, K.; Kawata, N.; Maruya, K.; Mizoroki, T.; Ozaki, A. J. Catal. 1975, 39, 134.] $NiX_2/AlEt_3/BF_3.OEt_2/P(OPh)_3$ [Mamedaliev, G. A.; Azizov, A. G.; Yu, G. Pol. J. (Japan) 1985, 17, 1075. Azizov, A. G.; Mamedaliev, G. A.; Aliev, S. M.; Aliev, V. S. Azerb. Khim. Zh. 1978, 3.]$[Ni(\eta^3\text{-allyl})Br]_2/PPh_3/AgOTf$ [Nomura, N.; Jin, J.; Park, H.; Rajanbabu, T. V. J. Am. Chem. Soc. 1998, 120, 459.]$[Ni(MeCN)_6][BF_4]2$, L, $AlEt_2Cl$ (L=monophosphine, diphosphine, aminophosphine) [Fassina, V.; Ramminger, C.; Seferin, M.; Monteiro, A. L. Tetrahedron 2000, 56, 7403-7409.] trans-$[Ni(2,4,6-Me_3C_6H_2)(CH_3CN)(P(CH_2Ph)_3)_2]BF_4$ [Ceder, R.; Muller, G.; Ordinas, J. I. J. Mol. Catal. 1994, 92, 127, and Muller, G.; Ordinas, J. I. J. Mol. Catal. A: Chem. 1997, 125, 97, are all incorporated by reference.

Pd(II) hydrovinylation complexes include: $PdCl_2(PhCN)_2$ [Barlow, M. G.; Bryant, M. J.; Haszeldine, R. N.; Mackie, A. G. J. Organomet. Chem. 1970, 21, 215.] $Pd(OAc)_2/Et_2P(CH_2)_3PEt_2/PTSA$ [Drent, E. U.S. Pat. No. 5,227,561, 1993. Kawamoto, K.; Tatani, A.; Imanaka, T.; Teranishi, S. Bull. Chem. Soc., Jpn. 1971, 44, 1239.]$(PPh_3)_2Pd(Ph)(X)/H_2O$, where X=Br or I [Nozima, H.; Kawata, N.; Nakamura, Y.; Maruya, K.; Mizoroki, T.; Ozaki, A. Chem. Lett. 1973, 1163.] are all incorporated by reference.

Co(II) hydrovinylation complexes include: $CoL_2Cl_2$, $AlEt_2Cl$ (L=monophosphine or $L_2$=diphosphine) [Grutters, M. M. P.; van der Vlugt, J. I.; Pei, Y.; Mills, A. M.; Lutz, M.; Spek, A. L.; Müller, C.; Moberg, C.; Vogt, D. Adv. Synth. Catal. 2009, 351, 2199-2208.] are all incorporated by reference.

Ru(II) hydrovinylation complexes include: $(PCy_3)_2(CO)RuHCl/HBF_4.OEt_2$ [Yi, C. S.; He, Z.; Lee, D. W. Organometallics 2001, 20, 802-804.](L)(CO)RuHCl/AgX (L=2 $PCy_3$, diphosphine, X=OTf, $SbF_6$) [RajanBabu, T. V.; Nomura, N.; Jin, J.; Nandi, M.; Park, H.; Sun, X. J. Org. Chem. 2003, 68, 8431. Sanchez, R. P. Jr.; Connell, B. T. Organometallics 2008, 27, 2902-2904.] are all incorporated by reference.

Hydrovinylation catalysts suitable for the present invention include but are not limited to hydrates of $RuCl_3$ and $RhCl_3$, $NiCl_2(PBu_3)_2/AlEt_2Cl$, $Ni(acac)_2/Et_3Al/BF_3.OEt_2/P(OPh)_3$, $Ni(Ar)(Br)(PR_3)_2/BF_3.OEt_2$, $NiX_2/AlEt_3/BF_3.OEt_2/P(OPh)_3$, $[Ni(\eta^3\text{-allyl})Br]_2/PPh_3/AgOTf$ (X=Cl, Br, I), $[Ni(MeCN)_6][BF_4]_2L/AlEt_2Cl$ (L=monophosphine, diphosphine, aminophosphine), trans-$[Ni(2,4,6-Me_3C_6H_2)(CH_3CN)(P(CH_2Ph)_3)_2]BF_4$, $PdCl_2(PhCN)_2$, $Pd(OAc)_2/Et_2P(CH_2)_3PEt_2/PTSA$, $(PPh_3)_2Pd(Ph)(X/H_2O)$ (X=OTf, $SbF_6$), $COL_2Cl_2/AlEt_2Cl$ (L=monophosphine or $L_2$=diphosphine), $(PCy_3)_2(CO)RuHCl/HBF_4.OEt_2$, and (L)(CO)RuHCl/AgX (L=2 $PCy_3$, diphosphine, X=OTf, $SbF_6$).

Additional hydrovinylation catalysts suitable for use in the present invention include hydrovinylation catalysts HV-1 to HV-16 shown in FIG. 1.

Preferred hydrovinylation catalysts for the hydrovinylation of substituted and unsubstituted styrenes include: $[Ni(MeCN)_6][BF_4]2PPh_3/AlEt_2Cl$, $Co(PPh_3)_2Cl_2/AlEt_2Cl$, $(PCy_3)_2(CO)RuHCl/HBF_4.OEt_2$ and $(PCy_3)_2(CO)RuHCl/AgOTf$. Preferred hydrovinylation catalysts for the hydrovinylation of terpenes, particularly β-farnesene, include: HV-1, HV-2, and HV-4.

More preferred hydrovinylation catalysts for the hydrovinylation of substituted and unsubstituted styrenes include: $Co(PPh_3)_2Cl_2/AlEt_2Cl$ and $(PCy_3)_2(CO)RuHCl/HBF_4\cdot OEt_2$. More preferred hydrovinylation catalysts for the hydrovinylation of terpenes, particularly β-farnesene include: HV-1 and HV-2.

Olefinic substrates and/or cross metathesis substrates of the present invention may be hydrovinylated to provide hydrovinylation products for use in the cross metathesis reactions of the present invention. Non-limiting examples of hydrovinylation products of the present invention prepared by the hydrovinylation of olefinic substrates and/or hydrovinylation of cross metathesis substrates of the present invention are exemplified below.

Scheme 3. Hydrovinylation of
β-farnesene.to yield vinylated farnesene (VF$_{1-3}$).

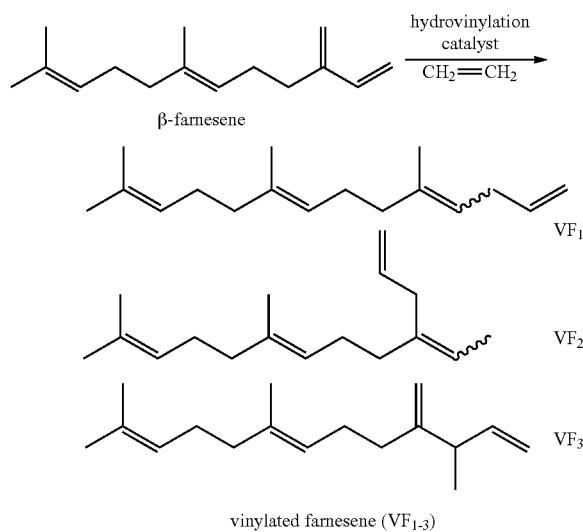

Scheme 4. Hydrovinylation of
styrene to yield 3-phenyl-1-butene (3Ph1C4).

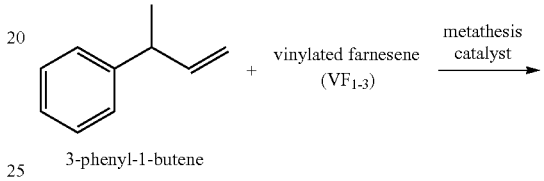

Scheme 5. Hydrovinylation of
β-myrcene to yield vinylated myrcene (VM).

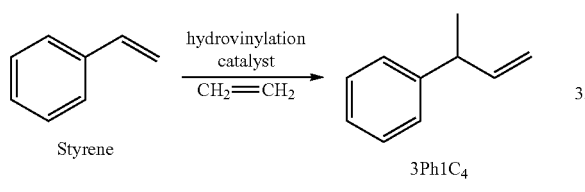

Cross Metathesis Reactions

According to the present invention, hydrovinylated products (e.g. hydrovinylated olefinic substrates and/or hydrovinylated cross metathesis substrates) may be combined in the presence of at least one olefin metathesis catalyst to provide cross metathesis products. Non-limiting examples of cross metathesis products of the present invention prepared by a cross metathesis reaction between at least one hydrovinylated olefinic substrate and at least one hydrovinylated cross metathesis substrate in the presence of at least one olefin metathesis catalyst are exemplified below.

Scheme 6. Cross metathesis reaction of
3-phenyl-1-butene with vinylated farnesene.

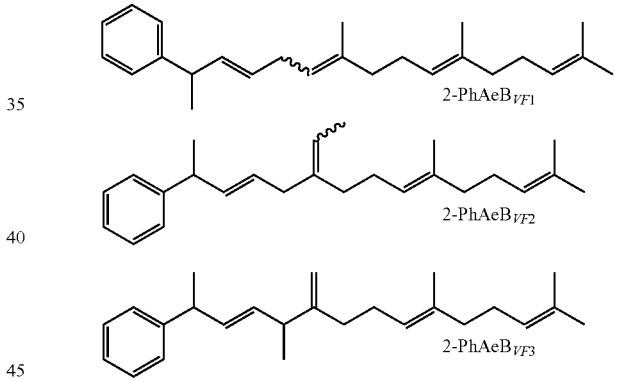

Scheme 7. Cross metathesis of sulfonated
3-phenyl-1-butene with vinylated farnesene (VF$_{1-3}$).

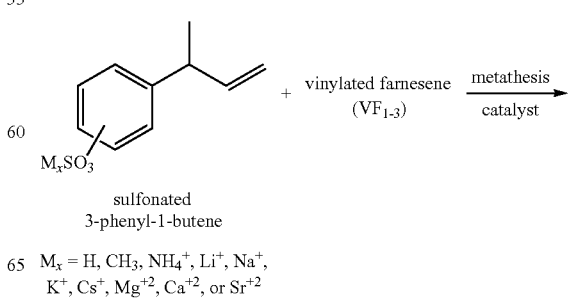

$M_x$ = H, $CH_3$, $NH_4^+$, $Li^+$, $Na^+$, $K^+$, $Cs^+$, $Mg^{+2}$, $Ca^{+2}$, or $Sr^{+2}$

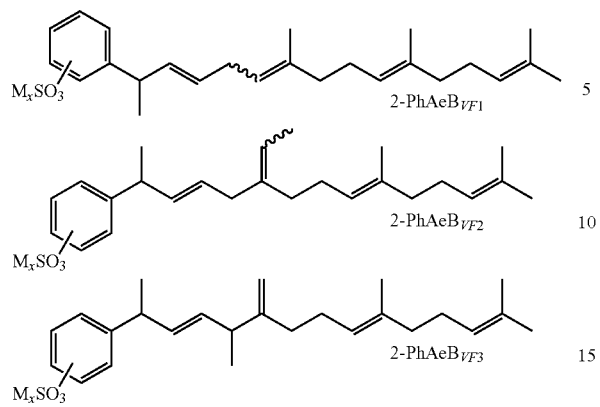

Furthermore, according to the present invention at least one hydrovinylated olefinic substrate may be combined with at least one cross metathesis substrate in the presence of at least one olefin metathesis catalyst to provide cross metathesis products. Non-limiting examples of cross metathesis products of the present invention prepared by a cross metathesis reaction between at least one hydrovinylated olefinic substrate and at least one cross metathesis substrate in the presence of at least one olefin metathesis catalyst are exemplified below.

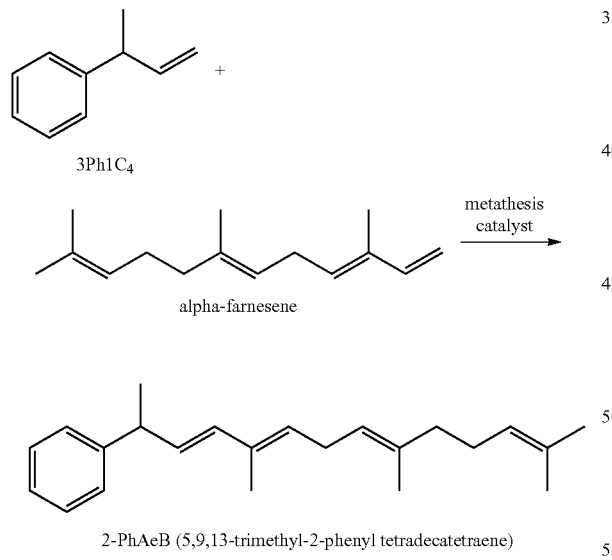

Furthermore, according to the present invention at least one olefinic substrate may be combined with at least one hydrovinylated cross metathesis substrate in the presence of at least one olefin metathesis catalyst to provide cross metathesis products. Non-limiting examples of cross metathesis products of the present invention prepared by a cross metathesis reaction between at least one olefinic substrate and at least one hydrovinylated cross metathesis substrate in the presence of at least one olefin metathesis catalyst are exemplified below.

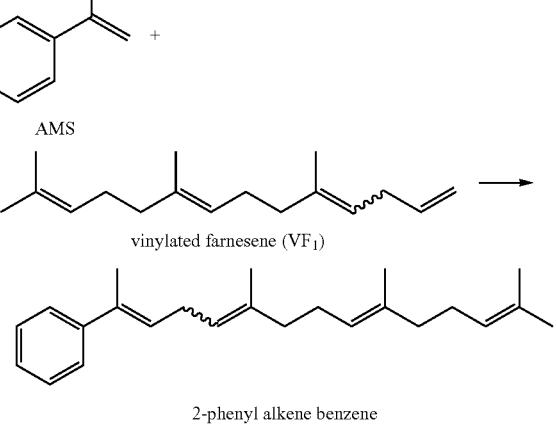

Furthermore, according to the present invention at least one olefinic substrate may be combined with at least one cross metathesis substrate in the presence of at least one olefin metathesis catalyst to provide cross metathesis products. Non-limiting examples of cross metathesis products of the present invention prepared by a cross metathesis reaction between at least one olefinic substrate and at least one cross metathesis substrate in the presence of at least one olefin metathesis catalyst are exemplified below.

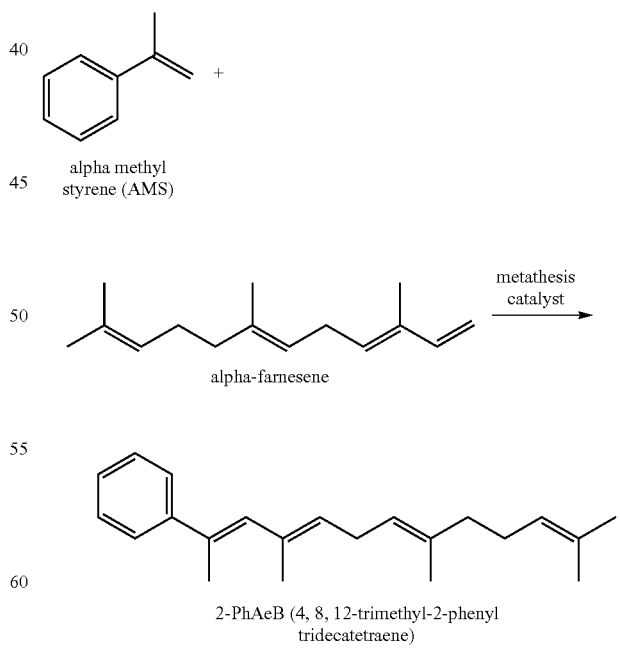

Alkene benzenes (e.g., 2-PhAeB) may be hydrogenated (olefin hydrogenation) by well-known methodologies to yield alkyl benzenes (e.g., 2-PhAB).

Scheme 11. Hydrogenation of alkene benzenes (e.g. 2-PhAeB) to yield alkylbenzenes (e.g. 2-PhAB).

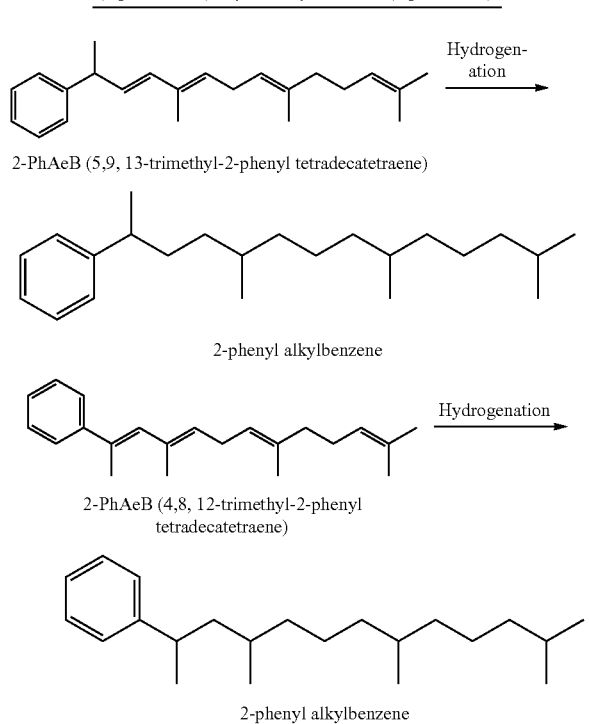

2-PhAeB (5,9, 13-trimethyl-2-phenyl tetradecatetraene)

2-phenyl alkylbenzene

2-PhAeB (4,8, 12-trimethyl-2-phenyl tetradecatetraene)

2-phenyl alkylbenzene

Alkylbenzenes (e.g. 2-PhAB) may be sulfonated by well-known methodologies to yield alkylbenzene sulfonates (e.g., 2-phenyl alkylbenzene sulfonates. Alkylbenzene sulfonates, particularly 2-phenyl alkylbenzene sulfonates, are commercially important surfactants used in hand soaps, dish soaps, hard surface cleaners, laundry detergents, cleaning supplies, etc.

Scheme 12. Sulfonation of alkylbenzenes (e.g. 2-PhAB) to yield alkylbenzene sulfonates (e.g. 2-PhABS).

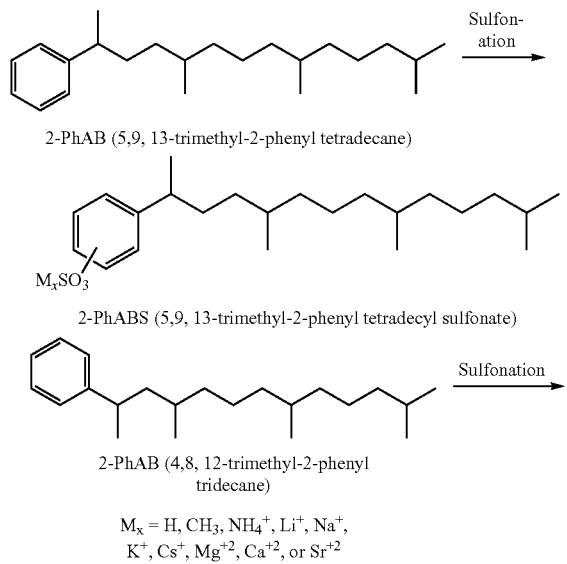

2-PhAB (5,9, 13-trimethyl-2-phenyl tetradecane)

2-PhABS (5,9, 13-trimethyl-2-phenyl tetradecyl sulfonate)

2-PhAB (4,8, 12-trimethyl-2-phenyl tridecane)

$M_x$ = H, $CH_3$, $NH_4^+$, $Li^+$, $Na^+$, $K^+$, $Cs^+$, $Mg^{+2}$, $Ca^{+2}$, or $Sr^{+2}$

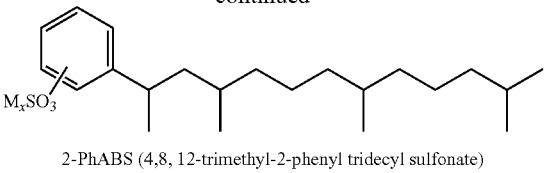

2-PhABS (4,8, 12-trimethyl-2-phenyl tridecyl sulfonate)

Furthermore, according to the present invention at least one olefinic substrate may be combined with at least one cross metathesis substrate in the presence of at least one olefin metathesis catalyst to provide cross metathesis products. Non-limiting examples of cross metathesis products of the present invention prepared by a cross metathesis reaction between at least one olefinic substrate and at least one cross metathesis substrate in the presence of at least one olefin metathesis catalyst are exemplified below. Hydrovinylated farnesene (VF1) is cross metathesized with 1,4-diacetoxy-2-butene to yield 6,10,14,-trimethyl-pentadeca-2,5,9,13-tetraenyl acetate. Various protecting groups of 1,4-dihydroxy-2-butene are acceptable including but not limited to formate, propionate, butyrate, benzyl, benzoyl, TMS, THP, ethyl vinyl ethers, methyl, ethyl, ethylene glycol and methyl ethers of ethylene glycol, sulfate, sulfonate, phosphates and phosphonates.

Scheme 13. Cross metathesis of 1,4-diacetoxy-2-butene with vinylated farnesene ($VF_1$).

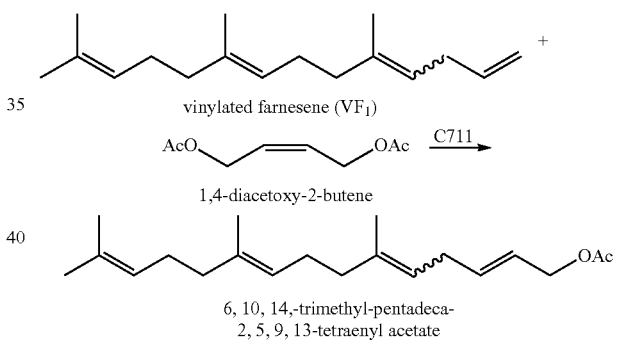

vinylated farnesene ($VF_1$)

1,4-diacetoxy-2-butene 6, 10, 14,-trimethyl-pentadeca-2, 5, 9, 13-tetraenyl acetate Hydrovinylated farnesene (VF1) is cross metathesized with allyl acetate to yield 6,10, 14,-trimethyl-pentadeca-2,5,9,13-tetraenyl acetate. Various protecting groups of 1,4-allyl alcohol are acceptable including but not limited to formate, propionate, butyrate, benzyl, benzoyl, TMS, THP, ethyl vinyl ethers, methyl, ethyl, ethylene glycol and methyl ethers of ethylene glycol, sulfate, sulfonate, phosphates and phosphonites.

Scheme 14. Cross metathesis of allyl acetate with vinylated farnesene ($VF_1$).

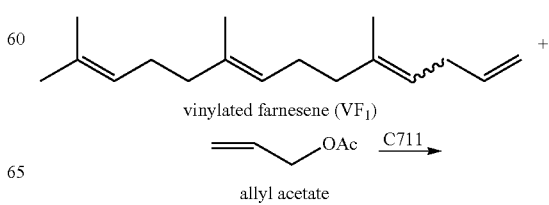

vinylated farnesene ($VF_1$)

allyl acetate

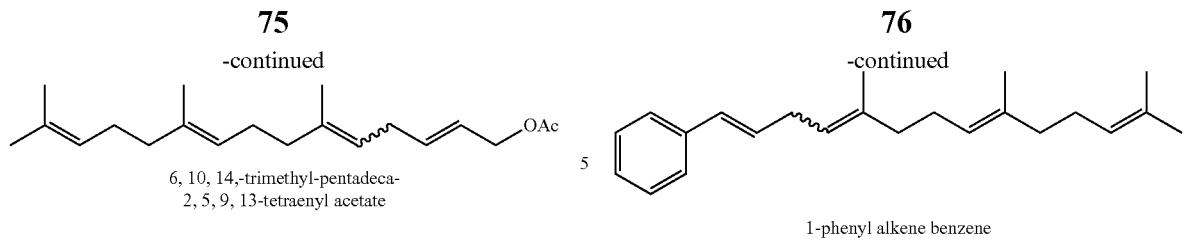

6, 10, 14,-trimethyl-pentadeca-2,5,9,13-tetraenyl acetate 1-phenyl alkene benzene Hydrovinylated farnesene (VF1) is cross metathesized with styrene to yield 1-phenyl-4, 8,12,-trimethyl-tetradeca-1,4,8,12-tetraenyl acetate. Various aromatic styrenes may be used including but not limited to naphthyl styrenes, tolylstyrene, xylylstyrenes, mesityl styrenes, halogenated styrenes such as fluorostyrene, chlorostyrene, bromostyrene, iodostyrene, heteroatom containing styrenes with the aromatic styrene ring optionally containing one or more functional groups.

Scheme 15. Cross metathesis of styrene with vinylated farnesene (VF$_1$).

Scheme 16. Cross metathesis of tolylstyrene with vinylated farnesene (VF$_1$)

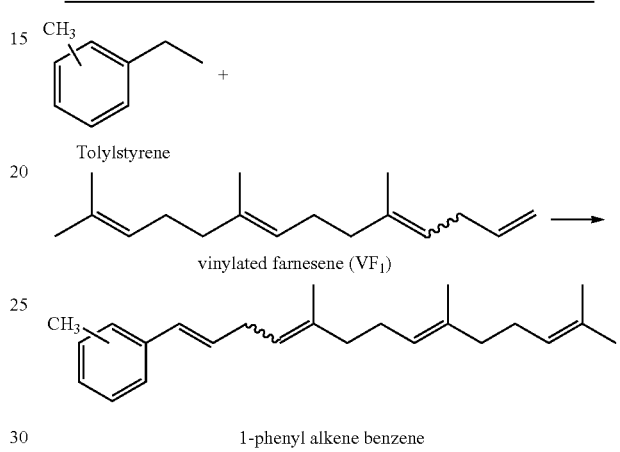

Tolylstyrene vinylated farnesene (VF$_1$)

1-phenyl alkene benzene

Styrene vinylated farnesene (VF$_1$)

Scheme 17. Self metathesis of vinylated farnesene (VF$_1$) to yield homo-squalene

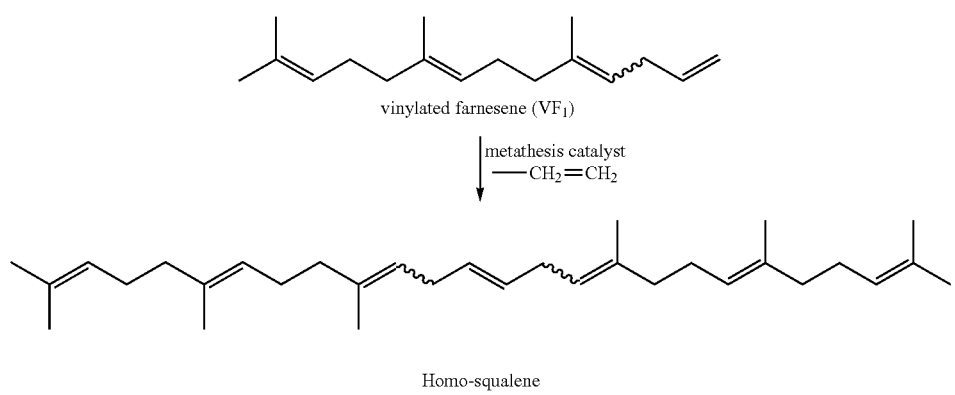

vinylated farnesene (VF$_1$)

metathesis catalyst
—CH$_2$=CH$_2$

Homo-squalene

Scheme 18. Hydrogenation of homo-squalene to yield homo-squalane.

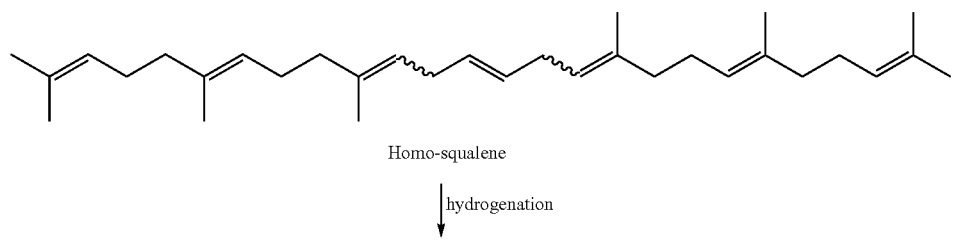

Homo-squalene hydrogenation

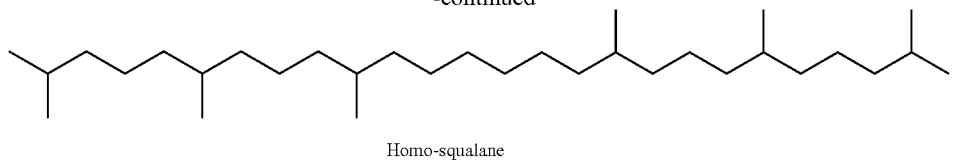

Homo-squalane

Scheme 19. Self-hydrovinylation of farnesene to yield squalene isomers

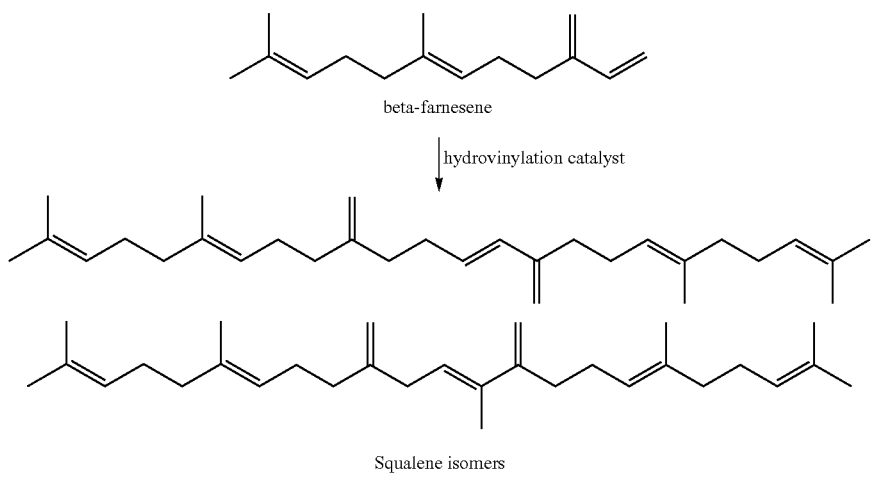

beta-farnesene

| hydrovinylation catalyst

Squalene isomers

Scheme 20. Hydrogenation of squalene isomers to yield squalane isomers

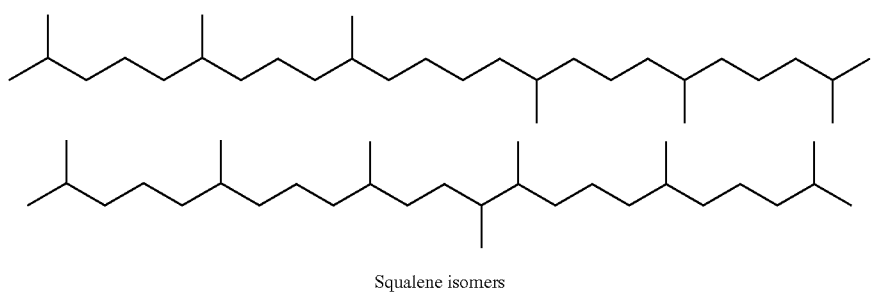

Squalene isomers

Scheme 21. Cross metathesis of ethyl acrylate with vinylated farnesene (VF$_1$).

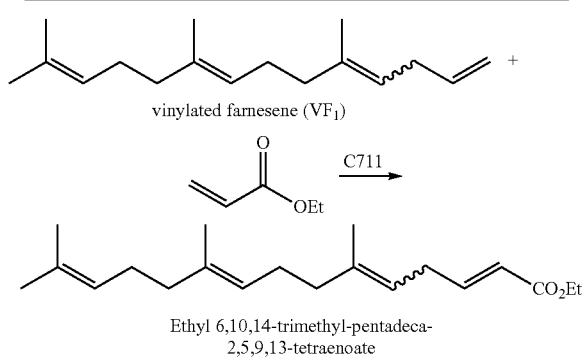

vinylated farnesene (VF$_1$)

C711

Ethyl 6,10,14-trimethyl-pentadeca-2,5,9,13-tetraenoate

Scheme 22. Hydrogenation of Ethyl 6,10,14-trimethyl-pentadeca-2,5,9,13-tetraenoate

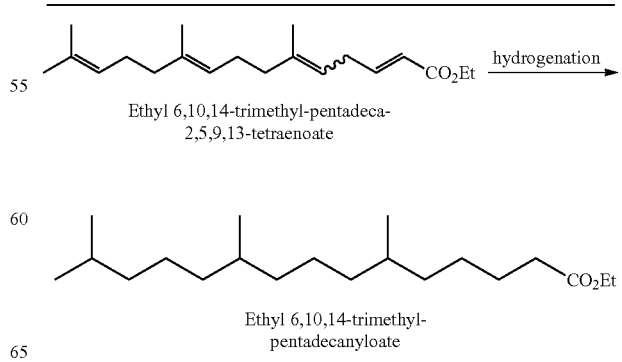

Ethyl 6,10,14-trimethyl-pentadeca-2,5,9,13-tetraenoate hydrogenation

Ethyl 6,10,14-trimethyl-pentadecanyloate

Scheme 23. Branched Estolide synthesis
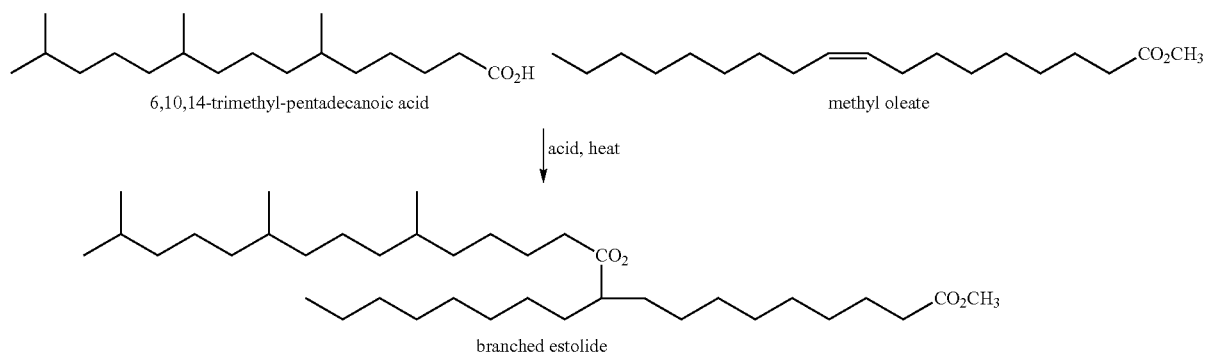
Scheme 24. Hydrogenation of 6,10,14,-trimethyl-pentadeca-2,5,9,13-tetraenyl acetate.
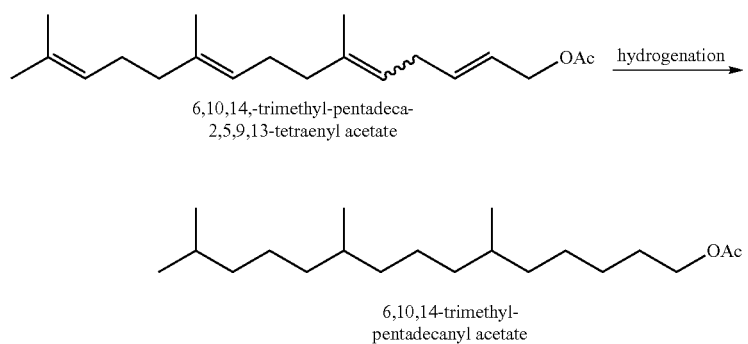
Scheme 25. Derivatives of 6,10,14-trimethyl-pentadecanol.
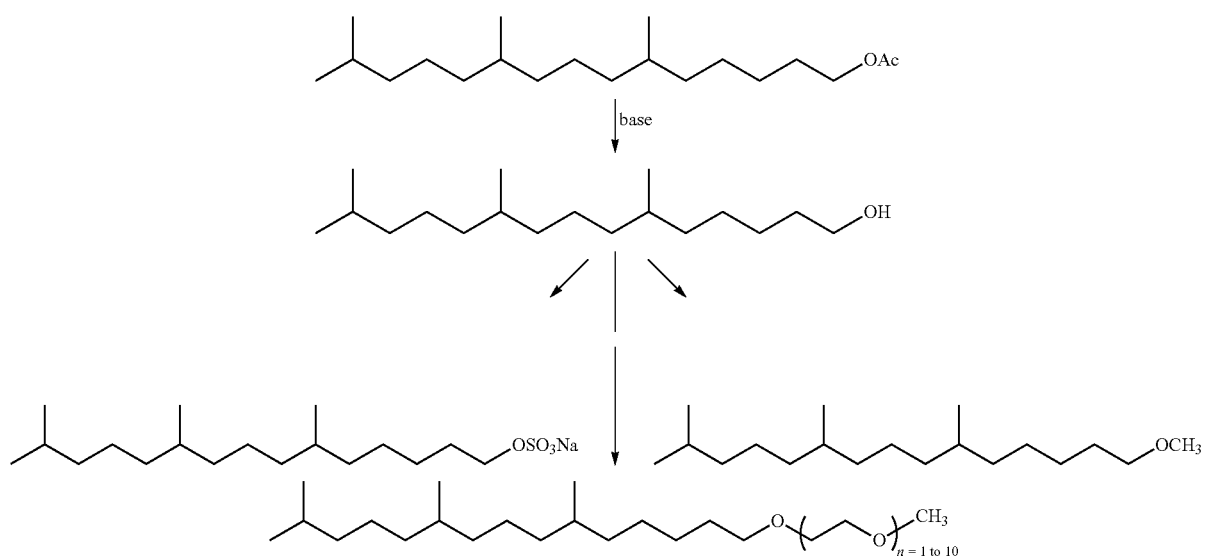

Scheme 26. Sulfation of 6,10,14,-trimethyl-pentadecanol to yield 6,10,14,-trimethyl-pentadecyl sulfate.

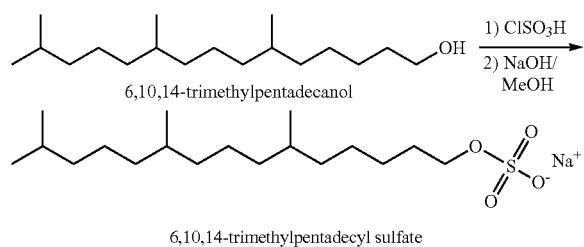

6,10,14-trimethylpentadecyl sulfate

Preferred hydrovinylated cross metathesis substrates (i.e., hydrovinylation products) include hydrovinylated farnesenes, hydrovinylated α-farnesene, hydrovinylated β-farnesene, hydrovinylated (3E,6E)-7,11-dimethyldodeca-1,3,6,10-tetrene, hydrovinylated (6E,8Z)-7,11-dimethyl-3-methylenedodeca-1,6,8-triene, hydrovinylated β-myrcene, hydrovinylated (E)-3,7-dimethylocta-1,3,6-triene, hydrovinylated (Z)-3-ethyl-7-methyl-octa-1,3,6-triene, hydrovinylated (Z)-3,7-dimethylocta-1,4,6-triene. More preferred hydrovinylated cross metathesis substrates include hydrovinylated farnesenes, hydrovinylated α-farnesene, hydrovinylated β-farnesene, hydrovinylated β-myrcene, and hydrovinylated (Z)-3,7-dimethylocta-1,4,6-triene. Most preferred hydrovinylated cross metathesis substrates include hydrovinylated β-farnesene, and hydrovinylated β-myrcene.

Preferred hydrovinylated olefinic substrates include 3-phenyl-1-butene, sulfonated 3-phenyl-1-butene, 3-tolyl-1-butene, sulfonated 3-tolyl-1-butene, hydrovinylated β-farnesene, hydrovinylated β-myrcene. More preferred olefinic substrates include 3-phenyl-1-butene, 3-tolyl-1-butene, hydrovinylated β-farnesene, hydrovinylated β-myrcene. Most preferred olefinic substrates include 3-phenyl-1-butene, 3-tolyl-1-butene, hydrovinylated β-farnesene.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

The following examples are to be considered as not being limiting of the invention as described herein, and are instead provided as representative examples of compositions and methods of the invention.

Examples

Materials and Methods

All solvents and reagents were purchased from commercial suppliers and used as received unless otherwise noted. All reactions were performed under ambient conditions unless otherwise noted. Hydrovinylation catalyst (HV-2) was prepared according to known methods, a representative procedure is described in Small, B. L.; Brookhart, M.; Bennett, A. M. A. *J. Am. Chem. Soc.* 1998, 120, 4049-4050 and Gibson, V. C.; Redshaw, C.; Solan, G. A. *Chem. Rev.* 2007, 107 (5), 1745-1776. Hydrovinylation catalyst (PPh$_3$)$_2$CoCl$_2$ was prepared according to known methods, a representative procedure is described in Cotton, F. A.; Faut, O. D.; Goodgame, D. M. L.; Holm, R. H. *J. Am. Chem. Soc.* 1961, 83, 1780. Metathesis catalyst [1,3-Bis-(2,6-diisopropylphenyl)-2-imidazolidinylidene]dichloro(o-isopropoxyphenylmethylene)ruthenium (II) (C711) was prepared according to standard methods. E-β-farnesene (purity 90%) and 9-decenoic acid (purity 95%) were from Bedoukian Research Inc. Methyl 9-decenoate was prepared from 9-decenoic acid according to known methods. Styrene (purity >99%), naphthalene (purity 99%), toluene (anhydrous, 95% purity), ethyl acetate (anhydrous, 99.8% purity), methanol (anhydrous, 99.8% purity), hexane (anhydrous, 95% purity), hexanes (anhydrous, >99.9% purity), methylene chloride (dichloromethane) (anhydrous, >99.8%), potassium hydroxide (flakes, 90% purity), sodium methoxide (25 wt % in methanol), Pd/C (10 wt %), and methyl styrene (i.e., tolyl styrene) (purity 99%; containing 60% meta, 40% para, and <1% ortho isomers), diethylaluminum chloride in hexanes (1.0 M) were from Sigma-Aldrich. Sodium dispersion (30-35 wt % in paraffin; Sigma-Aldrich) was washed with hexanes to remove paraffin then dried under high vacuum. Cis-2-butene-1,4-diol (95% purity; Sigma-Aldrich) was acetylated to 1,4-diacetoxy-2-butene according to known methods. Tetrakis(hydroxymethyl)phosphonium chloride (80% in water) from Sigma-Aldrich was converted to tris(hydroxymethyl)phosphine (THMP) as reported by Pederson et al., *Advanced Synthesis & Catalysis* 2002, 344, 728-735. 2-Allyloxyethanol (98% purity; Sigma-Aldrich) was acetylated to 2-allyloxyethyl acetate according to known methods. Silica gel 60 was from EMD. Ethylene (Grade 3.0, 99.9% purity) and hydrogen (4.5 Grade) were from Praxair. Chlorosulfonic acid (97% purity) and oleum (sulfuric acid with 20-30% free SO$_3$) were from Acros. Sodium hydroxide (50% in water) was from Ashland. Methanol (bulk) was from Nexeo solutions. 3-phenyl-1-butene was prepared as described herein.

GC Analytical Methods

Volatile products were analyzed using an Agilent 6850 gas chromatography (GC) instrument with a flame ionization detector (FID). The following conditions and equipment were used:
Column: HP-5, 30 m×0.25 mm (ID)×0.25 μm film thickness.
Manufacturer: Agilent
GC conditions: Injector temperature: 250° C.
Detector temperature: 280° C.
Oven temperature: Starting temperature: 100° C., hold time: 1 minute.
Ramp rate 10° C./min to 250° C., hold time: 12 minutes.
Carrier gas: Helium
Mean gas velocity: 31.3±3.5% cm/sec (calculated)
Split ratio: ~50:1
The products were characterized by comparing peaks with known standards, in conjunction with supporting data from mass spectrum analysis (GCMS-Agilent 5973N). GCMS analysis was accomplished with a second HP-5, 30 m×0.25 mm (ID)×0.25 μm film thickness GC column, using the same method as above.

An aliquot of the metathesis reaction was withdrawn at the desired times, filtered through a plug of silica gel and analyzed by gas chromatography.

Experimental Reactions

Reaction 1. Preparation of (4E,8E)-5,9,13-trimethyltetradeca-1,4,8,12-tetraene (hydrovinylated farnesene)

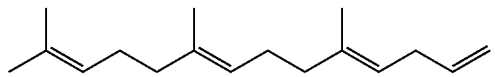 [SMILES: C=CC/C=C(\C)CC/C=C(\C)CCC=C(C)C]

In an argon filled glovebox, a 2 L pressure vessel equipped with a magnetic stirbar was charged with hydrovinylation catalyst HV-2 (1.01 g, 2.03 mmol), E-β-farnesene (20.0 mL, 81.2 mmol), naphthalene (521 mg, 4.06 mmol) and toluene (80 mL). To the stirring purple suspension was added powdered sodium (140 mg, 6.09 mmol). The suspension was allowed to stir under argon for 15 min affording a homogenous brown solution. The pressure vessel was sealed, removed from the glovebox, purged with ethylene and subsequently pressurized to 25 psi (132 mmol, 1.6 equiv). The reaction was sealed and allowed to stir for 12 h at room temperature. The reaction was vented, volatiles removed by rotary evaporation and the resulting residue purified by vacuum distillation to afford (4E,8E)-5,9,13-trimethyltetradeca-1,4,8,12-tetraene (17.7 g, 93.8% yield, >98% pure). $^1$H NMR (400 MHz, CDCl$_3$) δ 1.61 (s, 6H), 1.63 (s, 3H), 1.69 (s, 3H), 1.95-2.15 (m, 8H), 2.76 (pt, J=6.4 Hz, 1H), 4.96 (dpq, J=10.0, 1.7 Hz, 1H), 5.03 (dpq, J=17.1, 1.7 Hz, 1H), 5.08-5.21 (m, 2H), 5.81 (ddt, J=17.2, 10.0, 6.3 Hz, 1H). $^{13}$C NMR (101 MHz, CDCl$_3$) δ 15.94, 15.99, 17.66, 25.68, 26.56, 26.75, 32.26, 39.70, 39.73, 114.06, 121.37, 124.13, 124.40, 131.21, 135.00, 136.41, 137.43.

Reaction 2. Preparation of (2E,5E,9E)-6,10,14-trimethylpentadeca-2,5,9,13-tetraenyl acetate

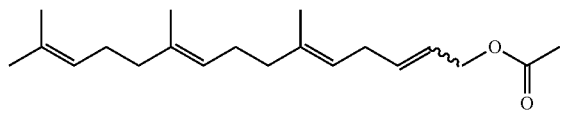 [SMILES: CC(=O)OCC=CC/C=C(\C)CC/C=C(\C)CCC=C(C)C]

In an argon filled glovebox, (4E,8E)-5,9,13-trimethyltetradeca-1,4,8,12-tetraene (25.0 g, 108 mmol), cis-1,4-diacetoxy-2-butene (25.7 mL, 161 mmol, 1.5 equiv), and metathesis catalyst C711 (10 ppm, 51 µl, 0.021 M) were combined in a round bottom flask equipped with a magnetic stirbar and vacuum adapter. The reaction was allowed to stir at room temperature under vacuum (500 millitorr) for 2 hours. The reaction mixture was then quenched with a solution of tris(hydroxymethyl)phosphine in isopropanol (1.5 mL, 1.0 M, 1.5 mmol) and heated to 70° C. for 1 hour. The reaction mixture was cooled to room temperature and partitioned between water and ethyl acetate (1:1, 400 mL). The organic phase was separated, washed with water (2×100 mL), brine (2×100 mL), and then dried over sodium sulfate. The product was distilled at 125° C./14 millitorr to yield (2E,5E,9E)-6,10,14-trimethylpentadeca-2,5,9,13-tetraenyl acetate [(17.6 g, 57.8 mmol, 96.5% pure); (3.0 g, 9.9 mmol, 93% pure)]. $^1$H NMR (400 MHz, CDCl$_3$, mixture of cis and trans) δ 1.55-1.70 (m, 12H), 1.95-2.12 (m, 11H), 2.76 (t, J=6.4 Hz, 2H, trans), 2.81 (t, J=7.0 Hz, 2H, cis), 4.51 (d, J=6.4 Hz, 2H, trans), 4.65 (d, J=6.8 Hz, 2H, cis), 5.10-5.18 (m, 3H), 5.48-5.65 (m, 1H), 5.70-5.80 (m, 1H). $^{13}$C NMR (101 MHz, CDCl$_3$, mixture of cis and trans) δ 16.0, 17.6, 21.0, 25.7, 26.5, 26.7, 30.7, 39.6, 60.3, 65.2, 120.8, 121.3, 122.9, 123.6, 124.0, 124.0, 124.3, 131.2, 133.9, 134.9, 135.0, 136.4, 136.8, 170.8.

Reaction 3. Preparation of 6,10,14-trimethylpentadecyl acetate

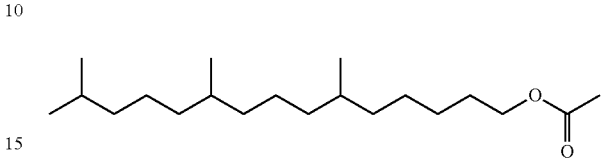

To a Fisher-Porter tube equipped with a stirbar and pressure gauge was added (2E,5E,9E)-6,10,14-trimethylpentadeca-2,5,9,13-tetraenyl acetate (17.1 g, 56.2 mmol) and Pd/C (0.299 g, 5 mol %). The reaction vessel was sealed, sparged with argon for 10 minutes, and then attached to a metal Schlenk line connected to a hydrogen tank. The reaction was sparged with hydrogen, pressurized to 30 psig, and heated to 30° C. with stirring. Upon completion, as determined by GC analysis, the reaction vessel was vented and the crude mixture was diluted with hexanes (50 mL) and filtered through a plug of silica gel. The silica gel plug was washed (3×50 mL 10% ethyl acetate in hexane) and the combined organic phase was concentrated to afford 6,10,14-trimethylpentadecyl acetate (18.1 g, 57.9 mmol, 89% pure). $^1$H NMR (400 MHz, CDCl$_3$) δ 0.83-0.86 (m, 12H), 0.98-1.17 (m, 6H), 1.18-1.40 (m, 14H), 1.52 (sept, J=6.7 Hz, 1H), 1.61 (m, 2H), 2.03 (s, 3H), 4.04 (t, J=6.6 Hz, 2H). $^{13}$C NMR (101 MHz, CDCl$_3$, mixture of diastereomers) δ 19.6, 19.7, 19.7, 19.7, 21.0, 22.6, 22.7, 24.4, 24.8, 24.8, 26.3, 26.7, 28.0, 28.6, 32.7, 32.7, 32.8, 32.8, 36.9, 37.0, 37.3, 37.3, 37.4, 37.4, 39.4, 64.7, 171.2.

Reaction 4. Preparation of 6,10,14-trimethylpentadecan-1-ol

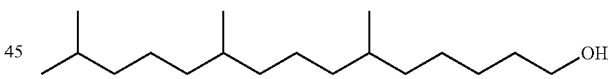

A round bottom flasked equipped with a magnetic stirbar was charged with 6,10,14-trimethylpentadecyl acetate (13.3 g, 42.6 mmol) and methanol (43 mL). Potassium hydroxide (2.63 g, 46.8 mmol) was added and the reaction was stirred at room temperature for 2 hours. All volatiles were subsequently removed under rotary evaporation and the resulting residue was partitioned between hexane and water (120 mL, 1:1) and neutralized with aqueous HCl (0.5 M). The organic phase was separated, washed with water (2×50 mL), brine (2×50 mL), and then dried over sodium sulfate. Volatiles were removed under rotary evaporation and purification by column chromatography (SiO$_2$, 8% ethyl acetate in hexane) afforded 6,10,14-trimethylpentadecan-1-ol (12.5 g, 46.2 mmol, 98.3% pure). $^1$H NMR (400 MHz, CDCl$_3$) δ 0.83-0.87 (m, 12H), 0.98-1.18 (m, 6H), 1.19-1.41 (m, 15 H), 1.46-1.61 (m, 3H), 3.63 (t, J=6.4 Hz, 2H). $^{13}$C NMR (101 MHz, CDCl$_3$, mixture of diastereomers) δ 21.3, 21.4, 21.4, 21.4, 24.2, 24.3, 26.0, 26.3, 26.4, 27.6, 28.4, 28.4, 29.4, 34.0, 34.1, 34.1, 34.1, 34.2, 38.2, 38.3, 38.5, 38.6, 38.6, 38.6, 38.7, 40.5, 63.7.

Reaction 5. Preparation of sodium 6,10,14-trimethylpentadecyl sulfate

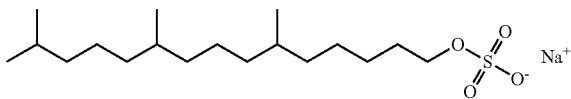 [SMILES: CC(C)CCCC(C)CCCC(C)CCCCCOS(=O)(=O)[O-] ; [Na+]]

6,10,14-trimethylpentadecan-1-ol (7.9 g, 29.2 mmol) was added to a round bottom flask equipped with a magnetic stirbar and cooled to −5° C. under a blanket of argon. Chlorosulfonic acid (3.68 g, 31.6 mmol) was added dropwise to the stirring reaction mixture. Upon complete addition, the reaction was stirred for an additional 2 hours at −5° C. Volatiles were removed under rotary evaporation and the resulting residue was redissolved in methanol (31 mL). Sodium methoxide (1.75 g, 30.8 mmol) was added and the reaction stirred for 30 minutes. The reaction was subsequently concentrated to dryness affording sodium 6,10,14-trimethylpentadecyl sulfate (10.3 g, 27.6 mmol, >98% pure). $^1$H NMR (400 MHz, CDCl$_3$) δ 0.79-0.83 (m, 12H), 0.95-1.13 (m, 6H), 1.15-1.40 (m, 14H), 1.41-1.55 (m, 3H), 3.66 (t, J=6.6 Hz, 2H). $^{13}$C NMR (101 MHz, CDCl$_3$, mixture of diastereomers) δ 19.9, 20.0, 20.0, 22.9, 23.0, 24.3, 24.6, 26.3, 26.7, 27.8, 29.6, 32.5, 32.5, 36.9, 37.0, 37.1, 37.2, 37.2, 37.3, 37.3, 39.2, 39.3, 39.5, 39.7, 39.9, 40.2, 66.0.

Reaction 6. Preparation of 2-(6,10,14-trimethylpentadecyloxy)ethyl acetate

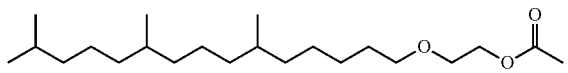 [SMILES: CC(=O)OCCOCCCCCC(C)CCCC(C)CCCC(C)C]

In an argon filled glovebox, (4E,8E)-5,9,13-trimethyltetradeca-1,4,8,12-tetraene (25.0 g, 108 mmol), 2-(allyloxy)ethyl acetate (46.5 g, 323 mmol), and metathesis catalyst C711 (76.5 mg, 1000 ppm) were combined in a round bottom flask equipped with a magnetic stirbar and vacuum adapter. The reaction was allowed to stir at room temperature under vacuum (500 millitorr) for 3 hours. The reaction mixture was then quenched with a solution of tris(hydroxymethyl) phosphine in isopropanol (6.0 mL, 1.0 M, 6.0 mmol) and heated to 70° C. for 1 hour. The reaction mixture was cooled to room temperature and partitioned between water and ethyl acetate (1:1, 400 mL). The organic phase was separated, washed with water (2×100 mL), brine (2×100 mL), and then dried over sodium sulfate. Low boiling point impurities were removed by vacuum distillation and a portion of the remaining material (12.6 g, ca. 36 mmol) was combined with Pd/C (0.192 g, 5 mol %) in a Fisher-Porter tube equipped with a stirbar and pressure gauge. The reaction vessel was sealed, sparged with argon for 10 minutes, and then attached to a metal Schlenk line connected to a hydrogen tank. The reaction was sparged with hydrogen, pressurized to 30 psig, and heated to 30° C. with stirring. Upon completion, as determined by GC analysis, the reaction vessel was vented and the crude mixture was diluted with hexanes (25 mL) and filtered through a plug of silica gel. The silica gel plug was washed (3×25 mL 10% ethyl acetate in hexane) and the combined organic phase was concentrated to afford 2-(6,10,14-trimethylpentadecyloxy) ethyl acetate (12.6 g, 35.3 mmol, >98% pure). $^1$H NMR (400 MHz, CDCl$_3$) δ 0.82-0.86 (m, 12H), 1.00-1.18 (m, 6H), 1.18-1.41 (m, 14H), 1.43-1.62 (m, 3H), 2.93 (s, 3H), 3.45 (t, J=6.6 Hz, 2H), 3.61 (t, J=4.8 Hz, 2H), 4.20 (t, J=4.8 Hz, 2H). $^{13}$C NMR (101 MHz, CDCl$_3$, mixture of diastereomers) δ 19.6, 19.7, 19.7, 19.7, 20.9, 22.6, 23.0, 24.4, 24.8, 24.8, 26.4, 26.9, 26.9, 28.0, 29.3, 29.6, 32.7, 32.7, 32.7, 32.8, 36.7, 36.8, 37.0, 37.0, 37.3, 37.4, 37.4, 37.4, 37.4, 39.4, 63.7, 68.5, 71.5.

Reaction 7. Preparation of 2-(6,10,14-trimethylpentadecyloxy)ethanol

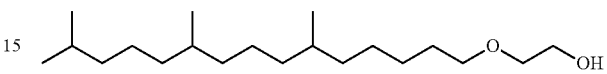

A round bottom flask equipped with a magnetic stirbar was charged with 2-(6,10,14-trimethylpentadecyloxy)ethyl acetate (12.6 g, 35.3 mmol) and methanol (36 mL). Potassium hydroxide (2.4 g, 42.4 mmol) was added and the reaction mixture was stirred at room temperature for 2 hours. All volatiles were subsequently removed under rotary evaporation and the resulting residue was partitioned between hexane and water (120 mL, 1:1) and neutralized with aqueous HCl (0.5 M). The organic phase was separated, washed with water (2×50 mL), brine (2×50 mL), and then dried over sodium sulfate. Volatiles were removed under rotary evaporation and the resulting residue purified by column chromatography (SiO$_2$, 6-14% ethyl acetate in hexane) affording 2-(6,10,14-trimethylpentadecyloxy)ethanol (7.0 g, 22.3 mmol, 98.3% pure). $^1$H NMR (400 MHz, CDCl$_3$) δ 0.83-0.87 (m, 12H), 1.00-1.18 (m, 6H), 1.19-1.40 (m, 14H), 1.48-1.64 (m, 3 H), 2.01 (t, J=6.2 Hz, 1H), 3.47 (t, J=6.6 Hz, 2 H), 3.53 (t, J=4.6 Hz, 2H), 3.73 (pseudo quartet, J=5.2 Hz, 2H). $^{13}$C NMR (101 MHz, CDCl$_3$) δ 19.9, 19.9, 19.9, 20.0, 22.9, 24.7, 25.0, 26.7, 27.1, 27.1, 28.2, 29.9, 32.9, 32.9, 33.0, 33.0, 37.2, 37.3, 37.5, 37.6, 37.6, 37.6, 37.6, 39.6, 62.1, 71.6, 71.9.

Reaction 8. Preparation of 7,11,15-trimethylhexadecan-2-yl)benzene

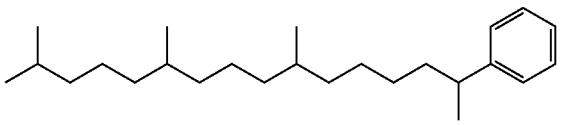 [SMILES: CC(C)CCCC(C)CCCC(C)CCCCC(C)c1ccccc1]

In an argon filled glovebox, (4E,8E)-5,9,13-trimethyltetradeca-1,4,8,12-tetraene (30.0 g, 129 mmol), 3-phenyl-1-butene (51.2 g, 387 mmol), and metathesis catalyst C711 (9.2 mg, 100 ppm) were combined in a round bottom flask equipped with a magnetic stirbar and vacuum adapter. The reaction was allowed to stir at room temperature under vacuum (500 millitorr) for 1.5 hours. The reaction mixture was filtered through a plug of silica gel and the plug was washed with hexane (2×50 mL). The organic phase was combined, solvent removed by rotary evaporation, and low boiling point impurities were removed by vacuum distillation. A portion of the remaining material (12.3 g, 36.6 mmol) was combined with Pd/C (0.974 g, 2.5 mol %) in a Fisher-Porter tube equipped with a stirbar and pressure gauge. The reaction vessel was sealed, sparged with argon for 10 minutes, and then attached to a metal Schlenk line connected to a hydrogen tank. The reaction was sparged with hydrogen, pressurized to 30 psig, and heated to 30° C. with stirring. Upon completion, as determined by GC analysis, the reaction vessel was vented and the crude mixture was diluted with hexanes (25 mL) then filtered through a plug of silica gel. The silica gel plug was washed (3×50 mL 10% ethyl acetate in hexane) and the combined organic phase was concentrated. The resulting residue was purified by column chromatography (SiO$_2$, hexanes) to yield (7,11,15-trimethylhexadecan-2-yl)benzene [(2.7 g, 7.8 mmol, 92.4% pure), (6.6 g, 19.2 mmol, 90% pure)]. $^1$H NMR (400 MHz, CDCl$_3$) δ 0.79-0.90 (m, 12H), 0.98-1.11 (m, 4H), 1.12-1.44 (m, 19H), 1.48-1.65 (m, 3H), 2.68 (sextet, J=7.0 Hz, 1H), 7.15-7.22 (m, 3H), 7.24-7.32 (m, 2H). $^{13}$C NMR (101 MHz, CDCl$_3$, mixture of diastereomers) δ 19.7, 19.7, 19.7, 19.8, 22.3, 22.3, 22.6, 22.7, 24.4, 24.8, 24.8, 27.1, 27.2, 28.0, 28.1, 28.1, 32.7, 32.7, 32.8, 32.8, 36.9, 37.0, 37.3, 37.3, 37.4, 37.4, 37.4, 37.4, 37.4, 38.5, 39.4, 40.0, 125.7, 127.0, 128.2, 148.0, 148.0.

Reaction 9. Preparation of sodium 4-(7,11,15-trimethylhexadecan-2-yl)benzenesulfonate

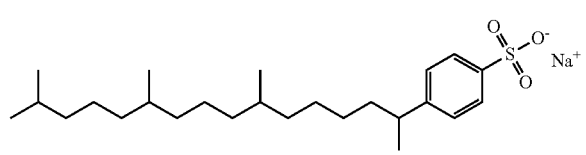 [SMILES: CC(C)CCCC(C)CCCC(C)CCCCC(C)c1ccc(S(=O)(=O)[O-])cc1 ; [Na+]]

(7,11,15-trimethylhexadecan-2-yl)benzene (6.3 g, 18.3 mmol) was added to a round bottom flask equipped with a magnetic stirbar and cooled to 0° C. under a blanket of argon. Oleum (1.3 weight %, 20% free SO$_3$) was added dropwise to the reaction mixture while maintaining a temperature of <25° C. during addition. The reaction was stirred for 45 minutes at 0° C. and 1.5 hour at room temperature. The crude material was slowly added to a stirred aqueous solution of NaOH (20%) at 0° C. Solid formation was observed and the mixture was allowed to stir for an additional 2 hours after complete addition. The precipitate was filtered, washed with cold water (2×5 mL), and dried in vacuo to yield sodium 4-(7,11,15-trimethylhexadecan-2-yl)benzenesulfonate (4.1 g, 9.2 mmol, >95% pure). $^1$H NMR (400 MHz, DMSO-d$_6$) δ 0.76-0.87 (m, 12H), 0.95-1.41 (m, 23H), 1.45-1.57 (m, 3H), 2.65 (sext, J=7.0 Hz, 1H), 7.12 (d, J=8.0 Hz, 2H), 7.52 (d, J=8.4 Hz, 2H). $^{13}$C NMR (101 MHz, DMSO-d$_6$, mixture of diastereomers) δ 19.5, 19.5, 19.6, 19.6, 22.2, 22.3, 22.5, 22.5, 23.8, 24.2, 26.5, 27.4, 27.5, 32.0, 32.1, 36.3, 36.4, 36.6, 36.7, 36.7, 36.8, 37.7, 38.9, 38.9, 125.6, 125.9, 145.8, 147.6.

Reaction 10. Preparation of ((1E,4E,8E,)-5,9,13-trimethyltetradeca-1,4,8,12-tetraenyl) benzene

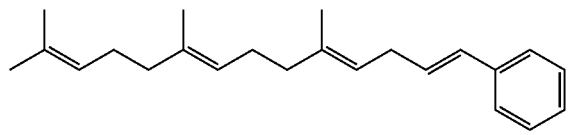 [SMILES: CC(C)=CCC/C(C)=C/CC/C(C)=C/C/C=C/c1ccccc1]

In an argon filled glovebox, (4E,8E)-5,9,13-trimethyltetradeca-1,4,8,12-tetraene (30.0 g, 129.1 mmol), styrene (40.3 g, 387 mmol), and metathesis catalyst C711 (2.3 mg, 25 ppm) were combined in a round bottom flask equipped with a magnetic stirbar and vacuum adapter. The reaction was allowed to stir at room temperature under vacuum (500 millitorr) for 1.5 hours. Then, the reaction mixture was filtered through a plug of silica gel and the plug was washed with hexane (2×50 mL). The organic phase was combined, solvent removed by rotary evaporation, and the product was vacuum distilled at 147° C./15 mTorr to yield ((1E,4E,8E)-5,9,13-trimethyltetradeca-1,4,8,12-tetraenyl)benzene (8.1 g, 26 mmol, 91% pure). $^1$H NMR (400 MHz, CDCl$_3$) δ 1.61 (s, 3H), 1.63 (s, 3H), 1.68 (s, 3H), 1.70 (s, 3H), 1.96-2.19 (m, 8H), 2.93 (t, J=6.6 Hz, 2H), 5.08-5.19 (m, 2H), 5.23-5.29 (m, 1H), 6.21 (dt, J=15.8, 6.4 Hz, 1H), 6.40 (d, J=15.8 Hz, 1H), 7.17-7.23 (m, 1H), 7.27-7.32 (m, 2H), 7.33-7.38 (m, 2H). $^{13}$C NMR (101 MHz, CDCl$_3$) δ 16.0, 16.1, 17.7, 25.7, 26.6, 26.8, 31.5, 39.7, 39.7, 121.4, 124.1, 124.4, 125.9, 126.8, 128.4, 129.5, 129.5, 131.2, 135.1, 136.7, 137.9.

Reaction 11. Preparation of (5,9,13-trimethyltetradecyl)benzene

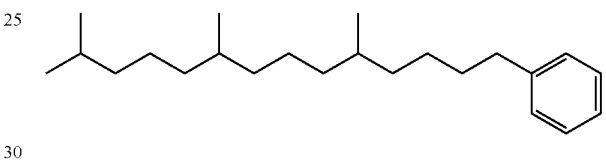

To a Fisher-Porter tube equipped with stirbar and pressure gauge was added ((1E,4E,8E,)-5,9,13-trimethyltetradeca-1,4,8,12-tetraenyl)benzene (8.1 g, 26.3 mmol) and Pd/C (0.140 g, 5 mol %). The reaction vessel was sealed, sparged with argon for 10 minutes, and then attached to a metal Schlenk line connected to a hydrogen tank. The reaction was sparged with hydrogen, pressurized to 30 psig, and heated to 30° C. with stirring. Upon completion, as determined by GC analysis, the reaction vessel was vented and the crude mixture was diluted with hexanes (25 mL) and filtered through a plug of silica gel. The silica gel plug was washed (3×50 mL 10% ethyl acetate in hexane) and the combined organic phase was concentrated. The resulting residue was purified by column chromatography (SiO$_2$, hexanes) to yield (5,9,13-trimethyltetradecyl)benzene (7.1 g, 22.4 mmol, 94% pure). $^1$H NMR (400 MHz, CDCl$_3$) δ 0.86-0.94 (m, 12H), 1.04-1.22 (m, 6H), 1.22-1.48 (m, 12H), 1.50-1.68 (m, 3H), 2.64 (t, J=7.8 Hz, 2H), 7.17-7.23 (m, 3H), 7.28-7.33 (m, 2H). $^{13}$C NMR (101 MHz, CDCl$_3$, mixture of diastereomers) δ 19.7, 19.7, 19.8, 19.8, 22.6, 22.7, 24.5, 24.8, 24.8, 26.8, 26.8, 28.0, 31.9, 32.7, 32.7, 32.8, 32.8, 36.0, 36.9, 37.0, 37.3, 37.4, 37.4, 37.4, 37.5, 39.4, 125.5, 128.2, 128.4, 142.9.

Reaction 12. Preparation of sodium 4-(5,9,13-trimethyltetradecyl)benzenesulfonate

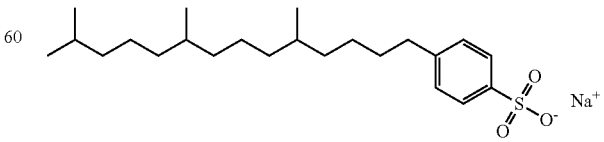

(5,9,13-trimethyltetradecyl)benzene (5.0 g, 16 mmol) was added to a round bottom flask equipped with a magnetic stirbar and cooled to −5° C. under a blanket of argon. Oleum (1.3 weight %, 20% free SO₃) was added dropwise to the reaction mixture while maintaining a temperature of <25° C. during addition. The reaction was stirred for 45 minutes at 0° C. and 1.5 hour at room temperature. The crude material was slowly added to a stirred aqueous solution of NaOH (20%) at 0° C. Solid formation was observed and the mixture was allowed to stir for an additional 2 hours after complete addition. The precipitate was filtered, washed with cold water (2×10 mL), and dried in vacuo to yield sodium 4-(5,9,13-trimethyltetradecyl)benzenesulfonate (3.1 g, 7.4 mmol, >90% pure). $^1$H NMR (400 MHz, DMSO-d$_6$) δ 0.80 (s, 3H), 0.82 (s, 3H), 0.84 (s, 3H), 0.85 (s, 3H), 1.00-1.16 (m, 6H), 1.17-1.43 (m, 12H), 1.44-1.60 (m, 3H), 2.56 (t, J=7.6 Hz, 2H), 7.12 (d, J=8.1 Hz, 2H), 7.51 (d, J=8.2 Hz, 2H). $^{13}$C NMR (101 MHz, DMSO-d$_6$, mixture of diastereomers) δ 19.5, 19.6, 19.6, 22.5, 22.5, 23.8, 24.2, 26.1, 27.4, 31.3, 32.0, 32.1, 34.9, 36.2, 36.3, 36.6, 36.7, 36.7, 36.7, 36.8, 36.8, 38.8, 125.5, 127.4, 142.6, 145.7.

Reaction 13. Preparation of (9E,12E,16E)-methyl 13,17,21-trimethyldocosa-9,12,16,20-tetraenoate

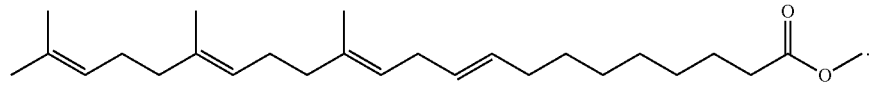 [SMILES: COC(=O)CCCCCCC/C=C/C/C=C(\C)CC/C=C(\C)CCC=C(C)C]

In an argon filled glovebox, (4E,8E)-5,9,13-trimethyltetradeca-1,4,8,12-tetraene (2.0 g, 8.61 mmol), methyl-9-decenoate (4.76 g, 25.8 mmol), and metathesis catalyst C711 (100 ppm, 41.3 µL, 0.021 M) were combined in a round bottom flask equipped with a magnetic stirbar and vacuum adapter. The reaction was allowed to stir at room temperature under vacuum (500 millitorr) for 2 hours. The reaction mixture was then quenched with a solution of tris(hydroxymethyl)phosphine in isopropanol (2.0 mL, 1.0 M, 2.0 mmol) and heated to 70° C. for 1 hour. The reaction mixture was cooled to room temperature, diluted with water and ethyl acetate. The organic phase was separated, washed with water (2×25 mL), brine (2×25 mL), and then dried over sodium sulfate. Chromatography purification using 2% ethyl acetate in hexane yielded (9E,12E,16E)-methyl 13,17,21-trimethyldocosa-9,12,16,20-tetraenoate (1.3 g, 3.4 mmol, 87% pure). $^1$H NMR (400 MHz, CDCl$_3$) δ 1.23-1.37 (m, 8H), 1.56-1.65 (m, 10H), 1.66-1.69 (m, 2H), 1.92-2.16 (m, 12H), 2.30 (t, J=7.6 Hz, 2H), 2.68 (t, J=5.7 Hz, 2H), 3.66 (s, 3H), 5.05-5.18 (m, 3H), 5.35-5.41 (m, 2H). $^{13}$C NMR (101 MHz, CDCl$_3$) δ 16.0, 16.0, 17.7, 24.9, 25.7, 26.6, 26.7, 29.0, 29.1, 29.1, 29.5, 31.1, 32.5, 34.1, 39.7, 39.7, 51.4, 122.5, 124.2, 124.4, 128.7, 130.2, 131.2, 135.0, 135.6, 174.3.

Reaction 14. Preparation of (2E,5E,9E)-methyl 6,10,14-trimethylpentadeca-2,5,9,13-tetraenoate

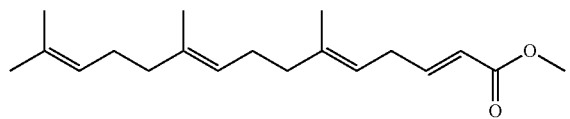 [SMILES: COC(=O)/C=C/C/C=C(\C)CC/C=C(\C)CCC=C(C)C]

In an argon filled glovebox, (4E,8E)-5,9,13-trimethyltetradeca-1,4,8,12-tetraene (0.500 g, 2.15 mmol), methyl acrylate (0.560 g, 6.45 mmol), and metathesis catalyst C711 (51.0 µL, 0.021 M, 500 ppm) were combined in a round bottom flask equipped with a magnetic stirbar. The reaction was allowed to stir at room temperature for 16 hours. The reaction mixture was then quenched with a solution of tris(hydroxymethyl)phosphine in isopropanol (2.0 mL, 1.0 M, 2.0 mmol) and heated to 70° C. for 1 hour. The reaction mixture was cooled to room temperature, diluted with water and ethyl acetate. The organic phase was separated, washed with water (2×5 mL), brine (2×5 mL), and then dried over sodium sulfate. Chromatography purification using 3% ethyl acetate in hexane yielded (2E,5E,9E)-methyl 6,10,14-trimethylpentadeca-2,5,9,13-tetraenoate (0.15 g, 0.52 mmol, 80% pure). $^1$H NMR (400 MHz, CDCl$_3$) δ 1.60 (s, 6H), 1.61 (s, 3H), 1.67 (s, 3H), 1.94-2.16 (m, 8H), 2.89 (t, J=6.6 Hz, 2H), 3.72 (s, 3H), 5.06-5.19 (m, 3H), 5.81 (d, J=15.6 Hz, 1H), 6.95 (dt, J=15.6, 6.3 Hz, 1H). $^{13}$C NMR (101 MHz, CDCl$_3$) δ 16.0, 16.1, 17.7, 25.7, 26.4, 26.7, 30.7, 29.6, 29.7, 51.4, 118.8, 120.6, 123.9, 124.4, 131.2, 135.3, 138.5, 148.0, 167.2.

Reaction 15. Synthesis of 3-phenyl-1-butene by hydrovinylation of styrene

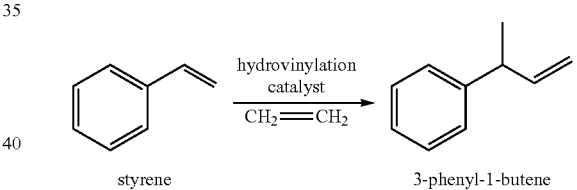

Under a stream of argon, (PPh$_3$)$_2$CoCl$_2$ (15.0 g, 22.9 mmol), dichloromethane (3.0 L), and styrene (4.0 L, 34.4 mol) were combined in an 18 L Parr reactor. The reactor was sealed, and cooled to −10° C. while the headspace was purged with ethylene. A solution of diethylaluminum chloride in hexanes (1.0 M, 115 mL, 115 mmol) was introduced. The reactor was promptly sealed and charged with ethylene (435 psi). After 14 h the pressure was released the reaction passed through a plug of silica gel. The silica gel was washed with dichloromethane and the organic fractions were combined and concentrated under rotary evaporation. Subsequent purification by vacuum distillation afforded 3-phenyl-1-butene (Bpt 45.7° C. to 46.0° C. at 5 mmHg, 4.1 kg, 89% yield and 99% purity). 3-Phenyl-1-butene was produced in >99% isomeric purity (neither 2-phenyl-2-butene nor 2-phenyl-1-butene isomers were detected by $^1$H NMR and <0.5% 2-phenyl-2-butene was detected by GC analysis). $^1$H NMR (400 MHz, CDCl$_3$) δ 1.66 (d, J=6.8 Hz, 3H), 3.75 (m, 1H), 5.34 (ddd, J=10.4, 1.6 and 1.6 Hz, 1H), 5.36 (ddd, J=17.2, 1.6 and 1.6 Hz, 1H), 6.31 (ddd, J=17.2, 10.4 and 6.4 Hz, 1H), 7.28-7.46 (m, 5H); $^{13}$C NMR (101 MHz, CDCl$_3$) 20.7, 43.2, 113.0, 126.1, 127.2, 128.4, 143.2, 145.4.

Reaction 16. Dimerization of E-β-farnesene

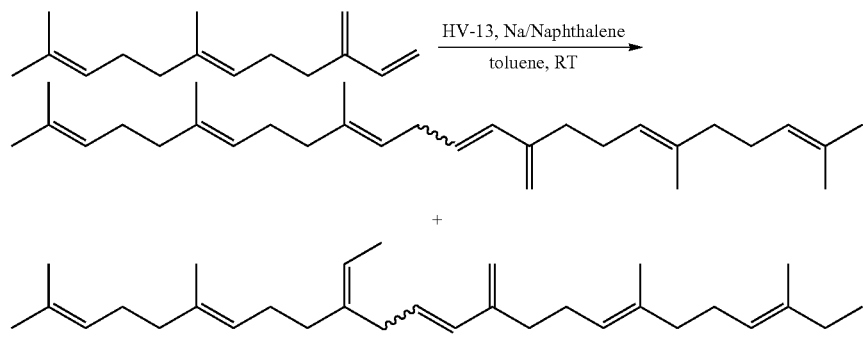

In an argon filled glovebox, a 20 mL scintillation vial equipped with a magnetic stirbar was charged with HV-13 (82.7 mg, 0.203 mmol), E-β-farnesene (2.00 mL, 8.12 mmol), naphthalene (52.1 mg, 0.406 mmol) and toluene (8 mL). To the stirring suspension was added powdered sodium (14 mg, 0.61 mmol). The suspension was allowed to stir under argon for 12 h at room temperature. After 12 h, an aliquot was taken, filtered through a plug of silica gel. Analysis by gas chromatography showed >98% conversion to a mixture of four dimers, confirmed by GC-MS, in a ratio of 2.8:6.7:61.0:29.5.

Reaction 17. Self-metathesis of hydrovinylated farnesene

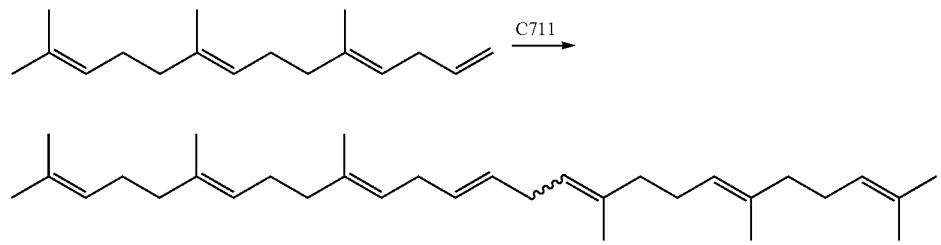

In an argon filled glovebox, a 20 mL scintillation vial equipped with a magnetic stirbar was charged with 1000 ppm of C711 (5.4 mg, 0.0075 mmol), hydrovinylated farnesene (2 mL, 7.6 mmol) and toluene (8 mL). The reaction was allowed to stir under argon for 4 h at room temperature. After 4 h, an aliquot was taken, filtered through a plug of silica gel. Analysis by gas chromatography showed 9% yield of a high boiling compound. GC-MS analysis of this peak indicated it had a molecular weight consistent with a self-metathesis product.

The claimed invention is:

1. A method of making at least one cross metathesis product, the method comprising: forming a first composition comprising at least one olefinic substrate, at least one hydrovinylation catalyst, and ethylene; subjecting the first composition to conditions effective to promote a hydrovinylation reaction to form at least one hydrovinylated olefinic substrate; forming a second composition comprising the at least one hydrovinylated olefinic substrate, at least one cross metathesis substrate selected from at least one terpene, and at least one olefin metathesis catalyst; and subjecting the second composition to conditions effective to promote a cross metathesis reaction to form at least one cross metathesis product.

2. The method of claim 1, wherein the at least one terpene is farnesene, α-farnesene, β-farnesene, or β-myrcene.

3. The method of claim 2, wherein the at least one olefinic substrate is selected from internal olefins, alpha olefins, or a combination thereof.

4. The method of claim 3, wherein the at least one olefin metathesis catalyst is a Group 8 transition metal complex having the structure of formula (I):

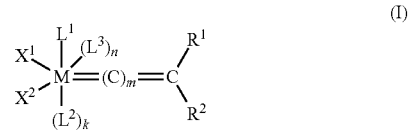

in which:
M is a Group 8 transition metal;
$L^1$, $L^2$, and $L^3$ are independently selected from neutral electron donor ligands;
n is 0 or 1, such that $L^3$ may or may not be present;
m is 0, 1, or 2;
k is 0 or 1;
$X^1$ and $X^2$ are independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein one or both of $R^1$ and $R^2$ may have the structure —$(W)_n$—$U^+$ V⁻, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

5. The method of claim 1, further comprising subjecting the at least one cross metathesis product to conditions effective to promote olefin hydrogenation to form at least one hydrogenated cross metathesis product.

6. The method of claim 3, wherein the internal olefin or alpha olefin comprises at least one aryl group such that the at least one cross metathesis product comprises the at least one aryl group.

7. The method of claim 6, further comprising subjecting the at least one cross metathesis product comprising the at least one aryl group to conditions effective to promote olefin hydrogenation to form at least one hydrogenated cross metathesis product.

8. The method of claim 7, further comprising subjecting the at least one hydrogenated cross metathesis product to conditions effective to promote an aromatic sulfonation reaction to form at least one sulfonated cross metathesis product.

9. The method of claim 3, wherein the internal olefin or the alpha olefin comprises at least one functional group selected from hydroxyl or acyloxy such that the at least one cross metathesis product comprises the at least one functional group selected from hydroxyl or acyloxy.

10. The method of claim 9, further comprising subjecting the at least one cross metathesis product comprising the at least one functional group selected from hydroxyl or acyloxy to conditions effective to promote olefin hydrogenation to form at least one hydrogenated cross metathesis product.

11. The method of claim 10, further comprising subjecting the at least one hydrogenated cross metathesis product to conditions effective to promote a sulfation reaction to form at least one sulfated cross metathesis product.

* * * * *

UNITED STATES PATENT AND TRADEMARK OFFICE
CERTIFICATE OF CORRECTION

PATENT NO. : 9,663,440 B2  
APPLICATION NO. : 14/782699  
DATED : May 30, 2017  
INVENTOR(S) : Adam M. Johns et al.

It is certified that error appears in the above-identified patent and that said Letters Patent is hereby corrected as shown below:

In the Specification

On Column 75, Scheme 15:

replace "  Styrene " with -- Styrene --

On Column 76, Scheme 16:

replace " 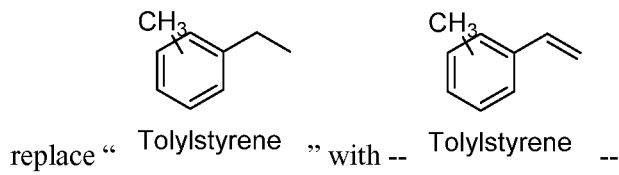 Tolylstyrene " with -- Tolylstyrene --

Signed and Sealed this  
Twenty-fifth Day of July, 2017

Joseph Matal  
*Performing the Functions and Duties of the*  
*Under Secretary of Commerce for Intellectual Property and*  
*Director of the United States Patent and Trademark Office*